United States Patent
Webster et al.

(10) Patent No.: US 10,702,526 B2
(45) Date of Patent: Jul. 7, 2020

(54) INHIBITORS OF IMMUNE CHECKPOINT MODULATORS AND RELATED METHODS

(71) Applicant: eFFECTOR Therapeutics, Inc., San Diego, CA (US)

(72) Inventors: Kevin R. Webster, San Diego, CA (US); Vikas Goel, San Diego, CA (US)

(73) Assignee: eFFECTOR Therapeutics Inc., San Diego, CA (US)

( * ) Notice: Subject to any disclaimer, the term of this patent is extended or adjusted under 35 U.S.C. 154(b) by 714 days.

(21) Appl. No.: 15/130,538

(22) Filed: Apr. 15, 2016

(65) Prior Publication Data

US 2016/0303124 A1      Oct. 20, 2016

Related U.S. Application Data

(60) Provisional application No. 62/150,140, filed on Apr. 20, 2015, provisional application No. 62/260,917, filed on Nov. 30, 2015.

(51) Int. Cl.
| | | |
|---|---|---|
| *A61K 31/519* | (2006.01) | |
| *A61K 31/52* | (2006.01) | |
| *A61K 31/506* | (2006.01) | |
| *A61K 39/395* | (2006.01) | |
| *A61K 31/713* | (2006.01) | |
| *A61K 45/06* | (2006.01) | |
| *A61K 39/00* | (2006.01) | |

(52) U.S. Cl.
CPC .......... *A61K 31/506* (2013.01); *A61K 31/713* (2013.01); *A61K 39/3955* (2013.01); *A61K 45/06* (2013.01); *A61K 2039/505* (2013.01); *Y02A 50/389* (2018.01); *Y02A 50/463* (2018.01)

(58) Field of Classification Search
None
See application file for complete search history.

(56) References Cited

U.S. PATENT DOCUMENTS

| | | | |
|---|---|---|---|
| 8,071,607 B2 | 12/2011 | Coulter et al. | |
| 8,486,953 B2 | 7/2013 | Austen et al. | |
| 8,697,713 B2 | 4/2014 | Jakel et al. | |
| 8,901,138 B2 | 12/2014 | Blum et al. | |
| 9,382,248 B2 * | 7/2016 | Reich | C07D 471/04 |
| 9,669,031 B2 * | 6/2017 | Reich | C07D 471/04 |
| 2010/0143341 A1 | 6/2010 | Taylor et al. | |
| 2014/0099254 A1 | 4/2014 | Chang et al. | |
| 2014/0135309 A1 | 5/2014 | Blum et al. | |
| 2014/0194430 A1 | 7/2014 | Eis et al. | |
| 2014/0228370 A1 | 8/2014 | Eis et al. | |
| 2014/0288069 A1 | 9/2014 | Eis et al. | |
| 2014/0296231 A1 | 10/2014 | Eis et al. | |
| 2015/0376181 A1 * | 12/2015 | Reich | C07D 471/04 |
| | | | 514/210.21 |

FOREIGN PATENT DOCUMENTS

| | | | |
|---|---|---|---|
| WO | 2010/023181 A1 | 3/2010 | |
| WO | 2010/036404 A2 | 4/2010 | |
| WO | WO-2010055072 A2 * | 5/2010 | .......... A61K 31/436 |
| WO | 2012/175591 A1 | 12/2012 | |
| WO | WO-2013019906 A1 * | 2/2013 | ....... A61K 39/39558 |
| WO | 2013/087581 A1 | 6/2013 | |
| WO | 2013/144189 A1 | 10/2013 | |
| WO | 2013/147711 A1 | 10/2013 | |
| WO | 2013/149909 A1 | 10/2013 | |
| WO | 2013/174735 A1 | 11/2013 | |
| WO | 2013/174743 A1 | 11/2013 | |
| WO | 2013/174744 A1 | 11/2013 | |
| WO | 2014/044691 A1 | 3/2014 | |
| WO | 2014/048869 A1 | 4/2014 | |
| WO | 2014/048894 A1 | 4/2014 | |
| WO | 2014/076162 A1 | 5/2014 | |
| WO | 2014/088519 A1 | 6/2014 | |
| WO | 2014/118135 A1 | 8/2014 | |
| WO | 2014/118226 A1 | 8/2014 | |
| WO | 2014/118229 A1 | 8/2014 | |
| WO | 2014/128093 A1 | 8/2014 | |
| WO | 2014/135480 A1 | 9/2014 | |
| WO | 2014/193898 A1 | 12/2014 | |
| WO | 2014/206922 A1 | 12/2014 | |
| WO | 2015/004024 A1 | 1/2015 | |
| WO | 2015/200481 A1 | 12/2015 | |
| WO | 2016/172010 A1 | 10/2016 | |

OTHER PUBLICATIONS

Altman et al. (Jul. 27, 2010) "Negative Regulatory Effects of Mnk Kinases in the Generation of Chemotherapy-Induced Antileukemic Responses", Molecular pharmacology, 78(4):778-784.
Barber et al. (2006) "Restoring Function in Exhausted CD8 T Cells During Chronic Viral Infection", Nature, 439:682-687.
Beggs et al. (Apr. 2015) "The MAP Kinase-Interacting Kinases Regulate Cell Migration, Vimentin Expression and eIF4E/CYFIP1 Binding", Biochemical Journal, 467(1):63-76.
Benson et al. (Sep. 30, 2010) "The PD-1/PD-L1 Axis Modulates the Natural Killer Cell Versus Multiple Myeloma Effect: A Therapeutic Target for CT-011, A Novel Monoclonal Anti-PD-1 Antibody", Blood, 116(13):2286-2294.
Bettini et al. (Dec. 2009) "Regulatory T Cells and Inhibitory Cytokines in Autoimmunity", Current Opinion in Immunology, 21(6):612-618.

(Continued)

*Primary Examiner* — Mark Halvorson
*Assistant Examiner* — Kauser M Akhoon
(74) *Attorney, Agent, or Firm* — Mintz, Levin, Cohn, Ferris, Glovsky and Popeo, P.C.

(57) ABSTRACT

The present disclosure relates to the use MNK-specific inhibitors to inhibit immunosuppression components, such as immune checkpoint proteins PD-1, PD-L1, LAG3, and/or immunosuppressive cytokines, such as IL-10, in order to inhibit or release immune suppression in certain diseases, such as cancer and infectious disease.

23 Claims, 21 Drawing Sheets

(56) References Cited

OTHER PUBLICATIONS

Buxade et al. (Aug. 2005) "The Mnks Are Novel Components in the Control of TNFα Biosynthesis and Phosphorylate and Regulate hnRNP A1", Immunity, 23(2):177-189.
Cavallo et al. (Mar. 2011) "2011: The Immune Hallmarks of Cancer", Cancer Immunology, Immunotherapy, 60(3):319-326.
Chlewicki et al. (2008) "Molecular Basis of the Dual Functions of 2B4 (CD244)", The Journal of Immunology, 180:8159-8167.
Dangaj et al. (May 30, 2013) "Novel Recombinant Human B7-H4 Antibodies Overcome Tumoral Immune Escape to Potentiate T-Cell Antitumor Responses", Cancer Research, 73(15):4820-4829.
Darlington et al. (May 20, 2002) "Surface Cytotoxic T Lymphocyte-associated Antigen 4 Partitions Within Lipid Rafts and Relocates to the Immunological Synapse under Conditions of Inhibition of T Cell Activation", Journal of Experimental Medicine, 195(10):1337-1347.
Diab et al. (Apr. 1, 2014) "MAP Kinase-Interacting Kinases—Emerging Targets against Cancer", Chemistry and Biology, 21(4):441-452.
Duraiswamy et al. (Apr. 30, 2013) "Dual Blockade of PD-1 and CTLA-4 Combined with Tumor Vaccine Effectively Restores T-Cell Rejection Function in Tumors", Cancer Research, 7(12):3591-3603.
Eichbaum (2011) "PD-1 Signaling in HIV and Chronic Viral Infection—Potential for Therapeutic Intervention?", Current Medicinal Chemistry, 18(26):3971-3980.
Francisco et al. (Jul. 2010) "The PD-1 Pathway in Tolerance and Autoimmunity", Immunological Reviews, 236 (1):219-242.
Gandhi et al. (Oct. 1, 2006) "Expression of LAG-3 by Tumor-Infiltrating Lymphocytes is Coincident with the Suppression of Latent Membrane Antigen-Specific CD8+ T-Cell Function in Hodgkin Lymphoma Patients", Blood, 108(7):2280-2289.
Garrido et al. (2010) "Alterations of HLA Class I Expression in Human Melanoma Xenografts in Immunodeficient Mice Occur Frequently and Are Associated with Higher Tumorigenicity", Cancer Immunology, Immunotherapy, 59:13.
Goldberg et al. (Nov. 18, 2010) "LAG-3 in Cancer Immunotherapy", Cancer Immunology and Immunotherapy, 344:269-278.
Grosso et al. (Oct. 11, 2007) "LAG-3 Regulates CD8+ T Cell Accumulation and Effector Function in Murine Self- and Tumor-Tolerance Systems", The Journal of Clinical Investigation, 117(11):3383-3392.
Hanahan et al. (Mar. 4, 2011) "Hallmarks of Cancer: The Next Generation", Cell, 144(5):646-674.
Hanahan et al. (Jan. 7, 2000) "The Hallmarks of Cancer", Cell, 100(1):57-70.
Hannier et al. (Oct. 15, 1998) "CD3/TCR Complex-associated Lymphocyte Activation Gene-3 Molecules Inhibit CD3/TCR Signaling", The Journal of Immunology, 161(8):4058-4065.
Hastings et al. (Sep. 2009) "TIM-3 is Expressed on Activated Human CD4+ T Cells and Regulates Th1 and Th17 Cytokines", European Journal of Immunology, 39(9):2492-2501.
He et al. (2011) "The Inhibitory Role of B7-H4 in Antitumor Immunity: Association with Cancer Progression and Survival", Clinical and Developmental Immunology, Article ID 695834, 2011:8 pages.
Hofmeyer et al. (2011) "The PD-1/PD-L1 (B7-H1) Pathway in Chronic Infection-Induced Cytotoxic T Lymphocyte Exhaustion", Journal of Biomedicine and Biotechnology, Article ID 451694, 2011:9 pages.
Joshi et al. (Jan. 11, 2012) "Mnk Kinases in Cytokine Signaling and Regulation of Cytokine Responses", Biomolecular Concepts, 3(2):127-139.
Karaman et al. (Jan. 8, 2008) "A Quantitative Analysis of Kinase Inhibitor Selectivity", Nature Biotechnology, 26:127-132.
Knauf et al. (2001) "Negative Regulation of Protein Translation by Mitogen-Activated Protein Kinase-Interacting Kinases 1 and 2", Molecular and cellular Biology, 21(16):5500-5511.
Liu et al. (Apr. 29, 2010) "Selective Inhibition of IDO1 Effectively Regulates Mediators of Antitumor Immunity", Blood, 115(17):3520-3530.
Liu et al. (Apr. 1, 2015) "The BRAF and MEK Inhibitors Dabrafenib and Trametinib: Effects on Immune Function and in Combination with Immunomodulatory Antibodies Targeting PD-1, PD-L1, and CTLA-4", Clinical Cancer Research, 21(7):1639-1651.
Liu et al. (2009) "Tumor Regulatory T Cells Potently Abrogate Antitumor Immunity", The Journal of Immunology, 182:6160-6167.
Mahoney et al. (Aug. 2015) "Combination Cancer Immunotherapy and New Immunomodulatory Targets", Nature Reviews Drug Discovery, 14(8):561-584.
Matsuzaki et al. (Apr. 27, 2010) "Tumor-Infiltrating NY-ESO-1-Specific CD8+ T Cells are Negatively Regulated by LAG-3 and PD-1 in Human Ovarian Cancer", PNAS, 107(17):7875-7880.
Mautino et al. (Apr. 2013) "Proceedings: AACR 104th Annual Meeting 2013; Apr. 6-10, 2013", Cancer Research, 73(8).
Mbatia et al. (Jan. 29, 2015) "Novel C-4 Heteroaryl 13-cis-Retinamide Mnk/AR Degrading Agents Inhibit Cell Proliferation and Migration and Induce Apoptosis in Human Breast and Prostate Cancer Cells and Suppress Growth of MDA-MB-231 Human Breast and CWR22Rv1 Human Prostate Tumor Xenograf", Journal of Medicinal Chemistry, 58(4):1900-1914.
Mellor et al. (Oct. 1, 2004) "IDO Expression by Dendritic Cells: Tolerance and Tryptophan Catabolism", Nature Reviews Immunology, 4:762-774.
Mellor (Dec. 9, 2005) "Indoleamine 2,3 Dioxygenase and Regulation of T Cell Immunity", Biochemical and Biophysical Research Communications, 338(1):20-24.
Mosmann et al. (1983) "Rapid Colorimetric Assay for Cellular Growth and Survival: Application to Proliferation and Cytotoxicity Assays", Journal of Immunological Methods, 65:55-63.
Munn (Jun. 2006) "Tumor Immune Evasion Mediated by IDO", Update on Cancer Therapeutics, 1(2):175-185.
Pardoll (Mar. 22, 2012) "The Blockade of Immune Checkpoints in Cancer Immunotherapy", Nature Reviews Cancer, 12(4):252-264.
Rabinovich et al. (Apr. 23, 2007) "Immunosuppressive Strategies that are Mediated by Tumor Cells", Annual Review of Immunology, 25:267-296.
Ramalingam et al. (Jan. 1, 2014) "First MNKs Degrading Agents Block Phosphorylation of eIF4E, Induce Apoptosis, Inhibit Cell Growth, Migration and Invasion in Triple Negative and Her2-Overexpressing Breast Cancer Cell Lines", Oncotarget, 5(2):530-543.
Rodems et al. (Nov. 2002) "A FRET-Based Assay Platform for Ultra-High Density Drug Screening of Protein Kinases and Phosphatases", Assay and Drug Development Technologies, 1(1):9-19.
Rodriguez et al. (Aug. 15, 2004) "Arginase I Production in the Tumor Microenvironment by Mature Myeloid Cells Inhibits T-Cell Receptor Expression and Antigen-Specific T-Cell Responses", Cancer Research, 64:5839-5849.
Rodriguez et al. (Apr. 2008) "Arginine Regulation by Myeloid Derived Suppressor Cells and Tolerance in Cancer: Mechanisms and Therapeutic Perspectives", Immunological Reviews, 222(1):180-191.
Rowlett et al. (Nov. 21, 2007) "MNK Kinases Regulate Multiple TLR Pathways and Innate Proinflammatory Cytokines in Macrophages", AJP Gastrointestinal and Liver Physiology, 294:G452-G459.
Ruffell et al. (Apr. 13, 2015) "Macrophages and Therapeutic Resistance in Cancer", Cancer Cell, 27(4):462-472.
Schabowsky, et al., "Targeting CD4+CD25+FoxP3+ Regulatory T-Cells for the Augmentation of Cancer Immunotherapy", Current opinion in Investigational Drugs, Dec. 2007, 8(12):1002-1008.

(56) References Cited

OTHER PUBLICATIONS

Sfanos, et al., "Phenotypic Analysis of Prostate-Infiltrating Lymphocytes Reveals TH17 and Treg Skewing", Clinical Cancer Research, Jun. 1, 2008, 14(11):3254-3261.
Shui, et al., "Regulation of Inflammation, Autoimmunity, and Infection Immunity by HVEM-BTLA Signaling", Journal of Leukocyte Biology, 2011, 89:517-523.
Schabowsky et al. (Dec. 2007) "Targeting CD4+CD25+FoxP3+ Regulatory T-Cells for the Augmentation of Cancer Immunotherapy", Current opinion in Investigational Drugs, 8(12):1002-1008.
Sfanos et al. (Jun. 1, 2008) "Phenotypic Analysis of Prostate-Infiltrating Lymphocytes Reveals TH17 and Treg Skewing", Clinical Cancer Research, 14(11):3254-3261.
Shui et al. (2011) "Regulation of Inflammation, Autoimmunity, and Infection Immunity by HVEM-BTLA Signaling", Journal of Leukocyte Biology, 89:517-523.
Soliman et al. (Jul.-Aug. 2010) "Indoleamine 2,3-Dioxygenase: Is It an Immune Suppressor?", The Cancer Journal, 16(4):354-359.
Terentis et al. (Dec. 15, 2009) "The Selenazal Drug Ebselen Potently Inhibits Indoleamine 2,3-Dioxygenase by Targeting Enzyme Cysteine Residues", Biochemistry, 49(3):591-600.
Thibult et al. (Feb. 2013) "PD-1 is a Novel Regulator of Human B-Cell Activation", International Immunology, 25(2):129-137.
Tschopp et al. (Apr. 2000) "Phosphorylation of eIF-4E on Ser 209 in Response to Mitogenic and Inflammatory Stimuli is Faithfully Detected by Specific Antibodies", Molecular Cell Biology Research Communications, 3(4):205-211.
Tumeh et al. (Nov. 26, 2014) "PD-1 Blockade Induces Responses by Inhibiting Adaptive Immune Resistance", Nature, 515:568-571.
Wan et al. (Apr. 17, 2009) "Interleukin-1 Receptor-Associated Kinase 2 Is Critical for Lipopolysaccharide-Mediated Post-transcriptional Control", Journal of Biological Chemistry, 284(16):10367-10375.
Wei et al. (Dec. 2013) "Combinatorial PD-1 Blockade and CD137 Activation Has Therapeutic Efficacy in Murine Cancer Models and Synergizes with Cisplatin", Plos One, 8(12):11 pages.
Yi et al. (May 2009) "Fine Tuning the Immune Response Through B7-H3 and B7-H4", Immunological Reviews, 22 (1):145-151.
Zarek et al. (Jan. 1, 2008) "A2A Receptor Signaling Promotes Peripheral Tolerance by Inducing T-Cell Anergy and the Generation of Adaptive Regulatory T Cells", Blood, 111(1):251-259.

\* cited by examiner

INHIBITORS OF IMMUNE CHECKPOINT MODULATORS AND RELATED METHODS

BACKGROUND

T cell mediated immune responses are initiated through antigen recognition by the T cell receptor (TCR). The ultimate amplitude and quality of the T cell response is regulated by immune checkpoints, which control the balance of co-stimulatory and co-inhibitory signals. Immune checkpoints are essential in maintaining self-tolerance and protecting tissues from damage during immune response to infection. However, dysregulated expression of immune checkpoint proteins by tumors provides an important immune resistance mechanism. Inhibitory ligands and receptors that regulate T cell effector functions in tissues are frequently overexpressed on tumor cells or on non-transformed cells in the tumor microenvironment. Two general mechanisms of expression of immune checkpoint ligands on tumor cells have emerged. In some tumors, constitutive oncogenic signaling induces inhibitor ligand expression on the tumor to provide innate immune resistance. Alternatively, an inhibitory ligand may be induced in response to inflammatory signals that are produced by an active anti-tumor immune response (adaptive immune resistance). Preclinical and clinical data indicates that inhibition of immune checkpoints can enhance endogenous anti-tumor immunity (see, e.g., Pardoll, *Nat. Rev. Cancer* 12:252, 2012).

There is a need in the art for alternative, effective modulators of immune checkpoint pathways. The present disclosure meets such needs, and further provides other related advantages.

DETAILED DESCRIPTION

Figure 1A:
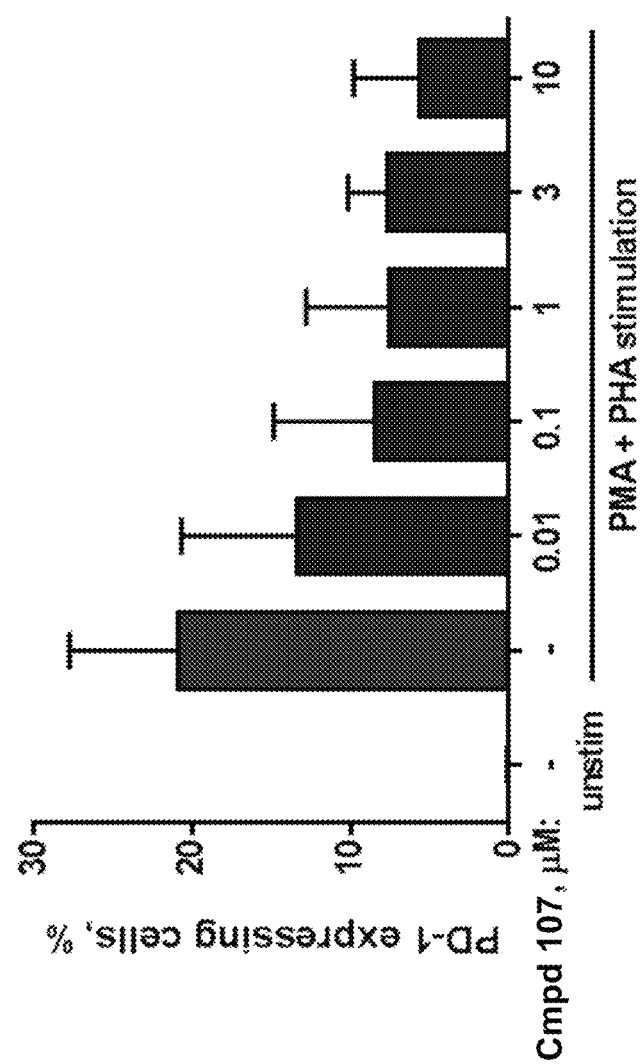
FIGS. 1A to 1D show that MNK-specific inhibitors can block the expression of various immune checkpoint proteins in a transformed T cell line (Jurkat), without affecting cell viability or activation. (A) and (B) As detected by flow cytometry, PD-1 expression is stimulated on Jurkat cells contacted with PHA and PMA, whereas PD-1 expression is reduced in a dose dependent manner by MNK-specific inhibitor Compound 107 (used at 0.01, 0.1, 1, 3 and 10 μM). (C) An ELISA assay detected increased levels of human IL-2 production in Jurkat T cells contacted with PHA and PMA, which indicates that the Jurkat T cells were activated via their TCRs. The presence of MNK-specific inhibitor Compound 107 did not detectably alter IL-2 production, indicating that T cell activation is unaffected by the MNK-specific inhibitor. (D) The viability of Jurkat cells treated with PHA and PMA or with PHA, PMA and Compound 107 as in (A) above was unaffected as determined by the percentage of dead cells detected using fixable dead cell stain (BD Biosciences, San Jose, Calif.).

The present disclosure relates to compositions and methods for immune modulation by, for example, relieving disease-associated immune resistance mediated by induction of immune suppression molecules and reduction in molecules involved in an adaptive immune response. For example, improper levels or activity of immune checkpoint proteins (such as programmed cell death protein 1 (PD-1) or its ligands (PD-L1, PD-L2)), immunosuppressive cytokines (e.g., IL-10), or regulatory T cells may be corrected or normalized through the use of a MAP kinase interacting serine/threonine kinase (MKNK or MNK)-specific inhibitors. On the other hand, such MNK-specific inhibitors may be used to restore or increase expression of major histocompatibility complex (MHC, or HLA in humans) molecules important for antigen presentation to T cells or immune memory.

By way of background, the cell-mediated immune response portion of the human adaptive immune system involves activation of lymphocytes (T cells) to mediate destruction of pathogenic or abnormal cells and related molecules. T cells can be activated by cells presenting a foreign antigen that has originated externally (e.g., invading pathogen) or internally from a cell (e.g., cancer cells). This response is highly regulated through various immune checkpoints since an aberrant response can cause damage to the host. Under normal conditions, the immune checkpoint system is an elaborate series of cellular signals and molecular interactions that prevents excessive activation or effector activity by T cells. But, this balance of positive (co-stimulatory) to negative (suppressive) signaling can be disrupted by non-normal conditions and result in an abnormal microenvironment in which the immune response or immune surveillance is suppressed. Such immune resistance can arise under certain pathogenic conditions, such as cancer or infection.

One exemplary early negative regulator of T cell activation is cytotoxic T lymphocyte antigen-4 (CTLA-4). Activation of cytotoxic T cells results in cell surface expression of CTLA-4, which then competes with co-stimulatory molecule CD28 for their mutually shared ligands, B7-1 (CD80) or B7-2 (CD86) on the antigen-presenting cell (APC). These competing positive and negative signals hold early stage cytotoxic activity in check, while at the same time allowing T cells to continue functioning in a self-limited manner (see, e.g., Teft et al., *Ann. Rev. Immunol.* 24:65, 2006).

An exemplary later inhibitory receptor found on the surface of T cells is PD-1, which can transmit an inhibitory signal when bound by one of its ligands, PD-L1 (B7-H1, CD274) or PD-L2 (B7-DC, CD73), found on APCs. PD-1 limits the effector function of T cells in peripheral tissues during inflammation and helps maintain tolerance (i.e., minimize autoimmunity) (see Francisco et al., *Immunol. Rev.* 236:219, 2010). Further exemplary inhibitory receptors found on the surface of T cells include CD200R, LAG3, BTLA, KIR, SIRPα, TIM3 and A2aR.

The present disclosure describes the surprising ability of MNK-specific inhibitors to mediate or promote a reduction of one or more various immunosuppression components, such as PD-1, PD-L1, LAG3, and IL-10, as well as the ability to modulate the amount of regulatory T cells ($T_{regs}$) and to effectively reduce or minimize suppression of effector T cell ($T_E$) function. In addition, MNK-specific inhibitors are capable of mediating or promoting an increase in expression of major histocompatibility complex (MHC or HLA) class II molecules, which can promote antigen presentation. MNK-specific inhibitors can be used as a viable alternative to, or in combination with, specific inhibitors or modulators of immunosuppression components, such as inhibitors or modulators of immune checkpoint molecules (e.g., anti-PD-1, anti-PD-L1, or anti-CTLA-4 antibodies; see, e.g., Pardol, *Nature Rev. Cancer* 12:252, 2012).

Such a reduction in one or more immunosuppression components (e.g., PD-1, PD-L1, LAG3, IL-10) by administration of a MNK-specific inhibitor, which can also affect other molecules that can reduce or overcome immune suppression activity (e.g., increase MHC/HLA expression), can be used to treat or reduce the progression of disease by, for example, increasing the activity of immune cells (e.g., T cells); reducing the down-modulation of immune cells; inducing or enhancing an immune response; prolonging an immune response; stimulating an antigen-specific T cell response; or the like. For example, a subject (e.g., a human) having a disease-associated with immune resistance (e.g., an immunosuppression component-mediated disease, such as a disease involving dysregulation of PD-1, PD-L1, or LAG3) can be treated with a MNK-specific inhibitor to induce or enhance an immune response in the subject. Exemplary diseases-associated with immune resistance include cancer and infectious disease. In addition, MNK-specific inhibitors can be used in combination with (and even augment) other therapies directed against immunosuppression components, such as antibodies specific for immune checkpoint molecules (e.g., anti-PD-1, anti-PD-L1, anti-LAG3, anti-CTLA-4, kinase inhibitors), to treat diseases in which a non-suppressed (normal, induced or enhanced) immune response would be beneficial.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

"Amino" refers to the —NH$_2$ substituent.
"Aminocarbonyl" refers to the —C(O)NH$_2$ substituent.
"Carboxyl" refers to the —CO$_2$H substituent.
"Carbonyl" refers to a —C(O)— or —C(═O)— group. Both notations are used interchangeably within the specification.
"Cyano" refers to the —C≡N substituent.
"Cyanoalkylene" refers to the -(alkylene)C≡N substituent.
"Acetyl" refers to the —C(O)CH$_3$ substituent.
"Hydroxy" or "hydroxyl" refers to the —OH substituent.
"Hydroxyalkylene" refers to the -(alkylene)OH substituent.
"Oxo" refers to a ═O substituent.
"Thio" or "thiol" refer to a —SH substituent.
"Alkyl" refers to a saturated, straight or branched hydrocarbon chain radical consisting solely of carbon and hydrogen atoms, having from one to twelve carbon atoms ($C_1$-$C_{12}$ alkyl), from one to eight carbon atoms ($C_1$-$C_8$ alkyl) or from one to six carbon atoms ($C_1$-$C_6$ alkyl), and which is attached to the rest of the molecule by a single bond. Exemplary alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like.

"Lower alkyl" has the same meaning as alkyl defined above but having from one to four carbon atoms ($C_1$-$C_4$ alkyl).

"Alkenyl" refers to an unsaturated alkyl group having at least one double bond and from two to twelve carbon atoms ($C_2$-$C_{12}$ alkenyl), from two to eight carbon atoms ($C_2$-$C_8$ alkenyl) or from two to six carbon atoms ($C_2$-$C_6$ alkenyl), and which is attached to the rest of the molecule by a single bond, e.g., ethenyl, propenyl, butenyl, pentenyl, hexenyl, and the like.

"Alkynyl" refers to an unsaturated alkyl group having at least one triple bond and from two to twelve carbon atoms ($C_2$-$C_{12}$ alkynyl), from two to ten carbon atoms ($C_2$-$C_{10}$ alkynyl) from two to eight carbon atoms ($C_2$-$C_8$ alkynyl) or from two to six carbon atoms ($C_2$-$C_6$ alkynyl), and which is attached to the rest of the molecule by a single bond, e.g., ethynyl, propynyl, butynyl, pentynyl, hexynyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkenylene" refers to divalent alkene. Examples of alkenylene include without limitation, ethenylene (—CH=CH—) and all stereoisomeric and conformational isomeric forms thereof "Substituted alkenylene" refers to divalent substituted alkene. "Optionally substituted alkenylene" refers to alkenylene or substituted alkenylene.

"Alkynylene" refers to divalent alkyne. Examples of alkynylene include without limitation, ethynylene, propynylene. "Substituted alkynylene" refers to divalent substituted alkyne.

"Alkoxy" refers to a radical of the formula —$OR_a$ where $R_a$ is an alkyl having the indicated number of carbon atoms as defined above. Examples of alkoxy groups include without limitation —O-methyl (methoxy), —O-ethyl (ethoxy), —O-propyl (propoxy), —O— isopropyl (iso propoxy) and the like.

"Acyl" refers to a radical of the formula —$C(O)R_a$ where $R_a$ is an alkyl having the indicated number of carbon atoms.

"Alkylaminyl" refers to a radical of the formula —$NHR_a$ or —$NR_aR_a$ where each $R_a$ is, independently, an alkyl radical having the indicated number of carbon atoms as defined above.

"Cycloalkylaminyl" refers to a radical of the formula —$NHR_a$ where $R_a$ is a cycloalkyl radical as defined herein.

"Alkylcarbonylaminyl" refers to a radical of the formula —$NHC(O)R_a$, where $R_a$ is an alkyl radical having the indicated number of carbon atoms as defined herein.

"Cycloalkylcarbonylaminyl" refers to a radical of the formula —$NHC(O)R_a$, where $R_a$ is a cycloalkyl radical as defined herein.

"Alkylaminocarbonyl" refers to a radical of the formula —$C(O)NHR_a$ or —$C(O)NR_aR_a$, where each $R_a$ is independently, an alkyl radical having the indicated number of carbon atoms as defined herein.

"Cyclolkylaminocarbonyl" refers to a radical of the formula —$C(O)NHR_a$, where $R_a$ is a cycloalkyl radical as defined herein.

"Aryl" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted aryl" refers to an aryl group or a substituted aryl group.

"Arylene" denotes divalent aryl, and "substituted arylene" refers to divalent substituted aryl.

"Aralkyl" or "araalkylene" may be used interchangeably and refer to a radical of the formula —$R_b$—$R_c$ where $R_b$ is an alkylene chain as defined herein and $R_c$ is one or more aryl radicals as defined herein, for example, benzyl, diphenylmethyl and the like.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Cycloalkylalkylene" or "cycloalkylalkyl" may be used interchangeably and refer to a radical of the formula —$R_bR_e$ where $R_b$ is an alkylene chain as defined herein and $R_e$ is a cycloalkyl radical as defined herein. In certain embodiments, $R_b$ is further substituted with a cycloalkyl group, such that the cycloalkylalkylene comprises two cycloalkyl moieties. Cyclopropylalkylene and cyclobutylalkylene are exemplary cycloalkylalkylene groups, comprising at least one cyclopropyl or at least one cyclobutyl group, respectively.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different. Exemplary haloalkyls are trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl," "heterocycle," or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

"Heterocyclylalkyl" or "heterocyclylalkylene" refers to a radical of the formula —$R_bR_f$ where $R_b$ is an alkylene chain as defined herein and $R_f$ is a heterocyclyl radical as defined above, and if the heterocyclyl is a nitrogen-containing heterocyclyl, the heterocyclyl may be attached to the alkyl radical at the nitrogen atom.

"Heteroaryl" or "heteroarylene" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, 2 carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

"Heteroarylalkyl" or "heteroarylalkylene" refers to a radical of the formula —$R_bR_g$ where $R_b$ is an alkylene chain as defined above and $R_g$ is a heteroaryl radical as defined above.

"Thioalkyl" refers to a radical of the formula —$SR_a$ where $R_a$ is an alkyl radical as defined above containing one to twelve carbon atoms, at least 1-10 carbon atoms, at least 1-8 carbon atoms, at least 1-6 carbon atoms, or at least 1-4 carbon atoms.

"Heterocyclylaminyl" refers to a radical of the formula —$NHR_f$ where $R_f$ is a heterocyclyl radical as defined above.

"Thione" refers to a =S group attached to a carbon atom of a saturated or unsaturated ($C_3$-$C_8$)cyclic or a ($C_1$-$C_8$) acyclic moiety.

"Sulfoxide" refers to a —S(O)— group in which the sulfur atom is covalently attached to two carbon atoms.

"Sulfone" refers to a —$S(O)_2$— group in which a hexavalent sulfur is attached to each of the two oxygen atoms through double bonds and is further attached to two carbon atoms through single covalent bonds.

The term "oxime" refers to a —$C(R_a)$=N—$OR_a$ radical where $R_a$ is hydrogen, lower alkyl, an alkylene or arylene group as defined above.

The compound of the invention can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

As used herein, the term "derivative" refers to a modification of a compound by chemical or biological means, with or without an enzyme, which modified compound is structurally similar to a parent compound and (actually or theoretically) derivable from that parent compound. Generally, a "derivative" differs from an "analog" in that a parent compound may be the starting material to generate a "derivative," whereas the parent compound may not necessarily be used as the starting material to generate an "analog." A derivative may have different chemical, biological or physical properties from the parent compound, such as being more hydrophilic or having altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). Other exemplary derivatizations include glycosylation, alkylation, acylation, acetylation, ubiqutination, esterification, and amidation.

The term "derivative" also refers to all solvates, for example, hydrates or adducts (e.g., adducts with alcohols), active metabolites, and salts of a parent compound. The type of salt depends on the nature of the moieties within the compound. For example, acidic groups, such as carboxylic acid groups, can form alkali metal salts or alkaline earth metal salts (e.g., sodium salts, potassium salts, magnesium salts, calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts with, for example, inorganic acids such as hydrochloric acid, sulfuric acid or phosphoric acid, or with organic carboxylic acids or sulfonic acids such as acetic acid, citric acid, lactic acid, benzoic acid, maleic acid, fumaric acid, tartaric acid, methanesulfonic acid or p-toluenesulfonic acid. Compounds that simultaneously contain a basic group and an acidic group, for example, a carboxyl group in addition to basic nitrogen atoms, can be present as zwitterions. Salts can be obtained by customary methods known to those skilled in the art, for example, by combining a compound with an inorganic or organic acid or base in a solvent or diluent, or from other salts by cation exchange or anion exchange.

The term "prodrug" refers to a precursor of a drug, a compound which upon administration to a patient, must undergo chemical conversion by metabolic processes before becoming an active pharmacological agent. Exemplary prodrugs of compounds in accordance with Formula I are esters, acetamides, and amides.

As used herein, an "immune cell" means any cell of the immune system that originates from a hematopoietic stem cell (e.g., in the bone marrow), which gives rise to two major lineages, a myeloid progenitor cell (which give rise to myeloid cells such as myeloid-derived suppressor cells, monocytes, macrophages, dendritic cells, meagakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4$^-$CD8$^-$ double negative T cell, a γδ T cell, a regulatory T cell, an antigen presenting cell (APC), a natural killer cell, and a dendritic cell. Macrophages, dendritic cells and disease cells (e.g., cancer cells) may be referred to as "antigen presenting cells" or "APCs," which are cells that can activate T cells when a MHC (HLA) receptor complexed with an antigenic peptide on the surface of the APC interacts with a TCR on the surface of a T cell. In certain embodiments, an APC is a cancer cell or tumor cell.

As used herein, the term "immune response" refers to the action of an immune cell, for example, lymphocytes, antigen presenting cells, phagocytic cells, granulocytes, and soluble macromolecules produced by the above cells or the liver (including antibodies, cytokines, and complement), that results in selective damage to, destruction of, or elimination from the human body of invading pathogens, cells or tissues infected with pathogens, cancerous cells, or, in cases of autoimmunity or pathological inflammation, normal human cells or tissues. In certain embodiments, an immune response comprises an antigen-specific T cell response.

The phrase "inducing or enhancing an immune response" refers to causing or stimulating an immune cell (e.g., T cell) to have a sustained or amplified biological function. For example, induced or enhanced T cell responses include increased production of cytokines by CD8$^+$ T cells, increased proliferation, or increased antigen responsiveness relative to the response before intervention. In certain embodiments, the level of enhanced immune cell (e.g., T cell) response after contact with a MNK-specific inhibitor is as least about 25%, 30%, 35%, 40%, 45%, 50%, 55%, 60%, 65%, 70%, 75%, 80%, 85%, 90%, 95%, 99%, or more, as compared to immune cells not contacted with the MNK-specific inhibitor. The assay for detecting cytokine levels (e.g., IL-2, IL-10, IFNγ) to determine whether an immune response induced or enhanced is the multiplex assay described by Dossus et al. (*J. Immunol. Methods* 350:125, 2009). The assay for detecting T cell proliferation to determine whether an immune response induced or enhanced is the assay described by Liu et al. (*Clin. Cancer Res.* 21:1639, 2015). The assay for determining increased antigen responsiveness is the assay described by Tumeh et al. (*Nature* 515:568, 2014).

The phrase "prolonging an immune response" refers to causing or stimulating an immune cell (e.g., T cell) to continue exhibiting a sustained or amplified biological function. In certain embodiments, a prolonged immune response is a measure of antigen specific cytotoxic T cells, of reduced tumor growth or size over time, or of reduced detectable disease after treatment is stopped. For example, tumor size may remain the same or shrink as compared to the tumor size at the start of treatment. In some embodiments, a prolonged immune response can last at least as long as the treatment duration, or at least 1.5-fold, 2.0-fold, 2.5-fold, 3.0-fold, 3.5-fold, 4.0-fold, 4.5-fold, 5.0-fold or more than the treatment duration.

The phrase "reducing the down-modulation" of an immune cell or immune response refers to relieving or releasing an immune cell or immune system from suppression components or signals. For example, a reduced down-modulation may include increased production of cytokines (e.g., IFNγ) by CD8$^+$ T cells, an increase in the number of immune cells (e.g., T cells) in a tumor, an increase in the number of T cell clones in a tumor, an increase in the ratio of $T_E$ cells to $T_{reg}$ cells, or any combination thereof. In certain embodiments, the level of reduced down-modulation of an immune cell (e.g., T cell) or immune response is a reduction in detectable disease (e.g., tumor volume, infectious agents) of at least about 20%, 25%, 30%, 35%, 40%, 45%, 50%, 55%, 60%, 65%, 70%, 75%, 80%, 85%, 90%, 95%, 99%, or more. In other embodiments, the level of reduced down-modulation of an immune cell (e.g., T cell) or immune response is an increase in progression-free survival, which parameters will vary depending on the cancer being treated and which parameters are known to a person of ordinary skill in the art.

"Major histocompatibility complex molecules" (MHC molecules), which is used interchangeably and is understood to also refer to the human counterpart "human leukocyte antigen" (HLA molecules), refer to glycoproteins that deliver peptide antigens to a cell surface. MHC or HLA class I molecules are heterodimers consisting of a membrane spanning a chain (with three α domains) and a non-covalently associated β2 microglobulin. MHC or HLA class II molecules are composed of two transmembrane glycoproteins, α and β, both of which span the membrane. Each chain has two domains. MHC or HLA class I molecules deliver peptides originating in the cytosol to the cell surface, where a peptide:MHC (or peptide:HLA in humans) complex is recognized by CD8$^+$ T cells. A T cell peptide antigen (i.e., containing an epitope recognized by a T cell) complexed with an MHC class I molecule is referred to as an MHC class I epitope. MHC class I epitopes are recognized by T cell receptors (TCRs) and generally are found on peptide antigens having a length ranging from about 8 amino acids to about 11 amino acids. MHC class II molecules deliver peptides originating in the vesicular system to the cell surface, where they are recognized by CD4$^+$ T cell receptors. A T cell peptide antigen presented by an MHC class II molecule is referred to as an MHC class II epitope. MHC class II epitopes generally are found on peptide antigens having a length ranging from about 13 to about 17 amino acids. An MHC molecule may be from various animal species, including human (HLA), mouse, rat, or other mammals.

"T cell receptor" (TCR) refers to a molecule found on the surface of T cells (or T lymphocytes) that, in association with CD3, is generally responsible for recognizing antigens bound to MHC (HLA) molecules. The TCR has a disulfide-linked heterodimer of the highly variable α and β chains (also known as TCRα and TCRβ, respectively) in most T cells. In a subset of T cells, a TCR is made up of a heterodimer of variable γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease*, 3$^{rd}$ Ed., Current Biology Publications, p. 4:33, 1997).

As used herein, the term "antigen-specific T cell response" refers to responses by a T cell having a TCR that specifically binds to a peptide antigen complexed with MHC (HLA) class I or class II. CD8$^+$ effector T cells recognize HLA class I restricted antigenic peptides and are able to directly kill target cells expressing the cognate antigen. CD4$^+$ helper T cells recognize HLA class II restricted antigenic peptides and produce a variety of cytokines that mediate inflammatory and effector immune responses. CD4$^+$ helper T cells also facilitate the activation of CD8$^+$ effector T cells and B cells. Regulatory T cells ($T_{reg}$) are CD4$^+$ T cells that inhibit immune responses and produce inhibitory cytokines, such as TGFβ, IL-10, IL-4, IL-1RA, and IL-35. Non-limiting examples of responses by a T cell upon antigen-specific stimulation include activation, proliferation and cytokine production (e.g., IL-2, IFNγ production).

As used herein, the term "immunosuppression component" refers to one or more cells, proteins, molecules, compounds or complexes providing inhibitory signals to assist in controlling or suppressing an immune response. For example, immunosuppression components include those molecules that partially or totally block immune stimulation; decrease, prevent or delay immune activation; or increase, activate, or up regulate immune suppression. "Controlling or suppressing an immune response," as used herein, means reducing any one or more of antigen presentation, T cell activation, T cell proliferation, T cell effector function, cytokine secretion or production, and target cell lysis. Such modulation, control or suppression can promote or permit the persistence of a hyperproliferative disease or disorder (e.g., cancer, chronic infections).

Exemplary immunosuppression components include immune checkpoint ligands (such as PD-L1, PD-L2, CD80, CD86, B7-H3, B7-H4, HVEM, adenosine, GAL9), immune checkpoint receptors (such as PD-1, CTLA-4, BTLA, KIR, LAG3, TIM3, A2aR), metabolic enzymes (such as arginase, indoleamine 2,3-dioxygenase (IDO)), immunosuppressive cytokines (such as IL-10, IL-4, IL-1RA, IL-35), $T_{reg}$ cells, or any combination thereof. In certain embodiments, an immunosuppression component is an immune checkpoint molecule, which may initiate an immune suppression signal through a ligand-receptor interaction, such as by modulating (e.g., inhibiting) an antigen-specific T cell response. For example, a T cell may express on its surface an immune checkpoint receptor (e.g., PD-1, LAG3) and an antigen presenting cell may express on its surface an immune checkpoint receptor ligand (e.g., PD-L1, MHC/HLA molecule). In further embodiments, an immunosuppression component is a metabolic enzyme that inhibits immune responses through the local depletion of amino acids essential for lymphocyte, particularly T cell, survival and function. In still further embodiments, an immunosuppression component may be a signaling molecule, such as an immunosuppressive cytokine (e.g., IL-10, IL-4, IL-1RA, IL-35). In still further embodiments, an immunosuppression component comprises a CD4$^+$ T$_{reg}$ cell that is capable of inhibiting an immune response, as well as producing or releasing immunosuppressive cytokines (e.g., IL-10, IL-4, IL-13, IL-1RA).

Furthermore, an immunosuppression component (e.g., IL-10) may cause a reduction in the expression or level of a major histocompatibility complex (MHC) or human leukocyte antigen (HLA) molecule, which can in turn reduce antigen presentation and thereby reduce, impede or detectably prevent T cell activation and a corresponding immune response. In certain embodiments, a MNK-specific inhibitor may cause a reduction in amount, or inhibit the activity, of an immunosuppression component, which in turn can result in an increase in MHC/HLA molecule (e.g., class II) expression. Such an increase in MHC/HLA levels due to a reduction or inhibition of the immunosuppression component mediated by a MNK-specific inhibitor can improve antigen presentation or can induce or enhance an immune response as compared to no reduction or inhibition of the immunosuppression component.

The term "immune resistance" refers to the process by which a cell or organism (e.g., a cancer cell, virus-infected cell, bacterial cell, fungus, parasite) resists, minimizes, evades, or avoids recognition or elimination by the immune system. Immune resistance may be due to (a) an increase in immune suppression or tolerance, (b) the ability of a cell or organism to modify activate, increase, enhance, facilitate, potentiate or up-regulate immune suppression or tolerance, or (c) the ability of a cell or organism to promote immunologic ignorance or masking of an antigen expressed by the cell or organism, or any combination thereof. In certain embodiments, immune resistance is associated with a disease or disorder, such as a cancer, a tumor or a chronic infection.

As used herein, "disease-associated immune resistance" means a disease or disorder that co-opts certain immune checkpoint pathways to suppress the immune system and, therefore, the disease or disorder presents with an immune resistance phenotype, particularly against T cells specific for, for example, tumor or infectious disease antigens.

As used herein, the term "MNK," also known as "mitogen-activated protein kinase (MAPK)-interacting serine/threonine kinase" or "MKNK" refers to a kinase that is phosphorylated by the p42 MAP kinases ERK1 and ERK2 and the p38-MAP kinases, triggered in response to growth factors, phorbol esters, and oncogenes such as Ras and Mos, and by stress signaling molecules and cytokines. MNK also refers to a kinase that is phosphorylated by additional MAP kinase(s) affected by interleukin-1 receptor-associated kinase 2 (IRAK2) and IRAK4, which are protein kinases involved in signaling innate immune responses through toll-like receptors (e.g., TLR7) (see, e.g., Wan et al., *J. Biol. Chem.* 284: 10367, 2009). Phosphorylation of MNK proteins stimulates their kinase activity toward eukaryotic initiation factor 4E (eIF4E), which in turn regulates cap-dependent protein translation initiation, as well as regulate engagement of other effector elements, including hnRNPA1 and PSF (PTB (polypyrimidine tract binding protein) associated splicing factor). For example, proteins that bind the regulatory AU-rich elements (AREs) of the 3'-UTR of certain mRNAs (e.g., cytokines) are phosphorylated by MNK. Thus, MNK phosphorylation of proteins can alter the ability of these proteins to bind the 5'- or 3'-UTRs of eukaryotic mRNAs. In particular, reduced MNK mediated phosphorylation of hnRNPA1 decreases its binding to cytokine-ARE (see, e.g., Buxadé et al., *Immunity* 23:177, 2005; Joshi and Platanias, *Biomol. Concepts* 3:127, 2012). MNK is encoded by two different genes, MNK1 and MNK2, which are both subject to alternative splicing. MNK1a and MNK2a represent full length transcripts, while MNK1b and MNK2b are splice variants that lack a MAPK binding domain. Therefore, MNK may refer to MNK1 or variants thereof (such as MNK1a or MNK1b), MNK2 or variants thereof (such as MNK2a or MNK2b), or combinations thereof. In particular embodiments, MNK refers to human MNK.

The terms "modulate," "modulation" or the like refer to the ability of a compound to increase or decrease the function, activity or level of an immunosuppression component, such as immune checkpoint molecules or related cytokines (e.g., PD-1, PDL-1, LAG3, IL-10 or the like). "Modulation," in its various forms, is intended to encompass inhibition, antagonism, partial antagonism, activation, agonism or partial agonism of the activity associated with an immunosuppression component, such as immune checkpoint molecules or immunosuppressive cytokines. For example, a modulation that comprises a decrease or inhibition of activity may be indirectly caused by a reduction in expression of an immunosuppression component, such as an immune checkpoint molecule or immunosuppressive cytokine. The ability of a compound to directly or indirectly modulate an immunosuppression component, such as an immune checkpoint molecule or immunosuppressive cytokine, can be demonstrated in biochemical and cell-based assays known in the art (see, e.g., Examples 1-3).

The term "inhibit" or "inhibitor" refers to an alteration, interference, reduction, down regulation, blocking, suppression, abrogation or degradation, directly or indirectly, in the expression, amount or activity of a target or signaling pathway relative to (1) a control, endogenous or reference target or pathway, or (2) the absence of a target or pathway, wherein the alteration, interference, reduction, down regulation, blocking, suppression, abrogation or degradation is statistically, biologically, or clinically significant.

For example, a "MNK inhibitor" may block, inactivate, reduce or minimize MNK activity (e.g., kinase activity or translational effects), or reduce activity by promoting degradation of MNK, by about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or more as compared to untreated MNK. In certain embodiments, a MNK inhibitor blocks, inactivates, reduces or minimizes the ability of MNK to phosphorylate eIF4E, hnRNPA1, PSF or combinations thereof. In further embodiments, a MNK inhibitor reduces or minimizes the expression of an immunosuppression component, such as a ligand on a tumor cell or APC (e.g., PD-L1), a receptor on a T cell (e.g., PD-1, LAG3), or an immunosuppressive cytokine produced by such cells (e.g., IL-10, IL-4, IL-1RA, IL-35). Non-limiting examples of inhibitors include small molecules, antisense molecules, ribozymes, RNAi molecules, or the like.

As used herein, a "MNK-specific inhibitor" is a compound that (a) inhibits MNK enzyme (kinase) activity, (b) has at least about 25-fold less activity against the rest of a host cell kinome (i.e., other than MNK enzymes), and (c) does not significantly reduce or inhibit IL-2 production by T cells. As used herein, "a host cell kinome" refers to the 412 protein and lipid kinases listed in Table A (not including MNK enzymes), which may be from a particular organism or cell of interest (e.g., human). The FRET-based assay for determining whether a particular MNK inhibitor is a MNK-specific inhibitor is performed on the host cell kinome using the method of Rodems et al. (*Assay. Drug Dev. Technol.* 1:9, 2002).

In certain embodiments, the host cell kinome of Table A is from a human cell. In further embodiments, a MNK-specific inhibitor is a small molecule and has at least 50-fold less activity against a serine/threonine kinome of an organism or cell as listed in Table A, and does not significantly reduce or inhibit IL-2 production by T cells. In particular embodiments, the serine/threonine kinome of Table A is from a human cell. In still further embodiments, a MNK-specific inhibitor has at least about 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold less, 200-fold less, 250-fold less, 300-fold less, 400-fold less, 500-fold less, 750-fold less, 1000-fold less, or even less activity against kinome enzymes of Table A other than the serine/threonine kinome enzymes of Table A, and does not significantly reduce or inhibit IL-2 production by T cells.

TABLE A

Protein and Lipid Kinases of "Host Cell Kinome" (excluding MNK) Kinome Kinases

| | | | |
|---|---|---|---|
| STK17A (DRAK1) | CAMK2D (CaMKIIδ) | STK4 (MST1) | MATK (HYL) |
| CLK4 | MAP2K1 (MEK1) S218D S222D | ABL2 (Arg) | PAK2 (PAK65) |
| LRRK2 G2019S | KIT T670I | EPHB1 | MAP2K2 (MEK2) |
| LRRK2 R1441C | SNF1LK2 | MAP3K2 (MEKK2) | HIPK1 (Myak) |
| LRRK2 G2019S FL | LATS2 | PDK1 Direct | PRKX |
| FLT3 D835Y | MAPK3 (ERK1) | PRKCQ (PKC theta) | MAP2K6 (MKK6) S207E T211E |
| TGFBR2 | TLK2 | DDR2 T654M | SIK1 |
| PDGFRA V561D | PI4KB (PI4Kβ) | CSNK2A1 (CK2α1) | CDK2/cyclin A1 |
| LRRK2 FL | RAF1 (cRAF) Y340D Y341D | PRKCG (PKCγ) | EPHB3 |
| LRRK2 | MAPK14 (p38α) | EGFR (ErbB1) d746-750 | EIF2AK2 (PKR) |
| BRSK1 (SAD1) | NTRK3 (TRKC) | PRKCI (PKC iota) | SGK (SGK1) |
| STK17B (DRAK2) | EEF2K | RET V804M | GRK5 |
| RIPK2 | RPS6KA5 (MSK1) | AXL | CAMK2B (CaMKIIβ) |
| TNIK | CSF1R (FMS) | PLK1 | ALK C1156Y |
| LRRK2 I2020T | CSNK1D (CK1δ) | CHEK1 (CHK1) | JAK3 |
| KDR (VEGFR2) | ABL1 M351T | STK32C (YANK3) | MYLK (MLCK) |
| PDGFRA D842V | CSNK1G3 (CK1γ3) | HIPK2 | TAOK3 (JIK) |
| KIT D816V | ACVR1 (ALK2) R206H | TEK (TIE2) Y1108F | MAP2K3 (MEK3) |
| KIT A829P | BRAF | MST1R (RON) | WNK3 |
| RET | CDC7/DBF4 | ULK1 | KIT V654A |
| DYRK3 | MAPK13 (p38δ) | PRKCH (PKC eta) | GRK7 |
| DYRK2 | CDC42 BPA (MRCKA) | STK22D (TSSK1) | CSNK1A1 (CK1 α 1) |
| RPS6KA6 (RSK4) | KIT N822K | FGFR3 G697C | CDK9 (Inactive) |
| MINK1 | CAMK1D (CaMKIδ) | LIMK1 | EGFR (ErbB1) T790M |
| MAP3K8 (COT) | MAP2K6 (MKK6) | STK22B (TSSK2) | TEC |
| RET Y791F | PIK3CD/PIK3R1 (p110δ/p85α) | MAP3K10 (MLK2) | MAP4K3 (GLK) |
| BRAF V599E | CLK3 | MAPK10 (JNK3) | MAP3K14 (NIK) |
| RET V804L | EPHA2 | PHKG1 | AMPK (A2/B2/G1) |
| BMPR2 | MAPKAPK3 | NLK | TYK2 |
| PRKG2 (PKG2) | MST4 | KIT | JAK1 |
| MAPK9 (JNK2) | STK25 (YSK1) | BRAF | ACVRL1 (ALK1) |
| KIT D816H | FGFR1 | MAP4K2 (GCK) | MAP4K4 (HGK) |
| PRKD1 (PKC mu) | CSNK1E (CK1ζ) | PIK3CG (p110γ) | DMPK |
| DYRK1A | TYRO3 (RSE) | MET M1250T | MAPK9 (JNK2) |
| CAMK4 (CaMKIV) | FLT3 ITD | CSNK2A2 (CK2α2) | TNK2 (ACK) |
| STK24 (MST3) | PLK2 | TAOK1 | PKN2 (PRK2) |
| PAK7 (KIAA1264) | EPHA7 | ABL1 | PRKG1 |
| AURKC (Aurora C) | CDK1/cyclin B | CDK2/cyclin A2 | LTK (TYK1) |
| ZAP70 | AKT2 (PKBβ) | TEK (TIE2) R849W | CDK7/cyclin H/MNAT1 |
| MAP2K2 (MEK2) | CDK5/p35 | NUAK1 (ARK5) | ACVR1 (ALK2) |
| PRKCN (PKD3) | SRPK2 | ABL1 G250E | BMPR1A (ALK3) |
| FLT3 | INSR | PAK6 | DDR1 |
| STK39 (STLK3) | MAP2K6 (MKK6) | CDC42 BPB (MRCKB) | ERBB4 (HER4) |
| RET G691S | MARK2 | CDK9/cyclin K | CDK16 (PCTK1)/cyclin Y |
| AURKB (Aurora B) | CLK1 | CAMK2A (CaMKIIα) | AMPK (A1/B1/G2) |

TABLE A-continued

Protein and Lipid Kinases of "Host Cell Kinome" (excluding MNK)
Kinome Kinases

| | | | |
|---|---|---|---|
| GSK3A (GSK3α) | GSG2 (Haspin) | JAK2 JH1 JH2 V617F | MAP2K1 (MEK1) |
| MAPK8 (JNK1) | EPHA4 | CASK | EGFR (ErbB1) L858R |
| SRMS (Srm) | MAPK12 (p38γ) | ACVR2A | PTK6 (Brk) |
| PAK3 | TXK | ALK L1196M | NUAK2 |
| MAPK11 (p38β) | ABL1 Q252H | TTK | STK38L (NDR2) |
| DYRK1B | PASK | DYRK4 | ADRBK2 (GRK3) |
| DNA-PK | GRK4 | WNK2 | MAPK15 (ERK7) |
| IGF1R | FGFR3 | FLT1 (VEGFR1) | ACVR2B |
| PTK2 (FAK) | DAPK2 | PAK1 | MAP3K11 (MLK3) |
| FER | STK23 (MSSK1) | LCK | AXL R499C |
| CSNK1G1 (CK1γ1) | STK3 (MST2) | SRPK1 | PKN1 (PRK1) |
| DDR2 N456S | BRAF V599E | PHKG2 | CDK3/cyclin E1 |
| EPHA5 | AMPK A1/B1/G1 | BMPR1B (ALK6) | MAP4K1 (HPK1) |
| FGFR4 | EGFR (ErbB1) L861Q | BLK | CAMK2G (CaMKIIγ) |
| FGR | AKT1 (PKBα) | MARK4 | MET D1228H |
| SRC | CLK2 | PRKCB1 (PKCβ I) | WEE1 |
| MLCK (MLCK2) | ABL1 T315I | ALK F1174L | ROCK1 |
| MAPK10 (JNK3) | GRK6 | FGFR3 K650E | EPHA3 |
| MAPKAPK2 | EPHA1 | MERTK (cMER) A708S | STK32B (YANK2) |
| PRKD2 (PKD2) | HCK | MAP3K3 (MEKK3) | KIT Y823D |
| FRK (PTK5) | SGK2 | FGFR1 V561M | EGFR (ErbB1) T790M L858R |
| PDGFRA T674I | ULK2 | CDK11 (Inactive) | TAOK2 (TAO1) |
| SRC N1 | CDK5/p25 | MAP3K9 (MLK1) | IKBKE (IKKζ) |
| ROCK2 | KIT D820E | FES (FPS) | NEK9 |
| BMX | MUSK | ITK | MAPK8 (JNK1) |
| CDK2/cyclin O | PRKCA (PKCα) | ZAK | BTK |
| TBK1 | AURKA (Aurora A) | KIT T670E | AMPK (A1/B1/G3) |
| CSK | PRKACA (PKA) | ALK R1275Q | SIK3 |
| CDK1/cyclin A2 | NEK4 | LIMK2 | PIK3C3 (hVPS34) |
| HIPK4 | EPHA6 | ABL1 E255K | PIM1 |
| AMPK A2/B1/G1 | CDK8/cyclin C | MELK | FLT4 (VEGFR3) |
| EPHA8 | JAK2 JH1 JH2 | NEK2 | CDK2/cyclin E1 |
| AKT3 (PKBγ) | ALK | SLK | SPHK1 |
| YES1 | CAMKK1 (CAMKKA) | MERTK (cMER) | PDK1 |
| MARK3 | EPHB2 | MAP2K1 (MEK1) | EGFR (ErbB1) |
| MAPK14 (p38α) Direct | HIPK3 (YAK1) | DDR2 | RET M918T |
| RAF1 (cRAF) Y340D Y341D | FGFR3 K650M | INSRR (IRR) | MAP4K5 (KHS1) |
| IRAK4 | NTRK1 (TRKA) | TEK (Tie2) | FYN A |
| PRKCZ (PKCζ) | STK33 | MARK1 (MARK) | LATS1 |
| RPS6KA1 (RSK1) | CSNK1G2 (CK1γ2) | TLK1 | RPS6KB1 (p70S6K) |
| CAMK1 (CaMK1) | DAPK3 (ZIPK) | AMPK (A1/B2/G1) | PDGFRB (PDGFRβ) |
| PDGFRA (PDGFRα) | ABL1 Y253F | EPHB4 | PRKACG (PRKACγ) |
| RPS6KA2 (RSK3) | ROS1 | ULK3 | PLK3 |
| GSK3B (GSK3β) | MAP3K5 (ASK1) | ABL1 H396P | BRSK2 |
| PAK4 | NEK6 | CDK9/cyclin T1 | TGFBR1 (ALK5) |
| TESK2 | STK38 (NDR) | SYK | PRKCE (PKCε) |
| NEK1 | IKBKB (IKKβ) | CHEK2 (CHK2) | MAP3K7/MAP3K7IP1 (TAK1-TAB1) |
| DCAMKL2 (DCK2) | PRKACB (PRKACβ) | JAK2 | NEK7 |
| SGKL (SGK3) | MYLK2 (skMLCK) | STK16 (PKL12) | MET (cMet) |
| PIK3C2B (PI3K-C2β) | PRKCB2 (PKCβII) | PLK4 | GRK1 |
| CHUK (IKKα) | PIM2 | ADRBK1 (GRK2) | PIK3CA/PIK3R1 (p110α/p85α) |
| NTRK2 (TRKB) | CAMKK2 (CaMKKβ) | AMPK (A2/B2/G2) | PIK3C2A (PI3K-C2α) |
| ACVR1B (ALK4) | FRAP1 (mTOR) | MAPK1 (ERK2) | SPHK2 |
| RPS6KA3 (RSK2) | ICK | MYO3B (MYO3β) | PI4KA (PI4Kα) |
| PTK2B (FAK2) | LYN A | CDK14 (PFTK1)/cyclin Y | RIPK3 |
| RPS6KA4 (MSK2) | CDK2/cyclin A | DAPK1 | CDK5 (Inactive) |
| FYN | KIT V559D T670I | FGFR2 | IRAK1 |
| LYN B | MAPKAPK5 (PRAK) | ERBB2 (HER2) | PRKCD (PKCδ) |

In any of the aforementioned embodiments, a MNK-specific inhibitor can further block, inactivate, reduce or minimize the ability of MNK1a, MNK1b, MNK2a, MNK2b, or any combination thereof to phosphorylate eIF4E, hnRNPA1, PSF or any combination thereof. MNK-specific inhibitors in any of the aforementioned embodiments may optionally not significantly reduce or inhibit (i) T cell viability, (ii) T cell proliferation, (iii) expression of WIC or HLA molecules in APCs, or (iv) production of IL-2, CD25, IFNγ or any combination thereof by T cells. Further, optionally, MNK-specific inhibitors in any of the aforementioned embodiments can also significantly reduce or inhibit expression of one or more immunosuppression components (e.g., immune checkpoint molecules, immunosuppressive cytokines) in T cells, APCs or both. The assay for measuring T cell viability is the assay described by Mosmann (*J. Immunol. Meth.* 65:55, 1983)

With regard to a MNK-specific inhibitor, "does not significantly reduce or inhibit IL-2 production by T cells" means the reduction or inhibition of IL-2 production by T cells is less than about 25%, 20%, 15%, 10%, 5%, 2%, 1%, 0.5%, 0.25%, 0.1% or less as compared to the same T cells not exposed or contacted with the MNK-specific inhibitor.

Also with regard to a MNK-specific inhibitor, "does not significantly reduce or inhibit T cells viability," "does not significantly reduce or inhibit T cell proliferation," "does not significantly reduce or inhibit MHC or HLA molecule expression in T cells, APCs or both," and "does not significantly reduce or inhibit production of IL-2, CD25, IFNγ or any combination thereof by T cells," refers to the reduction or inhibition of T cell viability; T cell proliferation; expression of WIC or HLA molecules in T cells, APCs or both; or production of IL-2, CD25, IFNγ or any combination thereof by T cells; respectively, is less than about 25%, 20%, 15%, 10%, 5%, 2%, 1%, 0.5%, 0.25%, 0.1% or less as compared to the same corresponding cells not exposed or contacted with the MNK-specific inhibitor.

Also, with regard to a MNK-specific inhibitor, "significantly reduce or inhibit expression of one or more immunosuppression components" means the reduction or inhibition of expression of one or more immunosuppression components in T cells, APCs or both is at least about 20%, 25%, 30%, 35%, 40%, 45%, 50%, 55%, 60%, 65%, 70% or 75% as compared to the same T cells or APCs not exposed or contacted with the MNK-specific inhibitor. In certain embodiments, an APC is a cancer cell or a tumor cell.

Other assays for detecting kinase activity in the presence or absence of inhibitors are well known in the art, which can be used as a back-up to the FRET-based host cell kinome assay to show a particular MNK inhibitor is a MNK-specific inhibitor, such as the assay taught by Karaman et al. (*Nat. Biotechnol.* 26:127, 2007). Assays for detecting the cytokine levels (e.g., IL-2, IL-10, IFNγ) are known in the art, such as the DuoSet® ELISA assay from R&D Systems (using the manufacturer's instructions). Assays for detecting T cell viability, T cell proliferation, MHC or HLA molecule expression, and expression of immunosuppression components like immune checkpoint molecules PD-1, PD-L1, LAG3 or the like are those described in Examples 1-3.

Altering Immunomodulatory Activity

Innate immunity is the first line of defense against invading pathogens and is made up of resident immune effector cells, including macrophages, monocytes, eiosinophils, basophils, and natural killer cells (Medzhitov and Janeway, *N. Engl. J. Med.* 343:338, 2000; Vivier et al., *Science* 331:44, 2011). But, adaptive immunity is what provides specificity to the immune response in higher eukaryotes.

Antigens are presented to T cells through Major Histocompatability Complex (MHC) Class I (MHC-I) or Class II (MHC-II) molecules (Braciale et al., *Immunol. Rev.* 98:95, 1987). MHC class II genes encode cell surface glycoproteins involved in the binding and presentation of peptides to CD4$^+$ T cells. These genes encode the polymorphic HLA-DR, -DQ, and -DP molecules, which are expressed on the cell surface as α- and β-chain heterodimers. MHC class II molecules are central to the initiation of cellular and humoral immune responses. But, to ensure immune system remains in check once an antigen is cleared, regulatory T cells ($T_{regs}$, which are CD25$^+$CD4$^+$Foxp3$^+$) are induced to actively engage in the maintenance of immunological self-tolerance and immune homeostasis. A tumor microenvironment can be unique in that increased expression of immune suppression molecules (e.g., PD-1, CTLA4, LAG3, IL-10, TGF-β) may allow cells in that environment to escape immune surveillance. Moreover, recent evidence indicates that suppression of MHC class I and class II expression on multiple tumor types may also play a role in tumor immunoevasion (Garrido et al., *Cancer Immunol. Immunother.* 59:13, 2010).

Certain MNK inhibitor compounds of this disclosure are potent and selective inhibitors of MNK1 and MNK2 (e.g., compounds of Formula I, Ia, IIa, IIb, IIIa, IIIb, IVa, IVb, Va, Vb, VI, VIIa or VIIb, including Compound 107). MNK1 and MNK2 integrate signals from several oncogenic and immune signaling pathways by phosphorylating eukaryotic initiation factor 4E (eIF4E) and other mRNA binding proteins, which regulate the stability and translation of select mRNAs important for tumor growth and survival.

The present disclosure provides methods of reducing the level or activity of PD-1, PD-L1, LAG3 or IL-10, altering the ratio of T effector ($T_E$) cells to T regulatory ($T_{reg}$) cells, inducing the expression of a MHC or HLA class II molecule, or any combination thereof, by the use of MNK-specific inhibitors, which unexpectedly reduce or downregulate the expression of various immunosuppression components, such as immune checkpoint proteins, including PD-1, PD-L1 and LAG3, as well as related immunosuppressive cytokines (such as IL-10, IL-4, IL-1RA, IL-35). In addition, MNK-specific inhibitors of this disclosure can induce the expression of MHC or HLA class II molecules. In further embodiments, a MNK-specific inhibitor reduces the level of PD-1, LAG3 or both in a cell, and optionally blocks or reduces the ability of a MNK kinase to phosphorylate eIF4E, hnRNPA1, PSF or any combination thereof, and further optionally blocks or reduces the production of immunosuppressive cytokines (e.g., IL-10, IL-4, IL-1RA, IL-35). In still further embodiments, a MNK-specific inhibitor reduces the level of PD-L1 in a cell, and blocks or reduces the ability of a MNK kinase to phosphorylate eIF4E, hnRNPA1, PSF or any combination thereof.

MNK-specific inhibitors of this disclosure can be used in combination with other kinase inhibitors (some of which may also non-specifically inhibit MNK activity, referred to herein as "another kinase inhibitor" or "non-specific MNK inhibitor"). In certain embodiments, another kinase or non-specific MNK inhibitor is an agent that reduces or inhibits the MNK kinase activity, directly or indirectly, so that its substrate, eIF4E, is not efficiently or substantially phosphorylated by MNK. In particular embodiments, another kinase or non-specific MNK inhibitor is an agent that degrades MNK (e.g., via ubiquitin-dependent degradation).

A MNK-specific inhibitor can be administered to a subject in need of immune modulation (e.g., a subject having a cancer or an infection). Exemplary methods of immune modulation comprise increasing in the activity of an immune cell; reducing the down-modulation of an immune cell; inducing or enhancing an immune response; prolonging an immune response; stimulating an antigen-specific T cell response; inhibiting an immunosuppressive signaling pathway; promoting endogenous immunity (e.g., pre-existing or de novo, such as anti-cancer); enhancing a vaccine-induced immune response; or inhibiting disease-associated immune resistance (e.g., cancer, infection), as described herein.

Exemplary MNK-specific inhibitors can inhibit both MNK1 and MNK2 kinase activity. In certain embodiments, a MNK-specific inhibitor selectively inhibits MNK1 kinase activity over MNK2 kinase activity, or selectively inhibits MNK2 kinase activity over MNK1 kinase activity. In other embodiments, a MNK-specific inhibitor selectively inhibits kinase activity of full length isoforms MNK1a and MNK2a over the kinase activity of MNK1b and MNK2b. In further embodiments, a MNK-specific inhibitor selectively inhibits either MNK1 kinase activity or MNK2 kinase activity. In still further embodiments, a MNK-specific inhibitor selectively inhibits kinase activity of any one of full length isoforms MNK1a, MNK1b, MNK2a, or MNK2b, or inhibits the kinase activity of all the MNK isoforms.

In further embodiments, a MNK-specific inhibitor may be a compound, antisense molecule, ribozyme, RNAi molecule, or low molecular weight organic molecule.

In certain embodiments, a MNK-specific inhibitor is a compound having the following structure (I):

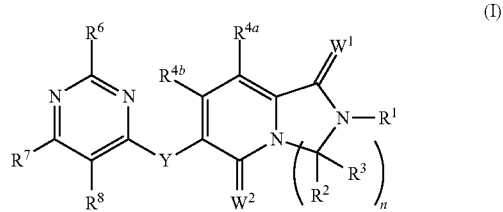

(I)

or a stereoisomer, tautomer or pharmaceutically acceptable salt thereof wherein:

$W^1$ and $W^2$ are independently O, S or N—OR', where R' is lower alkyl;

Y is —N($R^5$)—, —O—, —S—, —C(O)—, —S=O, —S(O)$_2$—, or —CHR$^9$—;

$R^1$ is hydrogen, lower alkyl, cycloalkyl or heterocyclyl wherein any lower alkyl, cycloalkyl or heterocyclyl is optionally substituted with 1, 2 or 3 J groups;

n is 1, 2 or 3;

$R^2$ and $R^3$ are each independently hydrogen, alkyl, alkenyl, alkynyl, aryl, araalkylene, heteroaryl, heteroarylalkylene, cycloalkyl, cycloalkylalkylene, heterocyclyl, or heterocyclylalkylene, wherein any alkyl, aryl, araalkylene, heteroaryl, heteroarylalkylene, cycloalkyl, cycloalkylalkylene, heterocyclyl, or heterocyclylalkylene, is optionally substituted with 1, 2 or 3 J groups;

or $R^2$ and $R^3$ taken together with the carbon atom to which they are attached form a cycloalkyl or heterocyclyl, wherein any cycloalkyl or heterocyclyl is optionally substituted with 1, 2 or 3 J groups;

$R^{4a}$ and $R^{4b}$ are each independently hydrogen, halogen, hydroxyl, thiol, hydroxyalkylene, cyano, alkyl, alkoxy, acyl, thioalkyl, alkenyl, alkynyl, cycloalkyl, aryl, or heterocyclyl;

$R^5$ is hydrogen, cyano, or lower alkyl;

or $R^5$ and $R^8$ taken together with the atoms to which they are attached form a fused heterocyclyl optionally substituted with 1, 2 or 3 J groups;

$R^6$, $R^7$ and $R^8$ are each independently hydrogen, hydroxy, halogen, cyano, amino, alkyl, alkenyl, alkynyl, alkoxy, cycloalkyl, cycloalkylalkylene, cycloalkylalkenylene, alkylaminyl, alkylcarbonylaminyl, cycloalkylcarbonylaminyl, cycloalkylaminyl, heterocyclylaminyl, heteroaryl, or heterocyclyl, and wherein any amino, alkyl, alkenyl, alkynyl, alkoxy, cycloalkyl, cycloalkylalkylene, cycloalkylalkenylene, amino, alkylaminyl, alkylcarbonylaminyl, cycloalkylcarbonylaminyl, cycloalkylaminyl, heterocyclylaminyl, heteroaryl, or heterocyclyl is optionally substituted with 1, 2 or 3 J groups;

or $R^7$ and $R^8$ taken together with the atoms to which they are attached form a fused heterocyclyl or heteroaryl optionally substituted with 1, 2 or 3 J groups;

J is —SH, —SR$^9$, —S(O)R$^9$, —S(O)$_2$R$^9$, —S(O)NH$_2$, —S(O)NR$^9$R$^9$, —NH$_2$, —NR$^9$R$^9$, —COOH, —C(O)OR$^9$, —C(O)R$^9$, —C(O)—NH$_2$, —C(O)—NR$^9$R$^9$, hydroxy, cyano, halogen, acetyl, alkyl, lower alkyl, alkenyl, alkynyl, alkoxy, haloalkyl, thioalkyl, cyanoalkylene, alkylaminyl, NH$_2$—C(O)-alkylene, NR$^9$R$^9$—C(O)-alkylene, —CHR$^9$—C(O)-lower alkyl, —C(O)— lower alkyl, alkylcarbonylaminyl, cycloalkyl, cycloalkylalkylene, cycloalkylalkenylene, cycloalkylcarbonylaminyl, cycloalkylaminyl, —CHR$^9$—C(O)-cycloalkyl, —C(O)-cycloalkyl, —CHR$^9$—C(O)-aryl, —CHR$^9$-aryl, —C(O)-aryl, —CHR$^9$—C(O)-heterocyloalkyl, —C(O)-heterocycloalkyl, heterocyclylaminyl, or heterocyclyl; or any two J groups bound to the same carbon or hetero atom may be taken together to form oxo; and $R^9$ is hydrogen, lower alkyl or —OH.

In one embodiment of structure (I), the present disclosure provides a compound having the following structure (Ia), as well as stereoisomers, tautomers or pharmaceutically acceptable salts thereof.

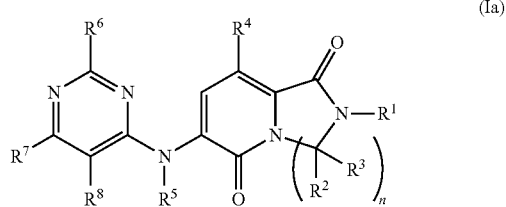

(Ia)

For Formula Ia compounds, substituent $R^1$ is hydrogen or lower alkyl and subscript n is 1, 2 or 3. Substituents $R^2$ and $R^3$ in Formula Ia are each independently hydrogen, alkyl, cycloalkyl, cycloalkylalkylene, heterocyclyl or heterocyclylalkyl, and any such alkyl, cycloalkyl, cycloalkylalkylene, heterocyclyl or heterocyclylalkyl can optionally be substituted with 1, 2 or 3 J groups.

Substitutents $R^2$ and $R^3$ in Formula Ia when taken together with the carbon atom to which they are attached can form a cycloalkyl or heterocyclyl, wherein any such cycloalkyl or heterocyclyl is optionally substituted with 1, 2 or 3 J groups. In Formula Ia, $R^{4a}$ is hydrogen, halogen, hydroxy, alkyl, alkoxy, thioalkyl, alkenyl or cycloalkyl and substituent $R^5$ is hydrogen or lower alkyl.

Alternatively, substituent groups R⁵ and R⁸ taken together with the atoms to which they are attached form a fused heterocyclyl that is optionally substituted with 1, 2 or 3 J groups.

In one embodiment, substituents R⁶, R⁷ and R⁸ are independently and at each occurrence hydrogen, halogen, alkyl, alkenyl, cycloalkly, cycloalkylalkyl, cycloalkylalkenyl, amino, alkylaminyl, alklycarbonylaminyl, cycloalkylcarbonylaminyl, alkylaminyl or cycloalkylaminyl, and any such alkyl, alkenyl, cycloalkly, cycloalkylalkyl, cycloalkylalkenyl, amino, alkylaminyl, alklycarbonylaminyl, cycloalkylcarbonylaminyl, alkylaminyl or cycloalkylaminyl is optionally substituted with 1, 2 or 3 J groups. For some compounds in accordance with Formula Ia, R⁷ and R⁸ taken together with the atoms to which they are attached form a fused heterocyclyl unsubstituted or substituted with 1, 2 or 3 J groups.

Variable J in Formula Ia is —SH, —SR⁹, —S(O)R⁹, —S(O)₂R⁹, —S(O)NH₂, —S(O)NR⁹R⁹, —NH₂, —NR⁹R⁹, —COOH, —C(O)OR⁹, —C(O)R⁹, —C(O)—NH₂, —C(O)—NR⁹R⁹, hydroxy, cyano, halogen, acetyl, alkyl, lower alkyl, alkenyl, alkynyl, alkoxy, haloalkyl, thioalkyl, cyanoalkylene, alkylaminyl, NH₂—C(O)-alkylene, NR⁹R⁹—C(O)-alkylene, —CHR⁹—C(O)-lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —CHR⁹—C(O)-cycloalkyl, —C(O)-cycloalkyl, —CHR⁹—C(O)-aryl, —CHR⁹-aryl, —C(O)-aryl, —CHR⁹—C(O)-heterocycloalkyl, —C(O)-heterocycloalkyl, heterocyclylaminyl, or heterocyclyl. For some of the inventive compounds according to Formula Ia, any two J groups bound to the same carbon or hetero atom may be taken together to form an oxo group.

In some embodiments, variable J in Formula Ia is halogen, amino, alkyl, haloalkyl, alkylaminyl, cycloalkyl or heterocyclyl. Alternatively, for certain Formula Ia compounds, any two J groups when bound to the same carbon or hetero atom may be taken together to form oxo group.

Further MNK-specific inhibitors are compounds according to Formula IIa, illustrated below, where variable Y is —N(R⁵)— and subscript "n" is 1.

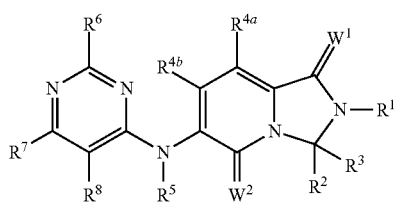

(IIa)

According to one embodiment, variable Y in Formula I is —O—, —S—, —C(O)—, sulfoxide, sulfone, —CHR⁹— or —CH₂—, subscript "n" is 1 and the inventive compounds conform to Formula IIb. When "Y" is —CHR⁹— in Formula IIb, substituent R⁹ is hydrogen, lower alkyl or hydroxy.

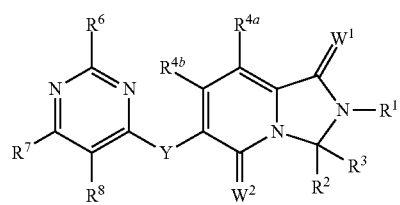

(IIb)

In more MNK-specific inhibitor embodiments, variable "Y" in Formula I is —N(R⁵)—, subscript "n" is 2 or 3 and the compounds conform to Formula IIIa or Formula IVa, respectively:

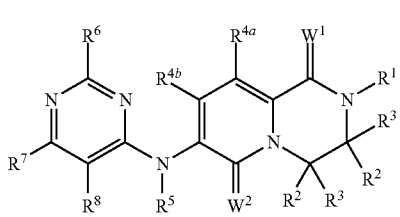

(IIIa)

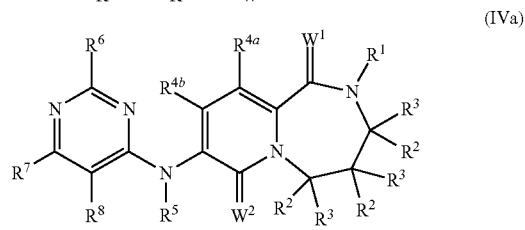

(IVa)

Alternatively, in certain embodiments, variable "Y" in Formula I is —O—, —S—, —C(O)—, sulfoxide, sulfone, —CHR⁹— or —CH₂—, "n" is 2 or 3 and the compounds conform to Formula IIIb and Formula IVb, respectively: When "Y" is —CHR⁹— in Formula IIIb or Formula IVb, substituent R⁹ is either hydrogen, lower alkyl or hydroxy.

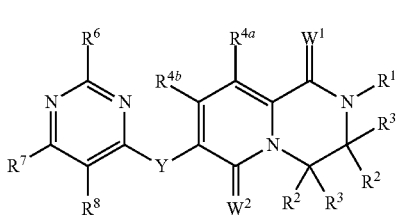

(IIIb)

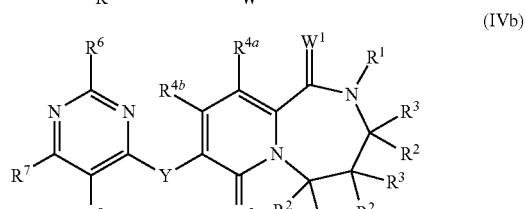

(IVb)

For MNK-specific inhibitor compounds according to Formulae IIa, IIb, IIIa, IIIb, IVa and IVb, variables W¹ and W² are both oxo. In certain embodiments for compounds according to Formulae IIa, IIb, IIIa, IIIb, IVa and IVb, W¹ is oxo and W² is thione group. According to one embodiment, Formulae IIa, IIb, IIIa, IIIb, IVa and IVb compounds comprise an oxo at $W^1$ and a =N—OR' group at $W^2$. Also encompassed within the scope of the present MNK-specific inhibitors are Formulae IIa, IIb, IIIa, IIIb, IVa and IVb compounds having a thione group at $W^1$ and an oxo group at $W^2$.

For Formulae IIa, IIb, IIIa, IIIb, IVa and IVb compounds, each of substituents $R^2$ and $R^3$ can be the same in which case the carbon atom which $R^2$ and $R^3$ are attached is not a chiral carbon. In certain embodiments, however, substituents $R^2$ and $R^3$ are different. Thus, the carbon atom to which $R^2$ and $R^3$ are attached is chiral and the resulting compound will have stereoisomers.

In certain MNK-specific inhibitor embodiments, each $R^2$ and $R^3$ in Formulae IIa, IIb, IIIa, IIIb, IVa and IVb is hydrogen. Alternatively, one of $R^2$ or $R^3$ groups in Formulae IIa, IIb, IIIa, IIIb, IVa and IVb is hydrogen and the other group is alkyl optionally substituted with 1, 2 or 3 J groups. For certain compounds according to Formulae IIa, IIb, IIIa, IIIb, IVa and IVb, $R^2$ and $R^3$ are both alkyl groups that are optionally substituted with 1, 2 or 3 J groups.

For some compounds in accordance with Formula IIa or Formula IIb, $R^2$ is alkyl and $R^3$ is alkyl substituted with 1, 2 or 3 J groups. Exemplary of this category of Formula IIa and Formula IIb compounds are the following: compounds with substituent $R^2$ as alkyl and $R^3$ is haloalkyl; compounds with substituent compounds with substituent $R^2$ as alkyl and $R^3$ is cycloalkyl optionally substituted with 1, 2 or 3 J groups; compounds with substituent $R^2$ as alkyl and $R^3$ is cyclopentyl optionally substituted with 1, 2 or 3 J groups; compounds with substituent $R^2$ as alkyl and $R^3$ is aryl optionally substituted with 1, 2 or 3 J groups; compounds with substituent $R^2$ as alkyl and $R^3$ is phenyl optionally substituted with 1, 2 or 3 J groups; compounds with substituent $R^2$ as alkyl and $R^3$ is cycloalkylalkylene optionally substituted with 1, 2 or 3 J groups; compounds with substituent $R^2$ as alkyl and $R^3$ is aralkylene optionally substituted with 1, 2 or 3 J groups; compounds with substituent $R^2$ as alkyl and $R^3$ is benzyl optionally substituted with 1, 2 or 3 J groups; compounds with substituent $R^2$ as alkyl and $R^3$ is heterocyclyl optionally substituted with 1, 2 or 3 J groups; compounds with substituent $R^2$ as alkyl and $R^3$ is heteroaryl optionally substituted with 1, 2 or 3 J groups; compounds with substituent $R^2$ as alkyl and $R^3$ is thiophenyl, thiazolyl or pyridinyl; compounds with substituent $R^2$ as alkyl and $R^3$ is heterocyclylalkylene substituted or substituted with 1, 2 or 3 J groups; or compounds with substituent $R^2$ as alkyl and $R^3$ is heteroarylalkylene optionally substituted with 1, 2 or 3 J groups.

In some embodiments, for compounds according to Formulae IIa, IIb, IIIa, IIIb, IVa and IVb, each $R^2$ and $R^3$ are independently hydrogen, alkyl, cycloalkyl, cycloalkylalkylene, heterocyclyl or heterocyclylalkylene, and any such alkyl, cycloalkyl, cycloalkylalkylene, heterocyclyl or heterocyclylalkylene can optionally be substituted with 1, 2 or 3 J groups, independently selected from the group consisting of halogen, amino, alkylaminyl and alkyl.

For certain Formulae IIIa, IIIb, IVa and IVb compounds, $R^2$ and $R^3$ together with the carbon atom to which they are attached form a cycloalkyl or heterocyclyl ring.

Also contemplated are Formula I compounds where Y is —N($R^5$)—, subscript "n" is 1 and $R^2$ and $R^3$ together with the carbon atom to which they are attached form a cycloalkyl or heterocyclyl ring "A." Such compounds conform to Formula Va and the cycloalkyl or heterocyclyl ring "A" may optionally be substituted with 1, 2 or 3 J groups.

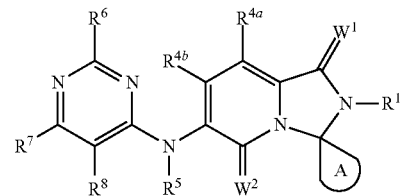

(Va)

Alternatively, in some embodiments Y in Formula I is —O—, —S—, —C(O)—, sulfoxide, sulfone, —$CHR^9$— or —$CH_2$—, "n" is 1 and $R^2$ and $R^3$ together with the carbon atom to which they are attached form a cycloalkyl or heterocyclyl ring A. Such compounds conform to Formula Vb and the cycloalkyl or heterocyclyl ring "A" may optionally be substituted with 1, 2 or 3 J groups. When "Y" is —$CHR^9$— in Formula Vb, substituent $R^9$ is either hydrogen, lower alkyl or hydroxy.

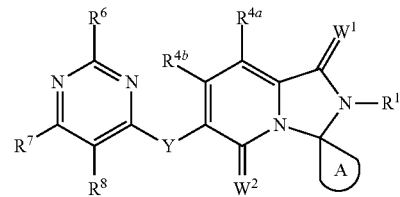

(Vb)

For Formula Va and Formula Vb compounds, $W^1$ and $W^2$ are both oxo and ring A is a cycloalkyl optionally substituted with 1, 2 or 3 J groups. Also contemplated are Formula Va and Formula Vb compounds for which ring A is a fused cycloalkyl optionally substituted with 1, 2 or 3 J groups; ring A is a cycloalkyl optionally substituted with 1, 2 or 3 J groups; ring A is a cyclobutyl, cyclopentyl or cyclohexyl optionally substituted with 1, 2 or 3 J groups, for example, J groups selected from the group consisting of halogen, amino, alkylaminyl and alkyl.

For some embodiments, ring A of a Formula Va or a Formula Vb is a heterocyclyl optionally substituted with 1, 2 or 3 J groups. Exemplary of such heterocyclyl groups are pyrrolidinyl, piperidinyl, tetrahydropyranyl, thietanyl or azetidinyl. In one embodiment, each of the above exemplified heterocyclyl may optionally be substituted with 1, 2 or 3 J groups. For certain Formula Va or a Formula Vb compounds ring A is a cycloalkyl substituted with at least 2J groups attached to the same carbon atom of the cycloalkyl, and the two J groups attached to the same carbon taken together form oxo group. In another embodiment, ring A of a Formula Va or a Formula Vb is a heterocyclyl substituted with at least 2J groups that are attached to the same hetero atom and wherein such 2 J groups taken together to form oxo. For some Formula Va or a Formula Vb compounds the cycloalkyl or heterocyclyl ring A is substituted with J groups selected from from the group consisting of halogen, cyano, hydroxy, trifluoromethyl, N-methyl amino, methyl, difluoroethylene, and methylenenitrile.

The present invention also provides compounds in accordance with Formula VI or its stereoisomers, tautomers or pharmaceutically acceptable salts. Formula VI is a subgenus of Formula I in which Y is —N($R^5$)— and substituent groups $R^5$ and $R^8$ together with the atoms to which they are attached form a heterocycle ring B which may optionally be substituted with 1, 2 or 3 J groups.

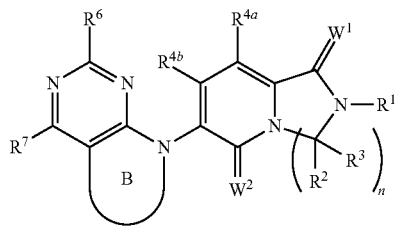
(VI)

Also encompassed within the scope of the present MNK-specific inhibitors are Formula I compounds in which variable "Y" is —N(R⁵)—, and substituent groups R⁷ and R⁸ together with the atoms to which they are attached form a fused ring C. Such compounds or the stereoisomer, tautomer or pharmaceutically acceptable salt conform to Formula VIIa. For Formula VIIa compounds, ring C may optionally be substituted with 1, 2 or 3 J groups.

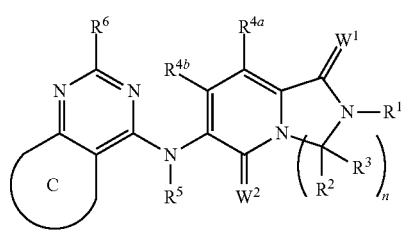
(VIIa)

According to one embodiment, variable "Y" in Formula I is —O—, —S—, —C(O)—, sulfoxide, sulfone, —CHR⁹— or —CH₂—, and substituent groups R⁷ and R⁸ together with the atoms to which they are attached form a fused ring C. Such compounds and their stereoisomers, tautomers or pharmaceutically acceptable salts conform to Formula VIIb. For Formula VIIb compounds where "Y" is —CHR⁹—, substituent R⁹ can be hydrogen, lower alkyl or hydroxy.

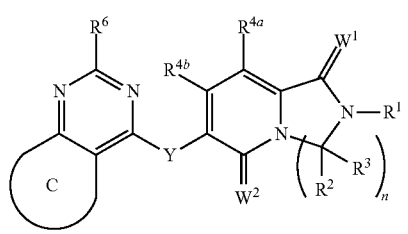
(VIIb)

For Formula VIIb compounds, fused ring C may optionally be substituted with 1, 2 or 3 J groups. In one MNK-specific inhibitor embodiment, W¹ and W² are both oxo for Formula VI, Formula VIIa and Formula VIIb compounds.

MNK-specific inhibitors of this disclosure are further directed to Formulae I, Ia, IIa, IIb, IIIa, IIIb, IVa, IVb, Va, Vb, VI, VIIa and VIIb compounds where R¹ is hydrogen or a lower alkyl group selected from methyl, ethyl, propyl, butyl, iso-propyl, sec-butyl, or tert-butyl, for example, compounds with R¹ as methyl.

For certain Formulae I, Ia, IIa, IIb, IIIa, IIIb, IVa, IVb, Va, Vb, VI, VIIa and VIIb compounds, R⁴ᵃ is selected from the group consisting of hydrogen, halogen, alkyl, alkoxy, thioalkyl, alkenyl, and cycloalkyl while substituent R⁴ᵇ is hydrogen or halogen. R⁵ in Formulae I, Ia, IIa, IIb, IIIa, IIIb, IVa, IVb, Va, Vb, VI, VIIa and VIIb is hydrogen or lower alkyl, while substituents R⁶, R⁷ and R⁸ are hydrogen.

In certain embodiments of this disclosure, R⁶ and R⁷ in Formula VI are both hydrogen, while for certain Formula VIIa and Formula VIIb compounds R⁶ is hydrogen.

MNK-specific inhibitors of this disclosure are further directed to Formulae I, Ia, IIa, IIb, IIIa, IIIb, IVa, IVb, Va, and Vb compounds where substituent groups R⁶ and R⁸ are both hydrogen, and R₇ is selected from the group consisting of hydroxy, halogen, cyano, alkyl, alkenyl, alkynyl, alkoxy, cycloalkyl, cycloalkylalkylene, cycloalkylalkenylene, amino, alkylaminyl, alkylcarbonylaminyl, cycloalkylcarbonylaminyl, cycloalkylaminyl, heterocyclylaminyl, heteroaryl, and heterocyclyl. For these compounds, any alkyl, alkenyl, alkynyl, alkoxy, cycloalkyl, cycloalkylalkylene, cycloalkylalkenylene, amino, alkylaminyl, alkylcarbonylaminyl, cycloalkylcarbonylaminyl, cycloalkylaminyl, heterocyclylaminyl, heteroaryl, or heterocyclyl is optionally substituted with 1, 2 or 3 J groups. In certain embodiments, R₇ is selected from the group consisting of alkyl, cycloalkyl, cycloalkylalkylene, cycloalkylalkenylene, amino, alkylaminyl, alklycarbonylaminyl, cycloalkylcarbonylaminyl, heterocyclylaminyl, heteroaryl, heterocyclyl and cycloalkylaminyl. For such compounds any alkyl, alkenyl, cycloalkyl, cycloalkylalkylene, cycloalkylalkenylene, amino, alkylaminyl, alklycarbonylaminyl, cycloalkylcarbonylaminyl, heterocyclylaminyl, heteroaryl, heterocyclyl or cycloalkylaminyl may optionally be substituted with 1, 2 or 3 J groups. Thus, certain embodiments provide Formulae I, Ia, IIa, IIb, IIIa, IIIb, IVa, IVb, Va, and Vb compounds where substituent groups R⁶ and R⁸ are both hydrogen, and R₇ is amino; substituent groups R⁶ and R⁸ are both hydrogen, and R₇ is alkylaminyl; substituent groups R⁶ and R⁸ are both hydrogen, and R₇ is —NHCH₃; substituent groups R⁶ and R⁸ are both hydrogen, and R₇ is cycloalkyl, for example cyclopropyl; substituent groups R⁶ and R⁸ are both hydrogen, and R₇ is cycloalkylaminyl substituted with 1 to 3 J groups, for instance halogens.

In one embodiment, for compounds in accordance with Formulae I, Ia, IIa, IIb, IIIa, IIIb, IVa, IVb, Va, and Vb, substituent groups R⁶ and R⁸ are both hydrogen, and R₇ is selected from the group consisting of —NHCH(CF₃)cyclopropyl, cycloalkylcarbonylaminyl, —NHC(O)cyclopropyl, cycloalkylalkenylene, and —CH=CHcyclopropyl.

For any compound in accordance with Formulae I, Ia, IIa, IIb, IIIa, IIIb, IVa, IVb, Va, Vb, VI, VIIa, and VIIb, J is —SH, —SR⁹, —S(O)R⁹, —S(O)₂R⁹, —S(O)NH₂, —S(O)NR⁹R⁹, —NH₂, —NR⁹R⁹, —COOH, —C(O)OR⁹, —C(O)R⁹, —C(O)—NR⁹R⁹, hydroxy, cyano, halogen, acetyl, alkyl, lower alkyl, alkenyl, alkynyl, alkoxy, haloalkyl, thioalkyl, cyanoalkylene, alkylaminyl, NH₂—C(O)-alkylene, NR⁹R⁹—C(O)-alkylene, —CHR⁹—C(O)— lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —CHR⁹—C(O)-cycloalkyl, —C(O)-cycloalkyl, —CHR⁹—C(O)-aryl, —CHR⁹-aryl, —C(O)-aryl, —CHR⁹—C(O)-heterocycloalkyl, —C(O)-heterocycloalkyl, heterocyclylaminyl, or heterocyclyl and R⁹ is hydrogen, lower alkyl or —OH. Additionally, when two J groups bound to the same carbon or hetero atom they may be taken together to form oxo.

For certain compounds according to Formulae I, Ia, IIa, IIb, IIIa, IIIb, IVa, IVb, Va, Vb, VI, VIIa, and VIIb, J is halogen, hydroxy, alkyl, alkenyl, alkynyl or cyanoalkylene. Illustrative alkyl or alkylene chains are those having $C_1$-$C_{10}$ carbon atoms, $C_1$-$C_8$ carbon atoms, $C_1$-$C_6$ carbon atoms, $C_1$-$C_4$ carbon atoms, $C_1$-$C_3$ carbon atoms as well as ethyl and methyl groups. Alternatively, when J is alkenyl, or alkynyl, the carbon chain has at least one double or triple bond respectively and $C_2$-$C_{10}$ carbon atoms, $C_2$-$C_8$ carbon atoms, $C_2$-$C_6$ carbon atoms, $C_2$-$C_4$ carbon atoms, or $C_2$-$C_3$ carbon atoms.

A MNK-specific inhibitor of Formula (I), as well as Formulae Ia, IIa, IIb, IIIa, IIIb, IVa, IVb, Va, Vb, VI, VIIa and VIIb, may be isotopically-labelled by having one or more atoms replaced by an atom having a different atomic mass or mass number. Examples of isotopes that can be incorporated into the compounds of structure (I) include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds may be useful to help determine or measure the effectiveness of the compounds, by characterizing, for example, the site or mode of action, or binding affinity to pharmacologically important site of action. Certain isotopically-labelled compounds of Formula (I), for example, those incorporating a radioactive isotope, are useful in drug or substrate tissue distribution studies. The radioactive isotopes tritium, i.e., $^3H$, and carbon-14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I), as well as Formulae Ia, IIa, IIb, IIIa, IIIb, IVa, IVb, Va, Vb, VI, VIIa and VIIb, can generally be prepared by conventional techniques known to those skilled in the art or by processes analogous to those described in the Preparations and Examples as set out in U.S. patent application Ser. No. 14/748,990 filed Jun. 24, 2015 and entitled "MNK Inhibitors and Methods Related Thereto," which compounds and synthetic methods are incorporated herein in their entirety, using an appropriate isotopically-labeled reagent in place of the non-labeled reagent previously employed.

Embodiments of this disclosure are also meant to encompass the in vivo metabolic products of the MNK-specific inhibitors of Formulae I, Ia, IIa, IIb, IIIa, IIIb, IVa, IVb, Va, Vb, VI, VIIa and VIIb. Such products may result from, for example, the oxidation, reduction, hydrolysis, amidation, esterification, and the like of the administered compound, primarily due to enzymatic processes. Accordingly, the instant disclosure includes compounds produced by a process comprising administering a MNK-specific inhibitor of this disclosure to a mammal for a period of time sufficient to yield a metabolic product thereof. Such products are typically identified by administering a radiolabelled MNK-specific inhibitor as described herein in a detectable dose to an animal, such as rat, mouse, guinea pig, monkey, or human, allowing sufficient time for metabolism to occur, and isolating conversion products from the urine, blood or other biological samples.

In some embodiments, a MNK-specific inhibitor of any one of compounds according to Formulae I, Ia, IIa, IIb, IIIa, IIIb, IVa, IVb, Va, Vb, VI, VIIa and VIIb are in the form of a pharmaceutically acceptable salt, which includes both acid and base addition salts.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, or the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of a MNK-specific inhibitor compound of this disclosure. As used herein, the term "solvate" refers to an aggregate that comprises one or more molecules of a compound of the invention with one or more molecules of solvent. A solvent may be water, in which case the solvate may be a hydrate. Alternatively, a solvent may be an organic solvent. Thus, the MNK-specific inhibitor compounds of the present disclosure may exist as a hydrate, including a monohydrate, dihydrate, hemihydrate, sesquihydrate, trihydrate, tetrahydrate or the like, as well as the corresponding solvated forms. The MNK-specific inhibitor compounds of this disclosure may be true solvates, while in other cases, the compounds may merely retain adventitious water or be a mixture of water plus some adventitious solvent.

A "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are non-superimposeable mirror images of one another.

MNK-specific inhibitors of this disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The term "tautomer" refers to a proton shift from one atom of a molecule to another atom of the same molecule. For example, when $W^1$ is oxo and $R^1$ is H, the present disclosure provides tautomers of a Formula I compound as illustrated below:

droazaindenone Inhibitors of MNK1 and MNK2") and 62/247,966 (entitled "Pyrrolo-, Pyrazolo-, Imidazo-Pyrimidine and Pyridine Compounds that Inhibit MNK1 and MNK2"). Such compounds are provided for purpose of illustration and not limitation.

TABLE 1

Exemplary MNK-Specific Inhibitors

| Cmpd. No. | Structure |
|---|---|
| 1 | 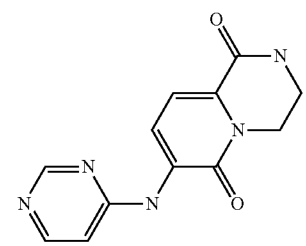 [SMILES: O=C1NCCn2c1ccc(Nc1ccncn1)c2=O] |
| 2 | 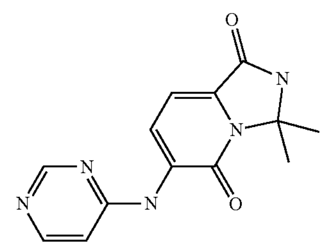 [SMILES: CC1(C)NC(=O)c2ccc(Nc3ccncn3)c(=O)n21] |

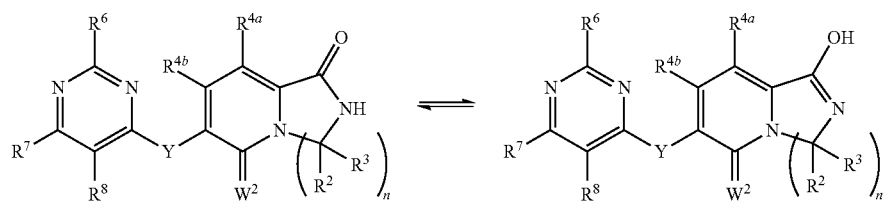

Similar tautomers exists for Formulae I, Ia, IIa, IIb, IIIa, IIIb, IVa, IVb, Va, Vb, VI, VIIa and VIIb compounds. The compounds are synthesized using conventional synthetic methods, and more specifically using the general methods and specific synthetic protocols of the Examples found in U.S. patent application Ser. No. 14/748,990 filed Jun. 24, 2015 and entitled "MNK Inhibitors and Methods Related Thereto," which compounds and synthetic methods are incorporated herein in their entirety.

Representative MNK-specific inhibitor compounds of this disclosure are set forth in Table 1 and in U.S. Patent Application Publication No. US 2015/0376181, which compounds are incorporated herein by reference in their entirety. Similarly, incorporated herein by reference in their entirety are compounds and methods of making the same from U.S. Provisional Patent Application No. 62/247,953 (entitled "Isoindoline, Azaisoindoline, Dihydroindenone and Dihy- TABLE 1-continued Exemplary MNK-Specific Inhibitors

| Cmpd. No. | Structure |
|---|---|
| 3 | 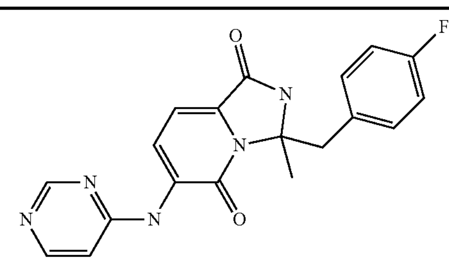 |

TABLE 1-continued

Exemplary MNK-Specific Inhibitors

| Cmpd. No. | Structure |
|---|---|
| 4 | (4-chlorobenzyl substituted structure) |
| 5 | (3-fluorobenzyl substituted structure) |
| 6 | (spirocyclopentane substituted structure) |
| 7 | (2,2,2-trifluoroethyl substituted structure) |
| 8 | (isopropyl substituted structure) |
| 9 | (cyclopentyl substituted structure) |
| 10 | (cyclopropanecarboxamide substituted structure) |
| 11 | (4-fluorophenyl substituted structure) |
| 12 | (3-fluorophenyl substituted structure) |
| 13 | (4-chlorophenyl substituted structure) |

TABLE 1-continued

Exemplary MNK-Specific Inhibitors

| Cmpd. No. | Structure |
|---|---|
| 14 | 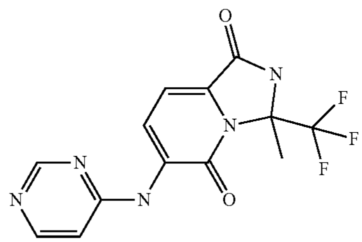 [SMILES: CC1(C(F)(F)F)NC(=O)c2ccc(Nc3ccncn3)c(=O)n21] |
| 15 | 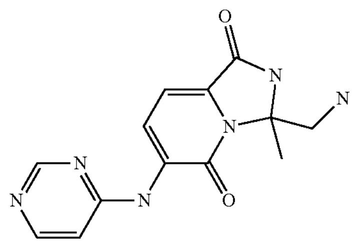 [SMILES: CC1(CN)NC(=O)c2ccc(Nc3ccncn3)c(=O)n21] |
| 16 | 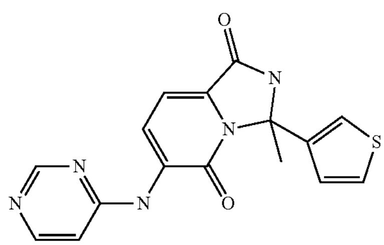 [SMILES: CC1(c2ccsc2)NC(=O)c2ccc(Nc3ccncn3)c(=O)n21] |
| 17 | 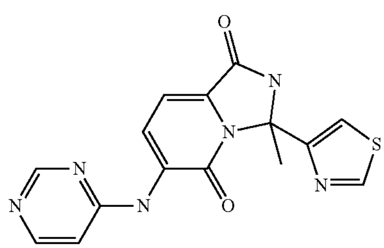 [SMILES: CC1(c2cscn2)NC(=O)c2ccc(Nc3ccncn3)c(=O)n21] |
| 18 | 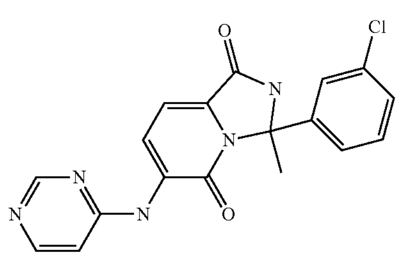 [SMILES: CC1(c2cccc(Cl)c2)NC(=O)c2ccc(Nc3ccncn3)c(=O)n21] |
| 19 | 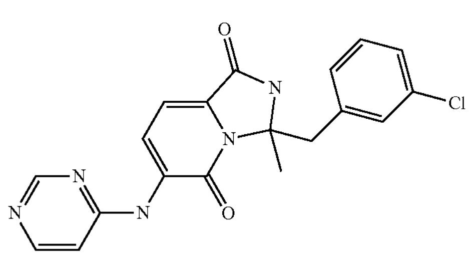 [SMILES: CC1(Cc2cccc(Cl)c2)NC(=O)c2ccc(Nc3ccncn3)c(=O)n21] |
| 20 | |
| 21 | |
| 22 | |
| 23 | |

TABLE 1-continued
Exemplary MNK-Specific Inhibitors
| Cmpd. No. | Structure |
|---|---|
| 24 | 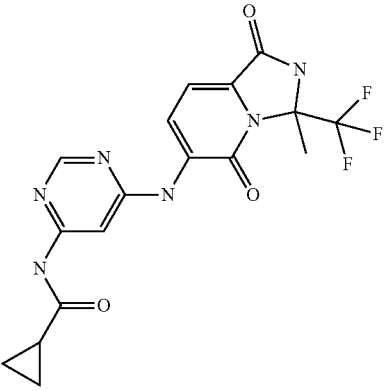 [SMILES: CC1(C(F)(F)F)NC(=O)c2ccc(Nc3cc(NC(=O)C4CC4)ncn3)c(=O)n21] |
| 25 | 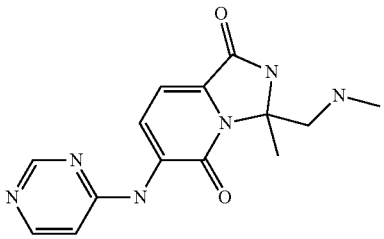 [SMILES: CNCC1(C)NC(=O)c2ccc(Nc3ccncn3)c(=O)n21] |
| 26 | 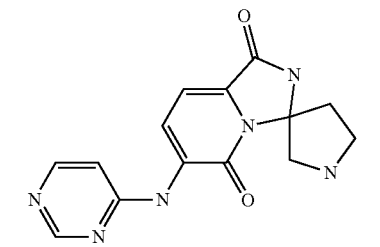 [SMILES: O=C1NC2(CCNC2)n2c1ccc(Nc1ccncn1)c2=O] |
| 27 | 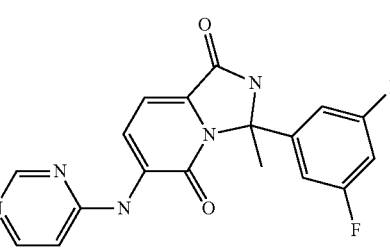 |
| 28 | 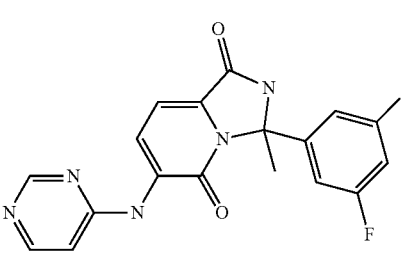 |
| 29 | 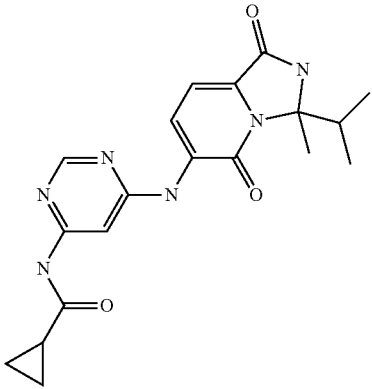 [SMILES: CC(C)C1(C)NC(=O)c2ccc(Nc3cc(NC(=O)C4CC4)ncn3)c(=O)n21] |
| 30 | 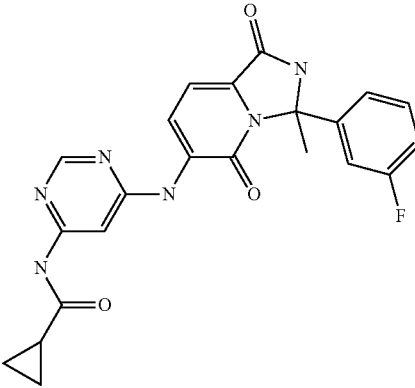 |
| 31 | 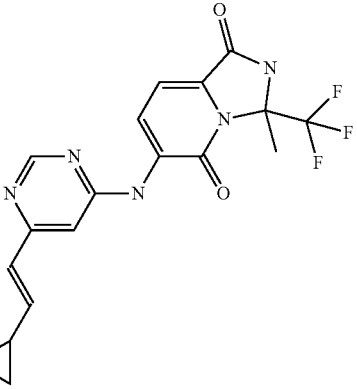 |
| 32 | 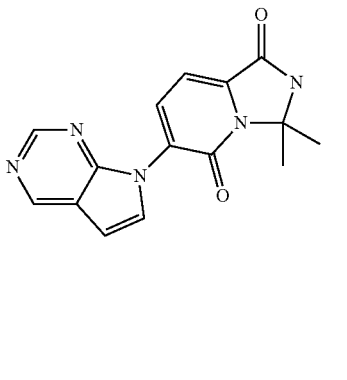 [SMILES: CC1(C)NC(=O)c2ccc(-n3ccc4cncnc43)c(=O)n21] |

TABLE 1-continued

Exemplary MNK-Specific Inhibitors

| Cmpd. No. | Structure |
|---|---|
| 33 | 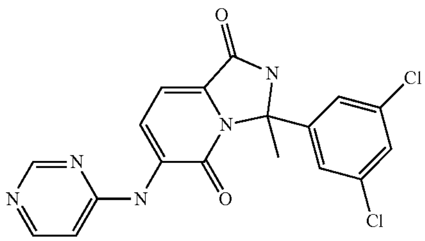 [SMILES: CC1(c2cc(Cl)cc(Cl)c2)NC(=O)c2ccc(Nc3ccncn3)c(=O)n21] |
| 34 | 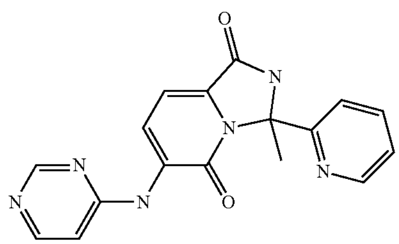 [SMILES: CC1(c2ccccn2)NC(=O)c2ccc(Nc3ccncn3)c(=O)n21] |
| 35 | 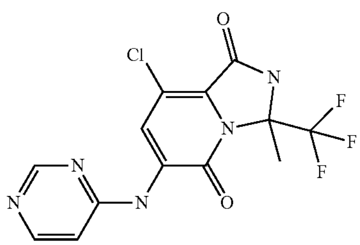 [SMILES: CC1(C(F)(F)F)NC(=O)c2c(Cl)cc(Nc3ccncn3)c(=O)n21] |
| 36 | 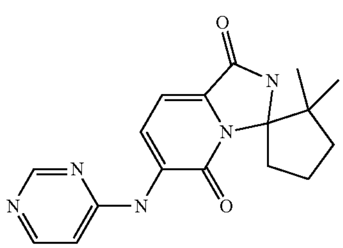 [SMILES: CC1(C)CCCC12NC(=O)c1ccc(Nc3ccncn3)c(=O)n12] |
| 37 | 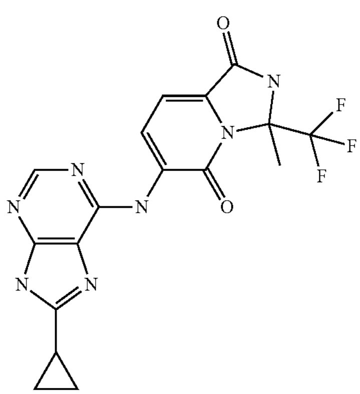 [SMILES: CC1(C(F)(F)F)NC(=O)c2ccc(Nc3ncnc4[nH]c(C5CC5)nc34)c(=O)n21] |
| 38 | 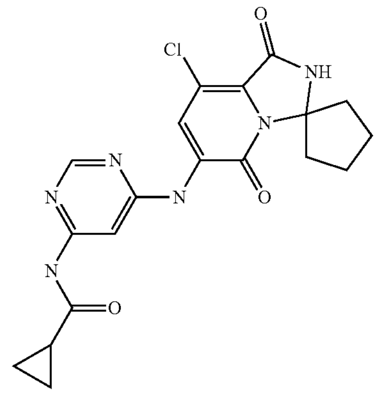 [SMILES: O=C1NC2(CCCC2)n2c1c(Cl)cc(Nc1cc(NC(=O)C3CC3)ncn1)c2=O] |
| 39 | 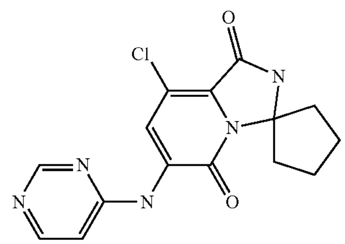 [SMILES: O=C1NC2(CCCC2)n2c1c(Cl)cc(Nc1ccncn1)c2=O] |
| 40 | 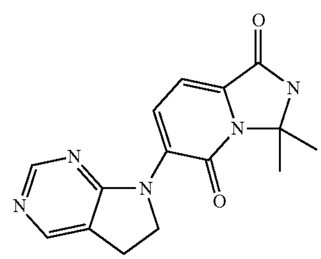 [SMILES: CC1(C)NC(=O)c2ccc(N3CCc4cncnc43)c(=O)n21] |
| 41 | 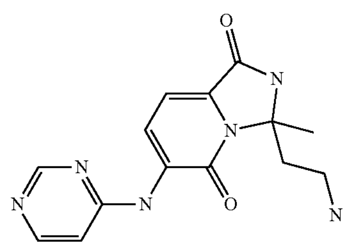 [SMILES: CC1(CCN)NC(=O)c2ccc(Nc3ccncn3)c(=O)n21] |
| 42 | 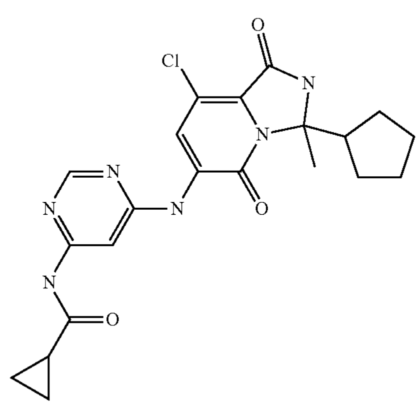 [SMILES: CC1(C2CCCC2)NC(=O)c2c(Cl)cc(Nc3cc(NC(=O)C4CC4)ncn3)c(=O)n21] |

TABLE 1-continued

Exemplary MNK-Specific Inhibitors

| Cmpd. No. | Structure |
|---|---|
| 43 | |
| 44 | |
| 45 | |
| 46 | 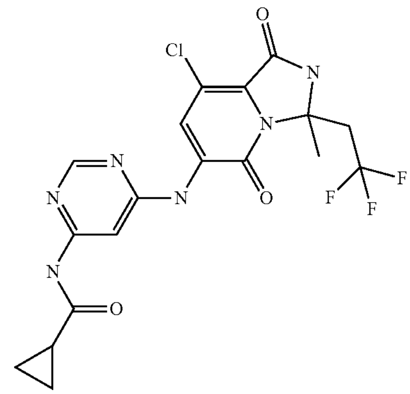 [SMILES: CC1(CC(F)(F)F)NC(=O)c2c(Cl)cc(Nc3cc(NC(=O)C4CC4)ncn3)c(=O)n21] |
| 47 | 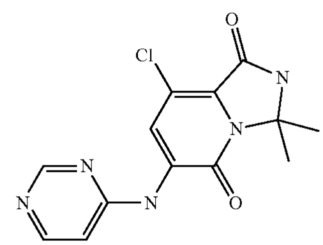 [SMILES: CC1(C)NC(=O)c2c(Cl)cc(Nc3ccncn3)c(=O)n21] |
| 48 | 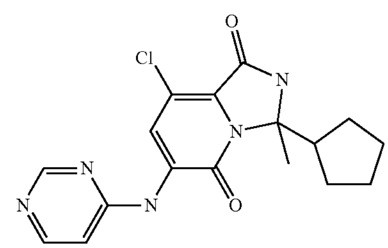 [SMILES: CC1(C2CCCC2)NC(=O)c2c(Cl)cc(Nc3ccncn3)c(=O)n21] |
| 49 | 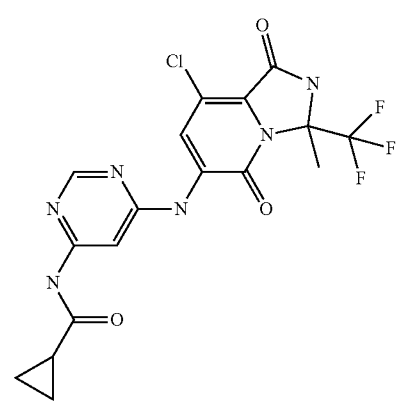 [SMILES: CC1(C(F)(F)F)NC(=O)c2c(Cl)cc(Nc3cc(NC(=O)C4CC4)ncn3)c(=O)n21] |

TABLE 1-continued

Exemplary MNK-Specific Inhibitors

| Cmpd. No. | Structure |
|---|---|
| 50 | |
| 51 | |
| 52 | |
| 53 | |
| 54 | 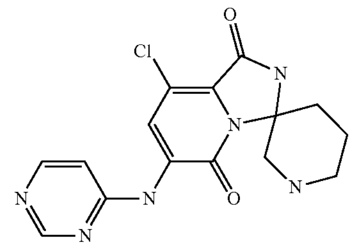 [SMILES: O=C1NC2(CCCNC2)n2c1c(Cl)cc(Nc1ccncn1)c2=O] |
| 55 | 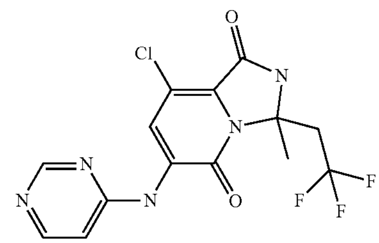 [SMILES: CC1(CC(F)(F)F)NC(=O)c2c(Cl)cc(Nc3ccncn3)c(=O)n21] |
| 56 | 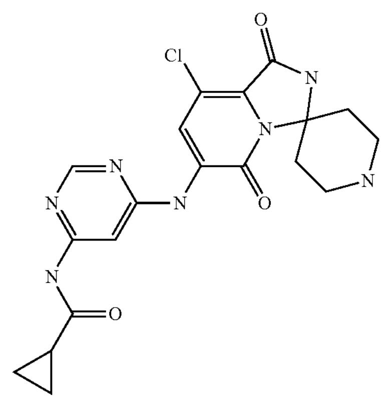 [SMILES: O=C1NC2(CCNCC2)n2c1c(Cl)cc(Nc1cc(NC(=O)C3CC3)ncn1)c2=O] |
| 57 | 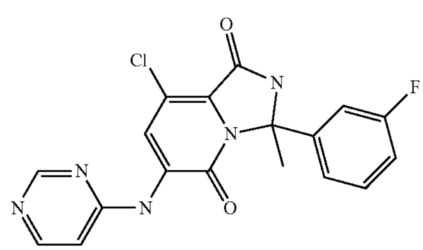 [SMILES: CC1(c2cccc(F)c2)NC(=O)c2c(Cl)cc(Nc3ccncn3)c(=O)n21] |
| 58 | 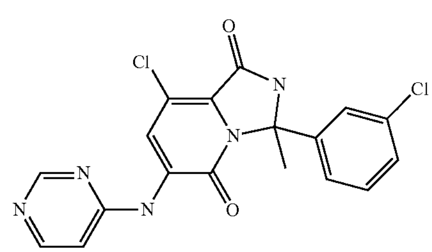 [SMILES: CC1(c2cccc(Cl)c2)NC(=O)c2c(Cl)cc(Nc3ccncn3)c(=O)n21] |

TABLE 1-continued

Exemplary MNK-Specific Inhibitors

| Cmpd. No. | Structure |
|---|---|
| 59 | |
| 60 | |
| 61 | |
| 62 | 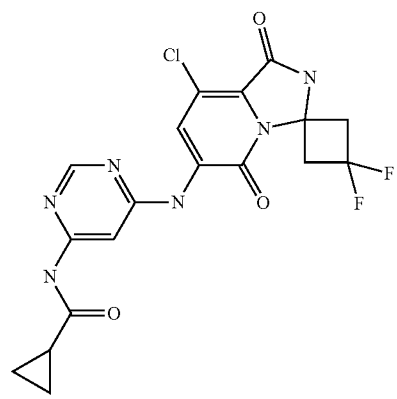 [SMILES: O=C1NC2(CC(F)(F)C2)n2c1c(Cl)cc(Nc1cc(NC(=O)C3CC3)ncn1)c2=O] |
| 63 | 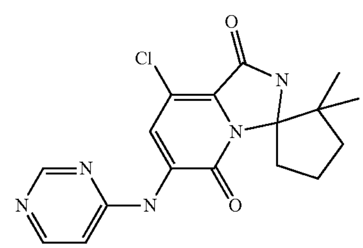 [SMILES: CC1(C)CCCC12NC(=O)c1c(Cl)cc(Nc3ccncn3)c(=O)n12] |
| 64 | 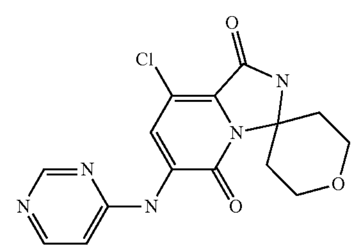 [SMILES: O=C1NC2(CCOCC2)n2c1c(Cl)cc(Nc1ccncn1)c2=O] |
| 65 | 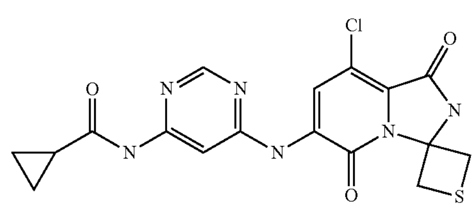 [SMILES: O=C1NC2(CSC2)n2c1c(Cl)cc(Nc1cc(NC(=O)C3CC3)ncn1)c2=O] |
| 66 | 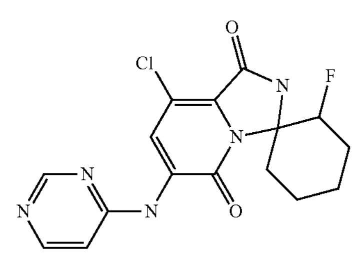 [SMILES: O=C1NC2(CCCCC2F)n2c1c(Cl)cc(Nc1ccncn1)c2=O] |

TABLE 1-continued

Exemplary MNK-Specific Inhibitors

| Cmpd. No. | Structure |
|---|---|
| 67 | 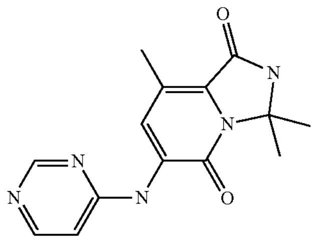 [SMILES: Cc1cc(Nc2ccncn2)c(=O)n2c1C(=O)NC2(C)C] |
| 68 | 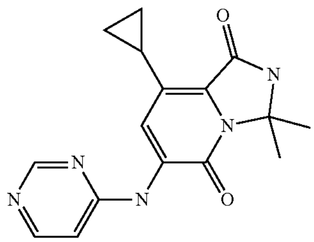 [SMILES: CC1(C)NC(=O)c2c(C3CC3)cc(Nc3ccncn3)c(=O)n21] |
| 69 | 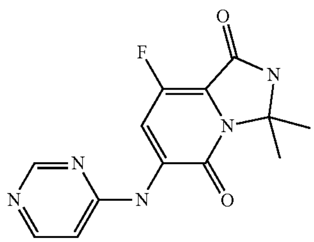 |
| 70 | 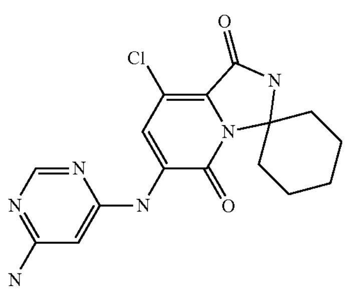 [SMILES: Nc1cc(Nc2cc(Cl)c3n(c2=O)C2(CCCCC2)NC3=O)ncn1] |
| 71 | 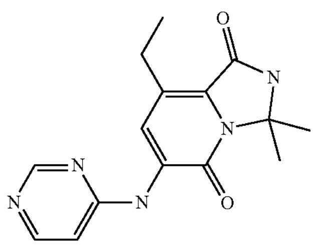 [SMILES: CCc1cc(Nc2ccncn2)c(=O)n2c1C(=O)NC2(C)C] |
| 72 | 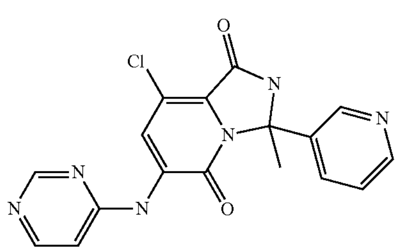 [SMILES: CC1(c2cccnc2)NC(=O)c2c(Cl)cc(Nc3ccncn3)c(=O)n21] |
| 73 | 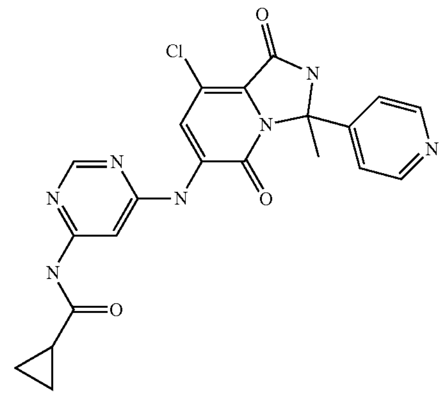 [SMILES: CC1(c2ccncc2)NC(=O)c2c(Cl)cc(Nc3cc(NC(=O)C4CC4)ncn3)c(=O)n21] |
| 74 | 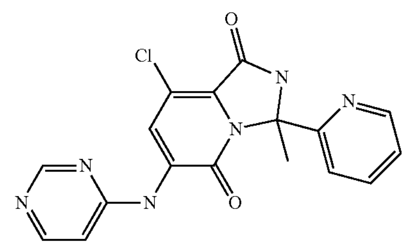 [SMILES: CC1(c2ccccn2)NC(=O)c2c(Cl)cc(Nc3ccncn3)c(=O)n21] |
| 75 | 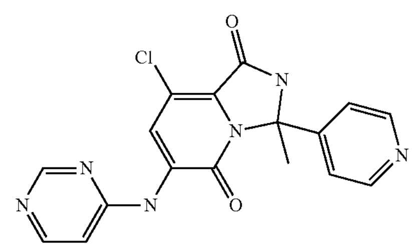 [SMILES: CC1(c2ccncc2)NC(=O)c2c(Cl)cc(Nc3ccncn3)c(=O)n21] |
| 76 | 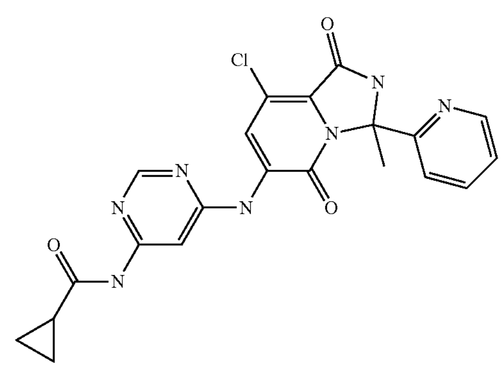 [SMILES: CC1(c2ccccn2)NC(=O)c2c(Cl)cc(Nc3cc(NC(=O)C4CC4)ncn3)c(=O)n21] |

TABLE 1-continued
Exemplary MNK-Specific Inhibitors
| Cmpd. No. | Structure |
|---|---|
| 77 | 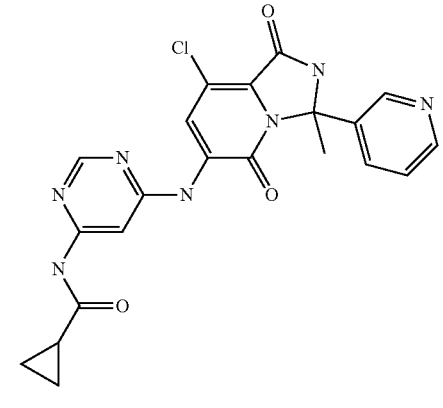 [SMILES: CC1(c2cccnc2)NC(=O)c2c(Cl)cc(Nc3cc(NC(=O)C4CC4)ncn3)c(=O)n21] |
| 78 | 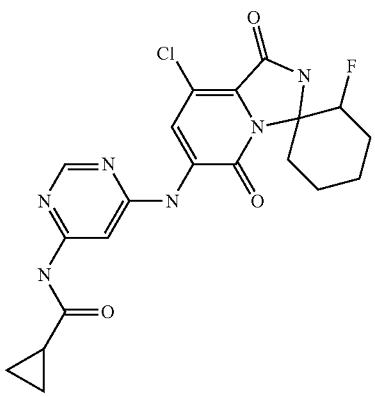 [SMILES: O=C1NC2(CCCCC2F)n2c1c(Cl)cc(Nc1cc(NC(=O)C3CC3)ncn1)c2=O] |
| 79 | 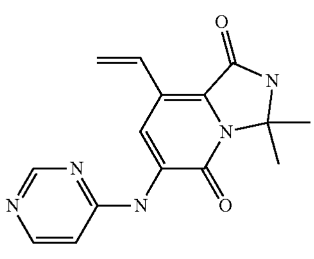 [SMILES: C=Cc1cc(Nc2ccncn2)c(=O)n2c1C(=O)NC2(C)C] |
| 80 | 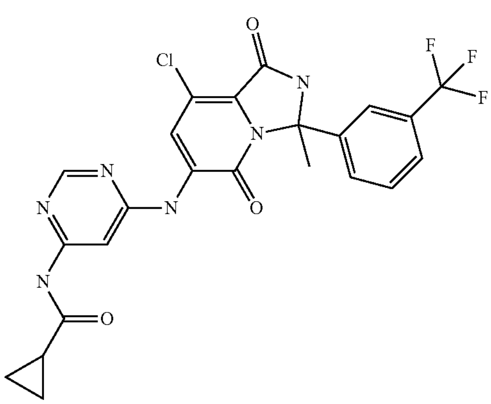 [SMILES: CC1(c2cccc(C(F)(F)F)c2)NC(=O)c2c(Cl)cc(Nc3cc(NC(=O)C4CC4)ncn3)c(=O)n21] |
| 81 | 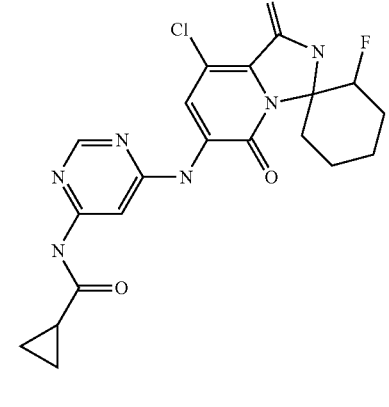 |
| 82 | |
| 83 | |
| 84 | |

TABLE 1-continued

Exemplary MNK-Specific Inhibitors

| Cmpd. No. | Structure |
|---|---|
| 85 | (structure) |
| 86 | (structure) |
| 87 | (structure) |
| 88 | (structure) |
| 89 | (structure) |
| 90 | (structure) |
| 91 | (structure) |
| 92 | (structure) |
| 93 | (structure) |

TABLE 1-continued

Exemplary MNK-Specific Inhibitors

| Cmpd. No. | Structure |
|---|---|
| 94 | 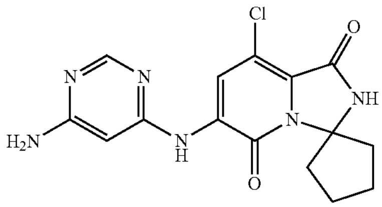 [SMILES: Nc1cc(Nc2cc(Cl)c3n(c2=O)C2(CCCC2)NC3=O)ncn1] |
| 95 | 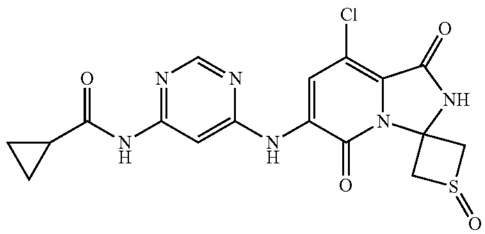 [SMILES: O=C1NC2(CS(=O)C2)n2c1c(Cl)cc(Nc1cc(NC(=O)C3CC3)ncn1)c2=O] |
| 96 | 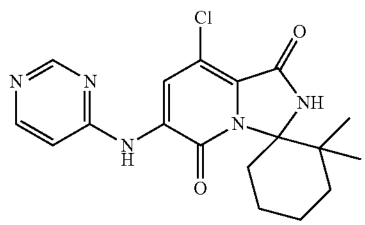 [SMILES: CC1(C)CCCCC12NC(=O)c1c(Cl)cc(Nc3ccncn3)c(=O)n12] |
| 97 | 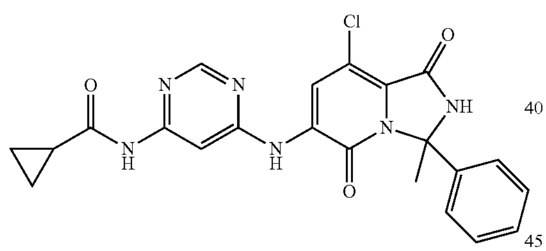 |
| 98 | 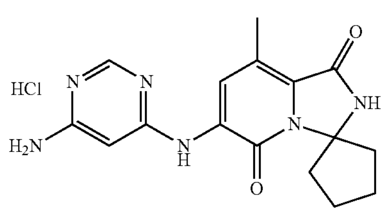 [SMILES: Cl ; Cc1cc(Nc2cc(N)ncn2)c(=O)n2c1C(=O)NC21CCCC1] |
| 99 | 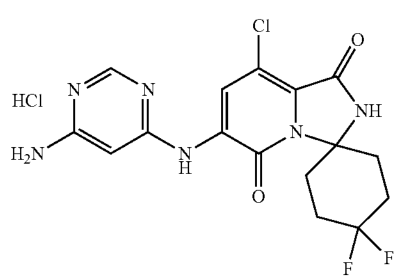 [SMILES: Cl ; Nc1cc(Nc2cc(Cl)c3n(c2=O)C2(CCC(F)(F)CC2)NC3=O)ncn1] |
| 100 | 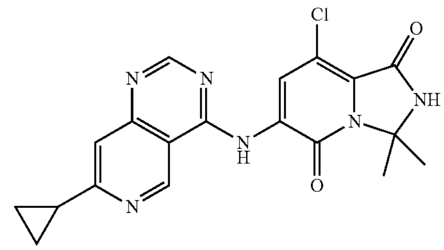 [SMILES: CC1(C)NC(=O)c2c(Cl)cc(Nc3ncnc4cc(C5CC5)ncc34)c(=O)n21] |
| 101 | 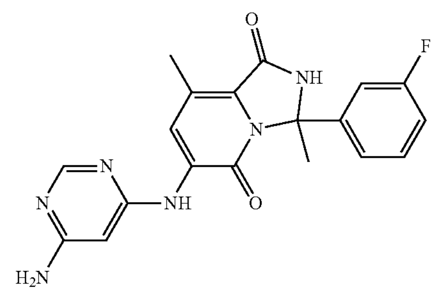 [SMILES: Cc1cc(Nc2cc(N)ncn2)c(=O)n2c1C(=O)NC2(C)c1cccc(F)c1] |
| 102 | 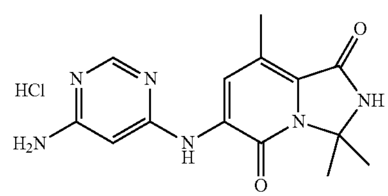 [SMILES: Cl ; Cc1cc(Nc2cc(N)ncn2)c(=O)n2c1C(=O)NC2(C)C] |
| 103 | 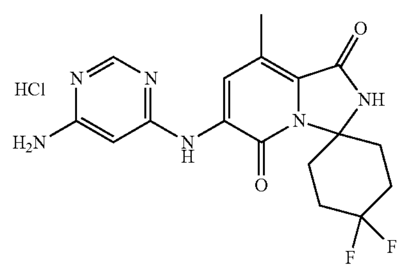 [SMILES: Cl ; Cc1cc(Nc2cc(N)ncn2)c(=O)n2c1C(=O)NC21CCC(F)(F)CC1] |
| 104 | 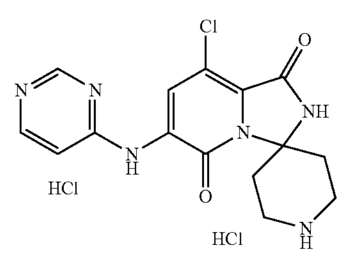 [SMILES: O=C1NC2(CCNCC2)n2c1c(Cl)cc(Nc1ccncn1)c2=O ; Cl ; Cl] |
| 105 | 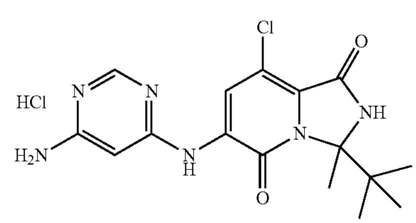 [SMILES: Cl ; CC(C)(C)C1(C)NC(=O)c2c(Cl)cc(Nc3cc(N)ncn3)c(=O)n21] |

TABLE 1-continued

Exemplary MNK-Specific Inhibitors

| Cmpd. No. | Structure |
|---|---|
| 106 | 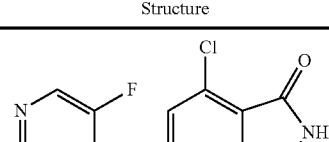 (shown with 2 HCl) |
| 107 | (structure with HCl) |
| 108 | (structure with •2 HCl) |
| 109 | (structure with HCl) |
| 110 | (structure with HCl) |
| 111 | (structure with HCl) |
| 112 | (structure) |

Examples of other MNK inhibitors that may be used in combination with the MNK-specific inhibitors of this disclosure and according to any of the methods described herein, include cercosporamide; SEL201; CGP57380 (see, Knauf et al., *Mol. Cell. Biol.* 21:5500-5511, 2001); CGP52088 (see Tschopp et al., *Mol. Cell. Biol. Res. Commun.* 3:205-211, 2000); YYC-37 (Schmid, "Targeting cap-dependent translation for cancer therapy: Identification of novel Mnk kinase inhibitors with enzymatic assays," www.fhnw.ch/lifesciences/master/master-thesis/MS_MT_Schmid_Raffaela_2014.pdf, 2014); a retinamide retinonic acid metabolism blocking agent (also known as retinamide RAIVIBA) (e.g., VNLG-152) (see, PCT Publication No. WO 2010/036404; Ramalingam et al., *Oncotarget* 5:530-543, 2014; Mbatia et al., *J. Med. Chem.* 58:1900-1914, 2015); a sulfoximine substituted quinazoline derivative, as disclosed in U.S. Pat. No. 8,901,138; a pyrrolopyrimidine compound as disclosed in U.S. Pat. No. 8,697,713, PCT Publication No. WO 2013/174743, or PCT Publication No. WO 2014/044691; a thienopyrimidine compound as disclosed in U.S. Pat. No. 8,486,953, U.S. Patent Publication No. US 2010/0143341, PCT Publication No. WO 2013/174744; or PCT Publication No. WO 2014/118229; a piperazine-based compound (e.g., ETC036 or ETC037) as disclosed in PCT Publication No. WO 2014/088519; a bicyclic heterocyclic derivative (e.g., compound 20, 359, or 416) as disclosed in PCT Publication No. WO 2013/147711; a pyrazolopyrimidine compound as disclosed in U.S. Pat. No. 8,071,607; a substituted thiazolopyrimidine compound as disclosed in PCT Publication No. WO 2014/135480; a substituted imidazopyridazine compound as disclosed in U.S. Patent Publication Nos. US 2014/0296231; US 2014/0288069; US 2014/0228370; US 2014/0194430; PCT Publication Nos. WO 2013/149909; WO 2013/144189, WO 2013/087581, WO 2014/128093, WO 2014/076162, or WO 2014/118135; a substituted pyrazolopyrimidinylamino-indazole compound as disclosed in PCT Publication No. WO 2014/118226; a substituted indazol-pyrrolopyrimidine compound as disclosed in PCT Publication No. WO 2014/048894 or WO 2014/048869; a substituted benzothienopyrimidine compound as disclosed in PCT Publication No. WO 2013/174735; sulfoximine substituted quinazoline compound as disclosed in PCT Publication No. WO 2014206922; or a heterocyclyl aminoimidazopyridazine compound as disclosed in PCT Publication No. WO 2012/175591 (each of the compounds of these references is incorporated herein by reference, in their entirety).

In certain embodiments, a MNK-specific inhibitor is a compound of any one of Formulae I, Ia, IIa, IIb, IIIa, IIIb, IVa, IVb, Va, Vb, VI, VIIa and VIIb, or from Table 1 or Table 2A, which is formulated as a pharmaceutical composition in an amount effective to treat a particular disease or condition of interest (e.g., cancer, chronic infection) upon administration of the pharmaceutical composition to a mammal (e.g., human). In particular embodiments, a pharmaceutical composition comprises a MNK-specific inhibitor as described herein and a pharmaceutically acceptable carrier, diluent or excipient.

In this regard, a "pharmaceutically acceptable carrier, diluent or excipient" includes any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved by the United States Food and Drug Administration as being acceptable for use in humans or domestic animals.

Further, a "mammal" includes primates, such as humans, monkeys and apes, and non-primates such as domestic animals, including laboratory animals and household pets (e.g., cats, dogs, swine, cattle, sheep, goats, horses, rabbits), and non-domestic animals, such as wildlife or the like.

A pharmaceutical composition of this disclosure can be prepared by combining or formulating a MNK-specific inhibitor as described herein with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Exemplary routes of administering such pharmaceutical compositions include oral, topical, transdermal, inhalation, parenteral, sublingual, buccal, rectal, vaginal, and intranasal. The term parenteral, as used herein, includes subcutaneous injections, intravenous, intramuscular, intrasternal injection or infusion techniques. Pharmaceutical compositions of this disclosure are formulated to allow the active ingredients contained therein to be bioavailable upon administration to a patient. Compositions that will be administered to a subject or patient take the form of one or more dosage units, where, for example, a tablet may be a single dosage unit, and a container of a MNK-specific inhibitor as described herein in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). A composition to be administered will, in any event, contain a therapeutically effective amount of a MNK-specific inhibitor of this disclosure, or a pharmaceutically acceptable salt thereof, for modulating an immune response to aid in treatment of a disease or condition of interest in accordance with the teachings herein.

A pharmaceutical composition of a MNK-specific inhibitor as described herein may be in the form of a solid or liquid. In one aspect, the carrier(s) are particulate so that the compositions are, for example, in tablet or powder form. The carrier(s) may be liquid, with a composition being, for example, an oral syrup, injectable liquid or an aerosol, which is useful in, for example, inhalatory administration. When intended for oral administration, a pharmaceutical composition of a MNK-specific inhibitor of this disclosure is preferably in either solid or liquid form, where semi-solid, semi-liquid, suspension and gel forms are included within the forms considered herein as either solid or liquid.

As a solid composition for oral administration, a pharmaceutical composition of a MNK-specific inhibitor as described herein may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

A pharmaceutical composition may be in the form of a liquid, for example, an elixir, syrup, solution, emulsion or suspension. The liquid may be for oral administration or for delivery by injection, as two examples. When intended for oral administration, preferred compositions contain, in addition to a MNK-specific inhibitor, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of MNK-specific inhibitors, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of a MNK-specific inhibitor intended for either parenteral or oral administration should contain an amount of a MNK-specific inhibitor of this disclosure such that a suitable dosage will be obtained.

A pharmaceutical composition of a MNK-specific inhibitor may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, a composition of a MNK-specific inhibitor of this disclosure may be included with a transdermal patch or iontophoresis device.

The pharmaceutical composition of a MNK-specific inhibitor may be intended for rectal administration, in the form, for example, of a suppository, which will melt in the rectum and release the drug. A composition for rectal administration may contain an oleaginous base as a suitable nonirritating excipient. Such bases include, for example, lanolin, cocoa butter or polyethylene glycol.

The pharmaceutical composition of a MNK-specific inhibitor may include various materials that modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of this disclosure in solid or liquid form may include an agent that binds to a MNK-specific inhibitor described herein and thereby assist in the delivery of the compound. Suitable agents that may act in this capacity include a monoclonal or polyclonal antibody, a protein or a liposome.

A pharmaceutical composition of a MNK-specific inhibitor may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of MNK-specific inhibitors may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation, may determine preferred aerosol formulations and delivery modes.

A pharmaceutical composition of this disclosure may be prepared by methodology well-known in the pharmaceutical art. For example, a pharmaceutical composition intended to be administered by injection can be prepared by combining a MNK-specific inhibitor as described herein with a sterile solvent so as to form a solution. A surfactant may be added to facilitate the formation of a homogeneous solution or suspension. Surfactants are compounds that non-covalently interact with a compound of this disclosure so as to facilitate dissolution or homogeneous suspension of the compound in an aqueous delivery system.

As used herein, a "combination" refers to a combination comprising a MNK-specific inhibitor and an inhibitor of an immunosuppression component, each of which may be administered serially (sequentially), concurrently or simultaneously, as described herein. For example, any one of the MNK-specific inhibitors of Formula I, Ia, IIa, IIb, IIIa, IIIb, IVa, IVb, Va, Vb, VI, VIIa or VIIb can be combined with (a) an antibody specific for PD-1, such as pidilizumab, nivolumab, or pembrolizumab; (b) an antibody specific for PD-L1, such as MDX-1105, BMS-936559, MEDI4736, MPDL3280A, or MSB0010718C; (c) an antibody specific for CTLA4, such as tremelimumab or ipilimumab; (d) a chemotherapeutic agent, such as vemurafenib, dabrafenib, trametinib, cobimetinib, sunitinib, erlotinib, paclitaxel, or docetaxel; (e) anti-CD137 (4-1BB) antibody, such as urelumab; (f) an anti-CD134 (OX-40) antibody, such as MDI6469 (an OX-40 agonist); (g) lenalidomide or pomalidomide; or (h) any combination thereof.

In certain embodiments, a combination of a MNK-specific inhibitor with an inhibitor of an immunosuppression component further comprises a chemotherapeutic agent, each of which may be administered serially (sequentially), concurrently or simultaneously, as described herein. For example, any one of the MNK-specific inhibitors of Formula I, Ia, IIa, IIb, IIIa, IIIb, IVa, IVb, Va, Vb, VI, VIIa or VIIb can be combined with (a) an antibody specific for PD-1, such as pidilizumab, nivolumab, or pembrolizumab; (b) an antibody specific for PD-L1, such as MDX-1105, BMS-936559, MEDI4736, MPDL3280A, or MSB0010718C; (c) an antibody specific for CTLA4, such as tremelimumab or ipilimumab; (d) an anti-CD134 (OX-40) antibody, such as MDI6469 (an OX-40 agonist); (e) lenalidomide or pomalidomide; or (f) anti-CD137 (4-1BB) antibody, such as urelumab; and a chemotherapeutic agent, such as vemurafenib, dabrafenib, trametinib, cobimetinib, sunitinib, erlotinib, paclitaxel, or docetaxel.

Methods of Altering Immunomodulatory Activity

MNK-specific inhibitors as described herein can unexpectedly reduce the level of immunosuppression components (e.g., immune checkpoint molecules, immunosuppressive cytokines) involved in immune inhibitory pathways, also known as immunosuppression pathways. In certain aspects, the present disclosure provides methods for immune modulation by administering an effective amount of a MNK-specific inhibitor to a subject in need thereof. Exemplary forms of immune modulation include increasing the activity of an immune cell; reducing the down-modulation of an immune cell; inducing or enhancing an immune response; prolonging an immune response; stimulating an antigen-specific T cell response; inhibiting an immunosuppressive signaling pathway; promoting endogenous immunity (pre-existing and de novo); inhibiting disease-associated immune resistance (e.g., cancer); enhancing a vaccine-induced immune response; or any combination thereof. In further embodiments, a subject in need of immune modulation has a hyperproliferative disorder (e.g., cancer), infection or infectious disease (e.g., viral, bacterial, protozoan infection). In particular embodiments, a subject in need of immune modulation has a hyperproliferative disorder associated with immune resistance (e.g., cancer) or an infectious disease (e.g., chronic infection) associated with immune resistance. In any of the aforementioned embodiments, the subject being treated is human.

An exemplary immune inhibitory or suppressive pathway (modulated by MNK-specific inhibitors of this disclosure) is mediated by Programmed cell death protein 1, also known as PD-1 or CD279, which is a cell surface receptor belonging to the immunoglobulin superfamily and is expressed on T cells (CD8+ effector T cells, CD4+ helper T cells, $T_{regs}$, or any combination thereof), natural killer (NK) cells, macrophages, dendritic cells, and B cells. PD-1 binds to two ligands, PD-L1 (also known as B7-H1 or CD274) and PD-L2 (also known as BC-DC or CD273). MNK-specific inhibitors of this disclosure also reduce the levels of PD-L1.

By way of background, PD-1 and its ligands primarily act to regulate inflammatory responses in tissues by T cells recognizing antigen in peripheral tissues. PD-1 expression is induced on activated T cells and inflammatory signals in the tissues induce expression of PD-1 ligands on, for example, antigen presenting cells. Upon ligand binding, PD-1 inhibits kinases involved in T cell activation via SHP2 phosphatase, resulting in inhibition of TCR-mediated activation, expansion, cytokine production, and acquisition of effector functions of CD8+ effector T cells. PD-1-mediated dampening of the immune response protects peripheral tissues from damage and helps maintain self-tolerance. IFNγ secretion is a signal for PD-L1 induction, which is predominantly made by T helper 1 ($T_H1$) cells. Activity of PD-1 receptor signaling may be detected by examining T cell proliferation and cytokine production (e.g., IFNγ, IL-2), using methods known in the art.

PD-1 is also highly expressed on $T_{reg}$ cells, and PD-1-mediated signaling in $T_{reg}$ cells may result in further suppression of effector immune responses by promoting $T_{reg}$ development and function (Francisco et al., *Immunol. Rev.* 236:219, 2010). PD-1 signaling may also dampen NK cell activation and cytotoxicity and antibody production via its effects on NK cells and B cells (Benson et al., *Blood* 116:2286, 2010; Thibult et al., *Int. Immunol.* 25:129, 2013).

High levels of persistent PD-1 expression, which may occur as a result of chronic antigen exposure (e.g., cancer, chronic infection) may induce a state of exhaustion and anergy among cognate antigen-specific T cells (Barber et al., *Nature* 438:682, 2006).

Down-regulation of the immune response, e.g., T cell response, by PD-1 signaling may facilitate persistence of cancer or infection. PD-1 ligands are commonly upregulated on the surface of cancer cells of numerous tumors and tumor infiltrating lymphocytes (TILs), which limit local anti-tumor T cell responses. Up-regulation of PD-L1 expression has been found on melanoma, ovarian cancer, lung cancer, renal cancer, breast cancer, and many other cancers, and has been associated with poor prognosis (reviewed in Pardoll, supra). PD-L2 up-regulation has been also reported on certain B cell lymphomas (Id.).

Certain immunosuppression components, such as immune checkpoint proteins like PD-1 or LAG3, may also play a role in persistence of chronic infections. PD-1 has been shown to be upregulated on T cells of HIV infected patients, which correlates with viral load and T cell exhaustion, resulting in decreased cellular proliferation, cytotoxic function, and cytokine secretion (reviewed in Eichbaum, *Curr. Med. Chem.* 18:3971, 2011 and Hofmeyer et al., *J. Biomed. Biotech.* 2011:451694, 2011). PD-1 mediated T cell exhaustion is also important in the persistence of other chronic infections, such as hepatitis B virus, hepatitis C virus, and LCMV, and is implicated in persistence or reactivation of bacterial infection (e.g., *Helicobacter pylori, Mycobacterium*), trypanosomal infection (e.g., *Leishmania donovani*), parasitic protozoan infection (e.g., *Toxoplasma gondii*), helminth infection (e.g., *Schistosoma mansoni*), and herpes simplex virus 1 infection (e.g., HSV1) (Hofmeyer et al., supra).

Another exemplary immunosuppression component is lymphocyte activation gene 3 (LAG3, also known as CD223), which is highly expressed on $T_{reg}$ cells and has a role in enhancing the immunosuppressive activity of $T_{reg}$ cells (Goldberg and Drake, *Curr. Top. Microbiol. Immunol.* 344:269, 2011). LAG3 also directly inhibits CD8$^+$ effector T cells, independently of the effect via $T_{reg}$ cells (Grosso et al., *J. Clin. Invest.* 117:3383, 2007). LAG3 is also expressed on activated CD4$^+$ and CD8$^+$ T lymphocytes where it associates with the CD3-TCR complex at the cell surface and negatively regulates signal transduction (Hannier et al., *J. Immunol.* 161:4058, 1998; Darlington et al., *J. Exp. Med.* 195:1337, 2002). The role of LAG3 in the down regulation of T cell responses is well established (Matsuzaki et al., *Proc. Nat'l. Acad. Sci. USA* 107:7875, 2010), and there is increasing evidence of its involvement in regulatory function of tumor-infiltrated T cells in cancer, such as Hodgkin's lymphomas (Gandhi et al., *Blood* 108:2280, 2006) and prostate cancer (Sfanos et al., *Clin. Cancer Res.* 14:3254, 2008). The ligand for LAG3, MHC/HLA class II molecules, are upregulated on some epithelial cancers (e.g., melanoma) and tumor infiltrating macrophages and dendritic cells. There are several LAG3 inhibitors in development, and even LAG3 antibodies that do not block LAG3-MHC class II binding are still able to enhance T cell proliferation and effector function (reviewed in Pardoll, supra).

The present disclosure provides methods of treating disease by reducing the down-modulation of an immune cell, comprising administering an effective amount of a MNK-specific inhibitor to a subject (e.g., human) in need thereof. In certain embodiments, the present disclosure provides methods of reducing or blocking PD-1, PD-L1, or LAG3 signaling for use in enhancing an immune response or reducing the down-modulation of an immune cell against a hyperproliferative disorder (e.g., cancer) or an infection or infectious disease. In certain aspects, the present disclosure provides a method of reducing levels or activity of PD-1, PD-L1, LAG3 or combinations thereof, and optionally blocking or reducing the production of immunosuppressive cytokines (e.g., IL-10), by administering a therapeutically effective amount of a MNK-specific inhibitor to a subject in need of an induced or enhanced immune response or a reduction in the down-modulation or suppression of an immune cell. In certain embodiments, a MNK-specific inhibitor is used to induce or enhance an immune response or reduce the down-modulation or suppression of an immune cell in a subject having cancer or a chronic infection. In further embodiments, a MNK-specific inhibitor is any one of the compounds of Table 1 or Table 2A, or any compound having a structure of Formula I, Ia, IIa, IIb, IIIa, IIIb, IVa, IVb, Va, Vb, VI, VIIa or VIIb. In still further embodiments, the induced or enhanced immune response comprises an antigen-specific T cell response, or the reduced down-modulation or suppression is of an antigen-specific T cell.

In particular embodiments, the method further comprises administering an inhibitor of an immunosuppression component, such as an antibody or binding fragment thereof, a fusion protein (e.g., Fc fusion), siRNA, or the like, which may be inhibitors of PD-1, PD-L1, LAG3 or combinations thereof, against other immunosuppression components (such as immunosuppressive cytokines like IL-10, IL-4, IL-1RA, IL-35), or modulating other immunosuppression components, such as $T_{reg}$ cells (e.g., reducing $T_{reg}$ cells relative to $T_E$ cells). In further embodiments, a MNK-specific inhibitor optionally mediates an increase in the level of MHC or HLA molecules to promote or enhance antigen presentation, as described herein.

In still further embodiments, the present disclosure provides a method of treating disease associated with PD-1-mediated, PD-L1-mediated or LAG3-mediated immune resistance, comprising administering an effective amount of a MNK-specific inhibitor to a subject in need thereof.

In any of the aforementioned embodiments, a MNK-specific inhibitor is any one of the compounds of Table 1 or Table 2A or any compound having a structure of Formula I, Ia, IIa, IIb, IIIa, IIIb, IVa, IVb, Va, Vb, VI, VIIa or VIIb. In still further embodiments, the induced or enhanced immune response is an antigen-specific T cell response. In particular embodiments, the method further comprises administering an inhibitor of an immunosuppression component, such as an antibody or binding fragment thereof, a fusion protein, siRNA, or the like.

In yet further embodiments, the present disclosure provides a method of inhibiting an immunosuppressive signaling pathway associated with dysregulated immune checkpoint proteins, such as PD-1, PD-L1, LAG3 or combinations thereof, comprising administering an effective amount of a MNK-specific inhibitor to a subject in need thereof, optionally inhibiting the production of immunosuppressive cytokines (e.g., IL-10). In certain embodiments, a MNK-specific inhibitor is any one of the compounds of Table 1 or Table 2A or any compound having a structure of Formula I, Ia, IIa, IIb, IIIa, IIIb, IVa, IVb, Va, Vb, VI, VIIa or VIIb. In still further embodiments, an induced or enhanced immune response is an antigen-specific T cell response. In particular embodiments, the method further comprises administering an inhibitor of an immunosuppression signal, such as an antibody or binding fragment thereof, a fusion protein, siRNA, or the like.

In more embodiments, the present disclosure provides a method of inhibiting a dysregulated PD-1, PD-L1 and/or LAG3 immunosuppressive signaling pathway, comprising administering an effective amount of a MNK-specific inhibitor to a subject in need thereof, optionally inhibiting the production of immunosuppressive cytokines (e.g., IL-10). In certain embodiments, a MNK-specific inhibitor is any one of the compounds of Table 1 or Table 2A or any compound having a structure of Formula I, Ia, IIa, IIb, IIIa, IIIb, IVa, IVb, Va, Vb, VI, VIIa or VIIb. In more embodiments, the method inhibits an immunosuppression component, such as a PD-1, PD-L1 and/or LAG3 of immunosuppressive signaling pathways, to correct dysregulated or inappropriate immune suppression and promote endogenous immunity (e.g., pre-existing or de novo). In certain embodiments, this disclosure provides a method of inhibiting an immunosuppression component to promote endogenous immunity, comprising administering an effective amount of a MNK-specific inhibitor and an immunosuppression inhibitor to a subject in need thereof, wherein (a) the MNK-specific inhibitor primes antigen-specific T cells for response to antigen in the presence of the immunosuppression inhibitor, or (b) the MNK-specific inhibitor enhances or prolongs the effect of the immunosuppression inhibitor in promoting endogenous immunity. In still further embodiments, the induced or enhanced immune response is an antigen-specific T cell response. In particular embodiments, the method further comprises administering an inhibitor of an immunosuppression component, such as an antibody or binding fragment thereof, a fusion protein, siRNA, or the like.

The methods of use of a MNK-specific inhibitor described herein may be optionally used in combination with an inhibitor targeting an immunosuppression component or production of an immunosuppression component. Exemplary immunosuppression component targets include PD-1, PD-L1, PD-L2, CTLA4, CD80, CD86, B7-H3, B7-H4, HVEM, BTLA, KIR, LAG3, GAL9, TIM3, 2B4, adenosine, A2aR, TGFβ, IL-10, IL-35, arginase, IDO, or immunosuppressive cytokines (e.g., IL-10). An immunosuppression component inhibitor may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule.

In certain embodiments, an inhibitor of an immunosuppression component is an antibody or binding fragment thereof, fusion protein, or siRNA specific for PD-1, PD-L1, PD-L2, CTLA4, CD80, CD86, B7-H3, B7-H4, HVEM, BTLA, KIR, LAG3, GAL9, TIM3, 2B4, adenosine, A2aR, TGFβ, IL-10, IL-35, arginase, IDO, or any combination thereof.

In certain embodiments, a MNK-specific inhibitor is used in combination with a PD-1 specific antibody or binding fragment thereof, such as pidilizumab, nivolumab, pembrolizumab, MEDI0680 (formerly AMP-514), MK-3475, AMP-224, BMS-936558 or any combination thereof. In further embodiments, a MNK-specific inhibitor is used in combination with a PD-L1 specific antibody or binding fragment thereof, such as BMS-936559, durvalumab (MEDI4736), atezolizumab (MPDL3280A), MSB0010718C, RG7446, or any combination thereof. In yet further embodiments, a MNK-specific inhibitor is used in combination with a LAG3 specific antibody or binding fragment thereof, such as LAG525, IMP321, IMP701, 9H12, BMS-986016, or any combination thereof. In still more embodiments, a MNK-specific inhibitor is used in combination with a PD-1 inhibitor and a CTLA4 inhibitor. In other embodiments, a MNK-specific inhibitor is used in combination with a PD-L1 inhibitor and a CTLA4 inhibitor. In yet other embodiments, a MNK-specific inhibitor is used in combination with a PD-1 inhibitor and a LAG3 inhibitor, or a PD-L1 inhibitor and a LAG3 inhibitor.

Cytotoxic T-lymphocyte associated protein 4 (CTLA4), also known as CD152, is a receptor exclusively expressed by T cells and acts as a negative regulator of T cell activation. CTLA4 primarily counteracts the activity of the T cell co-stimulatory receptor CD28. CTLA4 and CD28 share the same ligands CD80 (also known as B7.1) and CD86 (also known as B7.2), which are expressed on the surface of antigen presenting cells. Engagement of CD28 by CD80 or CD86 activates T cell proliferation and IL-2 production only if the T cell receptor has bound its cognate antigen. T cell activation through TCR and CD28 induces expression of CTLA4. CTLA4 has a higher affinity for both its ligands than CD28. Not wishing to be bound by theory, it is suggested that CTLA4 dampens T cell activation by out-competing CD28 for ligand binding and delivery of inhibitory signals to the T cell (reviewed in Pardoll, supra). CTLA4 is expressed on multiple T cell subsets, and signaling may down-modulate activity of CD8+ effector T cells, CD4+ helper T cells, and enhance $T_{reg}$ activity.

In certain embodiments, a MNK-specific inhibitor is used in combination with an inhibitor of CTLA4. In particular embodiments, a MNK-specific inhibitor is used in combination with a CTLA4 specific antibody or binding fragment thereof, such as ipilimumab, tremelimumab, CTLA4-Ig fusion proteins (e.g., abatacept, belatacept), or any combination thereof.

Other B7 family inhibitory ligands, such as B7-H3 (also known as CD276) and B7-H4 (also known as B7-S1, B7x, and VCTN1), may have an immune inhibitory role (Yi et al., *Immunol. Rev.* 229:145, 2009). The receptors for B7-H3 and B7-H4 have not yet been identified. But, B7-H3 and B7-H4 are upregulated on tumor cells and tumor-infiltrating cells (He et al., *Clin. Dev. Immunol.* 2011:695834, 2011).

In more embodiments, a MNK-specific inhibitor is used in combination with a B7-H3 specific antibody or binding fragment thereof, such as MGA271, 376.96, or both. A B7-H4 antibody binding fragment may be a scFv or fusion protein thereof, as described in, for example, Dangaj et al., *Cancer Res.* 73:4820, 2013.

CD244, also known as Natural Killer Cell Receptor 2B4, is a cell surface receptor expressed on natural killer cells, γδ T cells, and memory CD8+ (αβ) T cells. The ligand for CD244 is CD48, which is expressed on hematopoietic cells. CD244 signaling is thought to modulate NK-cell cytolytic activity in both an activating and inhibitory manner, depending on expression level of CD244 and degree of cross-linking (Chlewicki et al., *J. Immunol.* 180:8159, 2008).

B and T lymphocyte attenuator (BLTA, also known as CD272) is an inhibitor receptor whose expression is induced during T cell activation. Its ligand is herpesvirus entry mediator (HVEM, also known as TNFRSF14). HVEM is widely expressed in multiple tissue/cell types. HVEM is also upregulated on certain tumor types, including for example, melanoma, lymphoma, prostate cancer, colorectal cancer, urothelial cancer, and tumor infiltrating lymphocytes. BTLA-HVEM trans-interaction results in inhibitor effects on T cell (reviewed by Shui et al., *J. Leukoc. Biol.* 89:517, 2011). Cis-binding of HVEM-BTLA on T cells may also have an inhibitory function, which is stabilized by soluble LIGHT (also known as TNFSF14 or CD258) (Shui et al., supra).

T cell membrane protein 3 (TIM3, also known as HAVCR2) is a CD4+ T helper 1 (TH1) specific cell surface protein that is a negative regulator of T cells and TH1 and TH17 cytokine secretion (Hastings et al., *Eur. J. Immunol.* 39:2492, 2009). Its ligand is galectin 9 (GAL9). TH1 cells, characterized by IFNγ production, are important for anti-cancer and anti-viral immune responses. TH17 cells, characterized by IL-17 and IL-22 production, are important for immune response to mucosal bacterial and fungal pathogens.

Adenosine A2a receptor (A2aR) inhibits T cell response by inducing T cell anergy and by promoting expression of FOXP3 in CD4+ T cells and develop into $T_{reg}$ cells (Zarek et al., *Blood* 111:251, 2008). The ligand for A2aR is adenosine. Adenosine is released during cell death (e.g., tumors, viral infection).

Killer cell immunoglobulin-like receptors (KIR, also known as CD158) are cell surface proteins found on natural killer cells and a subset of T cells. KIR interact with a MHC class I molecule, which suppresses cytotoxicity activity of the NK cell. Individual KIR recognize distinct subsets of MHC class I allotypes. In certain embodiments, a MNK-specific inhibitor is used in combination with an inhibitor of KIR, such as lirilumab (BMS-986015).

Inhibitory cytokines, including TGFβ, IL-10, and IL-35, may inhibit immune response by suppressing TH1 type response, promoting $T_{reg}$ cell development, (Bettini and Vignali, *Curr. Opin. Immunol.* 21:612, 2009).

Indoleamine 2,3-dioxygenase (IDO) is an enzyme that catalyzes the breakdown of tryptophan to N-formyl-kynurenine. IDO is induced by IFNγ and suppresses T cell response by local depletion of tryptophan from the cellular microenvironment (Mellor, *Biochem. Biophys. Res. Comm.* 338:20-4, 2005). Without wishing to be bound by theory, it is thought that the T cells' deprivation of tryptophan and generation of toxic catabolites from the tryptophan degradation pathway induce T cell arrest and apoptosis and render the T cells inactive (Soliman et al., *Cancer J.* 16:354-9, 2010). IDO is expressed by infiltrating myeloid cells (e.g., dendritic cells) (Mellor and Munn, *Nat. Rev. Immunol.* 4:762-74, 2004). IDO is also expressed by cancer cells in a range of tumor types and may inhibit immune response to tumors (Munn, *Update Cancer Ther.* 1:175-185, 2006).

In certain embodiments, a MNK-specific inhibitor is used in combination with an IDO inhibitor, such as levo-1-methyl tryptophan, epacadostat (INCB024360; Liu et al., 2010, Blood 115:3520-30), ebselen (Terentis et al., 2010, Biochem. 49:591-600), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

The metabolism of arginine to ornithine and urea is catalyzed by arginase I and arginase II, encoded by two distinct genes located in the cytoplasm and mitochondria. Ornithine is the main substrate for the production of polyamines that are required for cell cycle progression. Arginine can also be metabolized by inducible nitric oxide synthase to produce citrulline and nitric oxide, which plays an important role in cytotoxic mechanisms. Arginase can also cause T cell anergy by decreasing expression of CD3ζ chain (Rodriguez et al., *Cancer Res.* 64:5839, 2004). Arginase is produced by myeloid derived suppressor cells, and expression has been observed in several tumor cell lines (Rodriguez and Ochoa, *Immunol. Rev.* 222:180-191, 2008).

In certain embodiments, a MNK-specific inhibitor is used in combination with an arginase inhibitor, such as N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-boronoethyl)-L-cysteine (BEC), or any combination thereof.

In certain embodiments, a MNK-specific inhibitor is used in combination with agents that target other immunomodulatory molecules. For example, a MNK-specific inhibitor can be used in combination with an anti-CD137 (4-1BB) antibody (such as urelumab), an anti-CD134 (OX-40) antibody (such as MDI6469 (an OX-40 agonist)), lenalidomide, pomalidomide, or combinations thereof.

As used herein, "hyperproliferative disorder" or "hyperproliferative disease" refers to excessive growth or proliferation as compared to a normal cell or an undiseased cell. Exemplary hyperproliferative disorders include dysplasia, neoplasia, non-contact inhibited or oncogenically transformed cells, tumors, cancers, carcinoma, sarcoma, malignant cells, pre-malignant cells, as well as non-neoplastic or non-malignant hyperproliferative disorders (e.g., adenoma, fibroma, lipoma, leiomyoma, hemangioma, fibrosis, restenosis, or the like). In certain embodiments, a cancer being treated by immune modulation via compositions and methods of this disclosure includes carcinoma (epithelial), sarcoma (connective tissue), lymphoma or leukemia (hematopoietic cells), germ cell tumor (pluripotent cells), blastoma (immature "precursor" cells or embryonic tissue), or any combination thereof. These various forms of hyperproliferative disease are known in the art and have established criteria for diagnosis and classification (e.g., Hanahan and Weinberg, *Cell* 144:646, 2011; Hanahan and Weinberg *Cell* 100:57, 2000; Cavallo et al., *Canc. Immunol. Immunother.* 60:319, 2011; Kyrigideis et al., *J. Carcinog.* 9:3, 2010).

A wide variety of hyperproliferative disorders, including solid tumors and leukemias, are amenable to the immune modulating compositions and methods disclosed herein. Exemplary cancers that may be treated by immune modulation of this disclosure include adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional representative cancers that may be treated include histiocytic disorders; histiocytosis malignant; immunoproliferative small intestinal disease; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; and trophoblastic tumor.

Exemplary hematological malignancies include acute lymphoblastic leukemia (ALL), acute myeloid leukemia (AML), chronic myelogenous leukemia (CIVIL), chronic eosinophilic leukemia (CEL), myelodysplastic syndrome (MDS), Hodgkin's lymphoma, non-Hodgkin's lymphoma (NHL) (e.g., follicular lymphoma, diffuse large B-cell lymphoma, or chronic lymphocytic leukemia), or multiple myeloma (MM).

Still further exemplary hyperproliferative disorders include adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; sertoli cell tumor; thecoma; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In particular aspects, the present disclosure provides methods for increasing the activity of an immune cell by administering an effective amount of a MNK-specific inhibitor to a subject having a solid tumor, melanoma, non-small cell lung cancer, renal cell carcinoma, renal cancer, a hematological cancer, prostate cancer, castration-resistant prostate cancer, colon cancer, rectal cancer, gastric cancer, esophageal cancer, bladder cancer, head and neck cancer, thyroid cancer, breast cancer, triple-negative breast cancer, ovarian cancer, cervical cancer, lung cancer, urothelial cancer, pancreatic cancer, glioblastoma, hepatocellular cancer, myeloma, multiple myeloma, leukemia, Hodgkin's lymphoma, non-Hodgkin's lymphoma, myelodysplastic syndrome, brain cancer, CNS cancer, malignant glioma, or any combination thereof.

In other aspects, the present disclosure provides methods for reducing the down-modulation of an immune cell by administering an effective amount of a MNK-specific inhibitor to a subject having a solid tumor, melanoma, non-small cell lung cancer, renal cell carcinoma, renal cancer, a hematological cancer, prostate cancer, castration-resistant prostate cancer, colon cancer, rectal cancer, gastric cancer, esophageal cancer, bladder cancer, head and neck cancer, thyroid cancer, breast cancer, triple-negative breast cancer, ovarian cancer, cervical cancer, lung cancer, urothelial cancer, pancreatic cancer, glioblastoma, hepatocellular cancer, myeloma, multiple myeloma, leukemia, Hodgkin's lymphoma, non-Hodgkin's lymphoma, myelodysplastic syndrome, brain cancer, CNS cancer, malignant glioma, or any combination thereof.

In still other aspects, the present disclosure provides methods for inducing, enhancing, or prolonging an immune response by administering an effective amount of a MNK-specific inhibitor to a subject having a solid tumor, melanoma, non-small cell lung cancer, renal cell carcinoma, renal cancer, a hematological cancer, prostate cancer, castration-resistant prostate cancer, colon cancer, rectal cancer, gastric cancer, esophageal cancer, bladder cancer, head and neck cancer, thyroid cancer, breast cancer, triple-negative breast cancer, ovarian cancer, cervical cancer, lung cancer, urothelial cancer, pancreatic cancer, glioblastoma, hepatocellular cancer, myeloma, multiple myeloma, leukemia, Hodgkin's lymphoma, non-Hodgkin's lymphoma, myelodysplastic syndrome, brain cancer, CNS cancer, malignant glioma, or any combination thereof.

In yet other aspects, the present disclosure provides methods for stimulating an antigen-specific T cell response by administering an effective amount of a MNK-specific inhibitor to a subject having a solid tumor, melanoma, non-small cell lung cancer, renal cell carcinoma, renal cancer, a hematological cancer, prostate cancer, castration-resistant prostate cancer, colon cancer, rectal cancer, gastric cancer, esophageal cancer, bladder cancer, head and neck cancer, thyroid cancer, breast cancer, triple-negative breast cancer, ovarian cancer, cervical cancer, lung cancer, urothelial cancer, pancreatic cancer, glioblastoma, hepatocellular cancer, myeloma, multiple myeloma, leukemia, Hodgkin's lymphoma, non-Hodgkin's lymphoma, myelodysplastic syndrome, brain cancer, CNS cancer, malignant glioma, or any combination thereof. In certain embodiments, a stimulated antigen-specific T cell response is specific for a tumor-associated antigen (TAA).

In more aspects, the present disclosure provides methods for inhibiting an immunosuppressive signaling pathway by administering an effective amount of a MNK-specific inhibitor to a subject having a solid tumor, melanoma, non-small cell lung cancer, renal cell carcinoma, renal cancer, a hematological cancer, prostate cancer, castration-resistant prostate cancer, colon cancer, rectal cancer, gastric cancer, esophageal cancer, bladder cancer, head and neck cancer, thyroid cancer, breast cancer, triple-negative breast cancer, ovarian cancer, cervical cancer, lung cancer, urothelial cancer, pancreatic cancer, glioblastoma, hepatocellular cancer, myeloma, multiple myeloma, leukemia, Hodgkin's lymphoma, non-Hodgkin's lymphoma, myelodysplastic syndrome, brain cancer, CNS cancer, malignant glioma, or any combination thereof. In certain embodiments, an immunosuppressive signal involves PD-1, PD-L1, PD-L2, CTLA4, CD80, CD86, B7-H3, B7-H4, HVEM, BTLA, KIR, LAG3, GAL9, TIM3, 2B4, adenosine, A2aR, TGFβ, IL-10, IL-35, or any combination thereof. In certain embodiments, an immunosuppressive signal involves one or more dysregulated immune checkpoint proteins resulting in a subject having disease-associated immune resistance, wherein the subject is in need of treatment with a MNK-specific inhibitor to modulate the inappropriate immunosuppressive signaling pathway(s) in order to induce or enhance an immune response against the disease (e.g., cancer). In particular embodiments, an immunosuppression component associated with immune resistance is PD-1, PD-L1, LAG3, IL-10, a $T_{reg}$ cell, or combinations thereof. In certain embodiments, an inhibited immunosuppressive signaling pathway is a PD-1 pathway or a LAG3 pathway. For example, a MNK-specific inhibitor can down-regulate expression of or indirectly inhibit PD-1, PD-L1, LAG3 or all three, thereby inhibiting these immunosuppression pathways.

In further embodiments, an immunosuppressive signal includes excess regulatory T cells ($T_{regs}$), wherein a MNK-specific inhibitor alters the ratio of T effector ($T_E$) cells to $T_{reg}$ cells. In certain embodiments, the ratio of $T_E$ cells to $T_{reg}$ cells is increased in the presence of a MNK-specific inhibitor as compared to the absence of the inhibitor. In still other embodiments, a MNK-specific inhibitor counteracts an immunosuppressive signal that downregulates or reduces the expression of MHC/HLA molecules (e.g., MHC/HLA class II) to minimize antigen presentation, wherein the MNK-specific inhibitor promotes or enhances antigen presentation by regulating (i.e., increasing) the level of MHC/HLA molecules, such as MHC/HLA class II molecules.

In further aspects, the present disclosure provides methods for promoting endogenous anti-cancer immunity by administering an effective amount of a MNK-specific inhibitor to a subject having a solid tumor, melanoma, non-small cell lung cancer, renal cell carcinoma, renal cancer, a hematological cancer, prostate cancer, castration-resistant prostate cancer, colon cancer, rectal cancer, gastric cancer, esophageal cancer, bladder cancer, head and neck cancer, thyroid cancer, breast cancer, triple-negative breast cancer, ovarian cancer, cervical cancer, lung cancer, urothelial cancer, pancreatic cancer, glioblastoma, hepatocellular cancer, myeloma, multiple myeloma, leukemia, Hodgkin's lymphoma, non-Hodgkin's lymphoma, myelodysplastic syndrome, brain cancer, CNS cancer, malignant glioma, or any combination thereof. The term "endogenous" refers to an anti-cancer immune response that is present in the subject, as opposed to being acquired exogenously, for example, via immunoglobulin therapy, adoptive T cell therapy, genetically modified T cell therapy (e.g., chimeric antigen receptor, recombinant T cell receptor). In certain embodiments, the endogenous anti-cancer immunity that is promoted comprises an antigen-specific T cell response.

In still further aspects, the present disclosure provides methods for inhibiting disease-associated immune resistance by administering an effective amount of a MNK-specific inhibitor to a subject having a solid tumor, melanoma, non-small cell lung cancer, renal cell carcinoma, renal cancer, a hematological cancer, prostate cancer, castration-resistant prostate cancer, colon cancer, rectal cancer, gastric cancer, esophageal cancer, bladder cancer, head and neck cancer, thyroid cancer, breast cancer, triple-negative breast cancer, ovarian cancer, cervical cancer, lung cancer, urothelial cancer, pancreatic cancer, glioblastoma, hepatocellular cancer, myeloma, multiple myeloma, leukemia, Hodgkin's lymphoma, non-Hodgkin's lymphoma, myelodysplastic syndrome, brain cancer, CNS cancer, malignant glioma, or any combination thereof. In certain embodiments, the disease-associated immune resistance is mediated by a PD-1, PD-L1 or LAG3 immune suppression signaling pathway. In particular embodiments, inhibition of immune resistance comprises down-regulating, reducing expression, or indirectly inhibiting PD-1, PD-L1, LAG3 or combinations thereof. In certain other embodiments, inhibition of immune resistance comprises down-regulating or indirectly inhibiting PD-L2, CTLA4, CD80, CD86, B7-H3, B7-H4, HVEM, BTLA, KIR, LAG3, GAL9, TIM3, 2B4, adenosine, A2aR, TGFβ, IL-10, IL-35, arginase, IDO, or any combination thereof.

The compositions and methods for immune modulation as described herein may also be used in the context of an infection or infectious disease (e.g., viral, bacterial, fungal, parasitic, protozoan, helminth). In certain aspects, the present disclosure provides methods for (1) increasing the activity of an immune cell; (2) reducing the down-modulation of an immune cell; (3) inducing, enhancing, or prolonging an immune response; (4) stimulating an antigen-specific T cell response; (5) inhibiting an immunosuppressive signaling pathway; (6) promoting endogenous anti-infectious agent immunity; (7) enhancing vaccine-induced immune response; or (8) inhibiting disease-associated immune resistance; by administering an effective amount of a MNK-specific inhibitor to a subject (e.g., human) having an infection, such as a chronic infection.

Infectious diseases include those associated with infectious agents and include any of a variety of bacteria (e.g., pathogenic *E. coli*, *S. typhimurium*, *P. aeruginosa*, *B. anthracis*, *C. botulinum*, *C. difficile*, *C. perfringens*, *H. pylori*, *V. cholerae*, *Listeria* spp., *Rickettsia* spp., *Chlamydia* spp., *Staphylococci*, *Streptococci*, *Pneumonococci*, *Meningococci*, or the like), mycobacteria, and parasites (including any known parasitic member of the Protozoa, trypanosome, malaria, Giardia, *toxoplasma*). Infectious viruses include eukaryotic viruses, such as adenovirus, bunyavirus, cytomegalovirus, enterovirus, Epstein-Barr virus, flavivirus (e.g., hepatitis C virus (HCV), hepatitis B virus (HBV), hepatitis A virus, hepatitis E virus, Japanese encephalitis virus), herpes virus, papovavirus, papillomavirus (e.g., HPV), paramyxovirus (e.g., measles virus, mumps virus), picornavirus (e.g., rhinovirus), poliovirus, rubella virus, rhabdovirus (e.g., Rabies), orthomyxovirus (e.g., influenza), poxvirus (e.g., Vaccinia), reovirus, retrovirus, lentivirus (e.g., human immunodeficiency virus, HIV), human T leukemia virus (HTLV1, HTLV2), varicella-zoster virus, zoonotic viruses (e.g., severe acute respiratory syndrome (SARS), Ebola virus, and West Nile virus), or the like. Infectious fungi include, for example, *Candida*, *Cryptococcus*, and *Aspergillus*. In certain embodiments, methods for increasing the activity or reducing the down-modulation of an immune cell, comprises administering an effective amount of a MNK-specific inhibitor of this disclosure to a subject infected with a cytosolic pathogen whose antigens are processed and displayed with MHC or HLA class I molecules.

In any of the aforementioned embodiments, an immune cell is a lymphocyte, such as a T cell (e.g., $CD8^+$ effector T cell, $CD4^+$ helper T cell, or regulatory T cell), natural killer cell, dendritic cell, myeloid cell (such as a monocyte, macrophage, eosinophil, mast cell, basophil, or granulocyte), or any combination thereof. In particular embodiments, immune cells are T cells, such as a CD8+ effector T cells (also known as cytotoxic T lymphocytes or CTLs).

In any of the aforementioned embodiments, an immune response is mediated by a T cell, natural killer cell, dendritic cell, myeloid cell, or any combination thereof. In certain embodiments, an immune response is mediated by T cells, such as a CD8+ effector T cells.

In any of the aforementioned embodiments, immune resistance is resistance to a T cell, natural killer cell, dendritic cell, myeloid cell, or any combination thereof. In certain embodiments, immune resistance is mediated against T cells, such as a CD8+ effector T cells.

An increase in activity or induction, enhancement, prolonging, or stimulation of an immune cell or immune response, or inhibition of an immunosuppressive signaling pathway or immune resistance in any aspect of the compositions and methods described herein may be measured using methods known in the art, for example, by measuring immune cell proliferation, immune cell activity/effector function, immune cell persistence, antibody production, or cytokine production. By way of example, increased T cell activity may be demonstrated by increased T cell proliferation ($^3$H-thymidine incorporation assay, CFSE dilution assay), enhanced T cell co-stimulation, expression of T cell activation cell surface markers (flow cytometry), cytolytic activity ($^{51}$Chromium release assay), increased IFNγ or IL-2 secretion (ELISA, flow cytometry) in the presence and absence of a MNK-specific inhibitor.

In further aspects, the present disclosure provides methods for promoting an enhanced antigen-specific immune response, wherein the method comprises administering to a subject in need thereof an effective amount of a MNK-specific inhibitor and an antigen (e.g., a vaccine), wherein an antigen-specific immune response is more effective in combination with a MNK-specific inhibitor than in the absence of treatment with a MNK-specific inhibitor. The efficacy of an antigen-specific immune response may be ascertained, for example, by immune cell activation, immune cell effector function, immune cell proliferation, immune cell survival, immune cell, immune cell cytokine production, using methods known in the art. In certain embodiments, an antigen-specific immune response is a T cell response. As used herein the term "vaccine" refers to a biological preparation that induces an antigen-specific immune response. A vaccine comprises an antigen, which may be a peptide, polypeptide or protein, or immunogenic fragments thereof; a glycoprotein or immunogenic fragments thereof; a nucleic acid encoding a peptide, polypeptide, protein, or glycoprotein, or immunogenic fragments thereof; a glycolipid; a carbohydrate or carbohydrate comprising molecule; a lipid molecule; or a cell or cell preparation. In certain embodiments, a vaccine comprises a polynucleotide that encodes an antigen; a recombinant expression vector comprising the polynucleotide; an immune cell or other cell into which an antigen or a polynucleotide encoding the antigen has been introduced, a cell (live, attenuated, or killed), a cell membrane preparation, a cell organelle preparation, or an exosome of a cell. A vaccine may be prophylactic or therapeutic. A vaccine may be directed to an infectious agent or to an endogenous cell (e.g., a cancer cell). In certain embodiments, a vaccine is specific for a cancer cell antigen or tumor-associated antigen. In certain embodiments, a vaccine antigen comprises a MHC (HLA) class I epitope, a MHC (HLA) class II epitope, or a combination thereof.

"Treatment," "treating" or "ameliorating" refers to medical management of a disease, disorder, or condition of a subject (i.e., patient), which may be therapeutic, prophylactic/preventative, or a combination treatment thereof. A treatment may improve or decrease the severity at least one symptom of a disease, delay worsening or progression of a disease, or delay or prevent onset of additional associated diseases. "Reducing the risk of developing a disease" refers to preventing or delaying onset of a disease or reoccurrence of one or more symptoms of the disease (e.g., cancer). In certain embodiments, the immune modulation provided by the MNK-specific inhibitors of this disclosure aids or augments treatment regimens or aids or augments a host organism's immune system.

A "patient" or "subject" includes an animal, such as a human, cow, horse, sheep, lamb, pig, chicken, turkey, quail, cat, dog, mouse, rat, rabbit or guinea pig. The animal can be a mammal, such as a non-primate and a primate (e.g., monkey and human). In one embodiment, a patient is a human, such as a human infant, child, adolescent or adult.

A MNK-specific inhibitor of this disclosure, or pharmaceutically acceptable salt thereof, may also be administered simultaneously with, prior to, or after administration of one or more other therapeutic agents or regimens. Such combination therapy includes administration of a single pharmaceutical dosage formulation that contains a MNK-specific inhibitor of this disclosure and one or more additional active agents (e.g., inhibitor of an immunosuppression component), as well as administration of MNK-specific inhibitors of this disclosure and each active agent in its own separate pharmaceutical dosage formulation. For example, a MNK-specific inhibitor of this disclosure and another active agent can be administered to the patient together in a single oral dosage composition, such as a tablet or capsule or liquid, or each agent may be administered in separate oral dosage formulations, or each agent may administered by different routes of administration (e.g., oral and parenteral). An additional active agent may be one accepted in the art as a standard treatment for a particular disease state or disorder, such as in cancer or infection (e.g., vaccine, chemotherapeutic) or a newly emerging therapy (e.g., antibodies against one or more immunosuppression components). When separate dosage formulations are used, a MNK-specific inhibitor of this disclosure and one or more additional active agents can be administered at essentially the same time, i.e., concurrently, or at separately staggered times, i.e., sequentially; combination therapy is understood to include all these regimens. Administration of a MNK-specific inhibitor of this disclosure may be as a single dose, or administration may occur several times wherein a plurality of doses is given to a subject in need thereof.

In certain embodiments, a combination comprising a MNK-specific inhibitor and an inhibitor of an immunosuppression component, each of which may be administered serially (sequentially), concurrently or simultaneously, is used to treat a disease (such as cancer or an infection) in a subject (e.g., human). For example, a combination useful for treating a cancer or an infectious disease my comprise any one of the MNK-specific inhibitors of Formula I, Ia, IIa, IIb, IIIa, IIIb, IVa, IVb, Va, Vb, VI, VIIa or VIIb combined with (a) an antibody specific for PD-1, such as pidilizumab, nivolumab, or pembrolizumab; (b) an antibody specific for PD-L1, such as MDX-1105, BMS-936559, MEDI4736, MPDL3280A, or MSB0010718C; (c) an antibody specific for CTLA4, such as tremelimumab or ipilimumab; (d) a chemotherapeutic agent, such as vemurafenib, dabrafenib, trametinib, cobimetinib, sunitinib, erlotinib, paclitaxel, or docetaxel; (e) anti-CD137 (4-1BB) antibody, such as urelumab; (f) an anti-CD134 (OX-40) antibody, such as MDI6469 (an OX-40 agonist); (g) lenalidomide or pomalidomide; or (h) any combination thereof.

In any of the aforementioned embodiments, the method of treatment or immune modulation comprises use of the combination further comprising a chemotherapeutic agent, wherein each component of the combination may be administered serially (sequentially), concurrently or simultaneously, as described herein. For example, any one of the MNK-specific inhibitors of Formula I, Ia, IIa, IIb, IIIa, IIIb, IVa, IVb, Va, Vb, VI, VIIa or VIIb can be combined with an inhibitor of an immunosuppression component, such as (a) an antibody specific for PD-1, such as pidilizumab, nivolumab, or pembrolizumab; (b) an antibody specific for PD-L1, such as MDX-1105, BMS-936559, MEDI4736, MPDL3280A, or MSB0010718C; (c) an antibody specific for CTLA4, such as tremelimumab or ipilimumab; (d) an anti-CD134 (OX-40) antibody, such as MDI6469 (an OX-40 agonist); (e) lenalidomide or pomalidomide; or (f) anti-CD137 (4-1BB) antibody, such as urelumab; and a chemotherapeutic agent, such as vemurafenib, dabrafenib, trametinib, cobimetinib, sunitinib, erlotinib, paclitaxel, docetaxel, or the like.

In any of the aforementioned embodiments, the method of treatment or immune modulation comprises use of the combination further comprising a T cell containing a CAR specific for a cancer antigen (e.g., a tumor-associated antigen (TAA)) or an antigen expressed on infected cell or both, wherein each component of the combination may be administered serially (sequentially), concurrently or simultaneously, as described herein. For example, any one of the MNK-specific inhibitors of Formula I, Ia, IIa, IIb, IIIa, IIIb, IVa, IVb, Va, Vb, VI, VIIa or VIIb can be combined with an inhibitor of an immunosuppression component, such as (a) an antibody specific for PD-1, such as pidilizumab, nivolumab, or pembrolizumab; (b) an antibody specific for PD-L1, such as MDX-1105, BMS-936559, MEDI4736, MPDL3280A, or MSB0010718C; (c) an antibody specific for CTLA4, such as tremelimumab or ipilimumab; (d) an anti-CD134 (OX-40) antibody, such as MDI6469 (an OX-40 agonist); (e) lenalidomide or pomalidomide; or (f) anti-CD137 (4-1BB) antibody, such as urelumab; and a T cell containing a CAR specific for a cancer antigen (e.g., a tumor-associated antigen (TAA)), such as CD3, CEACAM6, c-Met, EGFR, EGFRvIII, ErbB2, ErbB3, ErbB4, EphA2, IGF1R, GD2, O-acetyl GD2, O-acetyl GD3, GHRHR, GHR, FLT1, KDR, FLT4, CD44v6, CD151, CA125, CEA, CTLA-4, GITR, BTLA, TGFBR2, TGFBR1, IL6R, gp130, Lewis A, Lewis Y, TNFR1, TNFR2, PD1, PD-L1, PD-L2, HVEM, MAGE-A, mesothelin, NY-ESO-1, PSMA, RANK, ROR1, TNFRSF4, CD40, CD137, TWEAK-R, LTβR, LIFRβ, LRP5, MUC1, OSMRβ, TCRα, TCRβ, CD19, CD20, CD22, CD25, CD28, CD30, CD33, CD52, CD56, CD80, CD81, CD86, CD123, CD171, CD276, B7H4, TLR7, TLR9, PTCH1, PTCH1, Robo1, α-fetoprotein (AFP), Frizzled, OX40 (also referred to as CD134), or CD79b; or a T cell containing a CAR specific for an antigen expressed on infected cells, such as molecules from an adenovirus, bunyavirus, herpesvirus (e.g., Epstein Barr Virus, cytomegalocvirus), papovavirus, papillomavirus (e.g., human papilloma virus, HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., human immunodeficiency virus, HIV), flavivirus (e.g., Hepatitis C virus, HCV; Hepatitis B virus, HBV).

In further embodiments, one or more doses of a MNK-specific inhibitor are administered serially (sequentially), concurrently or simultaneously with one or more doses of an inhibitor of an immunosuppression component and optionally one or more doses of a chemotherapeutic agent or a T cell containing a CAR specific for a TAA or an antigen expressed on an infected cell. In still further embodiments, multiple doses of a MNK-specific inhibitor are administered serially (sequentially), concurrently or simultaneously with multiple doses of an inhibitor of an immunosuppression component and multiple doses of a chemotherapeutic agent. In still further embodiments, multiple doses of a MNK-specific inhibitor are administered serially (sequentially), concurrently or simultaneously with one to about four doses of an inhibitor of an immunosuppression component and one to about four dose of a chemotherapeutic agent. In all the above embodiments, a MNK-specific inhibitor may be administered first or an inhibitor of an immunosuppression component may be administered first or a chemotherapeutic agent may be administered first.

The combinations may be presented as a combination kit. The phrase "combination kit" or "kit of parts," as used herein, means one or more pharmaceutical compositions that are used to administer a MNK-specific inhibitor, an inhibitor of an immunosuppression component, and optionally a chemotherapeutic agent according to this disclosure. When a MNK-specific inhibitor and an inhibitor of an immunosuppression component are administered simultaneously, the combination kit can contain a MNK-specific inhibitor and an inhibitor of an immunosuppression component in a single pharmaceutical composition or in separate pharmaceutical compositions, such as a tablet, vial or both, and a chemotherapeutic agent in a vial. When a MNK-specific inhibitor and a chemotherapeutic agent are administered simultaneously, the combination kit can contain a MNK-specific inhibitor and a chemotherapeutic agent in a single pharmaceutical composition or in separate pharmaceutical compositions, such as a tablet, vial or both, and an inhibitor of an immunosuppression component in a vial. When a MNK-specific inhibitor and an inhibitor of an immunosuppression component and/or optionally a chemotherapeutic agent are not administered simultaneously, the combination kit will contain a MNK-specific inhibitor, an inhibitor of an immunosuppression component and optionally a chemotherapeutic agent in separate pharmaceutical compositions, wherein a MNK-specific inhibitor, an inhibitor of an immunosuppression component and optionally a chemotherapeutic agent are either in a single package, or are in separate pharmaceutical compositions in separate packages.

In one aspect, there is provided a kit of parts comprising the following components: (a) a MNK-specific inhibitor in a pharmaceutically acceptable carrier, diluent or excipient; (b) an inhibitor of an immunosuppression component in a pharmaceutically acceptable carrier, diluent or excipient; and optionally (c) a chemotherapeutic agent in a pharmaceutically acceptable carrier, diluent or excipient.

In certain embodiments, a kit of parts comprises the following components: (a) a MNK-specific inhibitor in a pharmaceutically acceptable carrier, diluent or excipient; (b) an inhibitor of an immunosuppression component in a pharmaceutically acceptable carrier, diluent or excipient; and optionally (c) a chemotherapeutic agent in a pharmaceutically acceptable carrier, diluent or excipient, wherein the components are provided in a form that is suitable for sequential, separate and/or simultaneous administration.

In certain embodiments, a kit of parts comprises: (1) a first container comprising a MNK-specific inhibitor in a pharmaceutically acceptable carrier, diluent or excipient; and (2) a second container comprising an inhibitor of an immunosuppression component in a pharmaceutically acceptable carrier, diluent or excipient, and optionally (3) a third container comprising a chemotherapeutic agent in a pharmaceutically acceptable carrier, diluent or excipient. A combination kit can also be provided with instruction, such as dosage and administration instructions. Such dosage and administration instructions can be of the kind that are provided to a doctor, for example, by a drug product label or they can be of the kind that are provided by a doctor, such as instructions to a patient.

The term "loading dose," as used herein, should be understood to mean a single dose or short duration regimen of a MNK-specific inhibitor or an inhibitor of an immunosuppression component or a chemotherapeutic agent having a dosage higher than the maintenance dose administered to a subject to, for example, rapidly increase the blood concentration level of the drug. In certain embodiments, a short duration regimen for use as described herein will be from one to about 14 days; from one to about seven days; from one to about three days; for about three days; for about two days; or for one day. In some embodiments, a "loading dose" can increase the blood concentration of a compound (e.g., MNK-specific inhibitor of this disclosure) to a therapeutically effective level. In some embodiments, a "loading dose" can increase the blood concentration of a compound (e.g., MNK-specific inhibitor of this disclosure) to a therapeutically effective level in conjunction with a maintenance dose of the compound. The "loading dose" can be administered once per day, or more than once per day (e.g., up to four times per day). In certain embodiments, a "loading dose" is administered once a day. In some embodiments, a loading dose will be an amount from two to about 100 times the maintenance dose; from about two to about ten times; from about two to about five times; or from about two times to about three times; about four times; or about five times. In other embodiments, a loading dose will be administered from one to about seven days; from one to about five days; from one to about three days; for one day; for about two days; for about three days, followed by a maintenance dosing protocol.

The term "maintenance dose," as used herein, will be understood to mean a dose that is serially administered (i.e.; at least twice), which is intended to either slowly raise blood concentration levels of the compound (e.g., MNK-specific inhibitor of this disclosure) to a therapeutically effective level, or to maintain such a therapeutically effective level over a desired period of time (e.g., hours, days, weeks, months, years). In certain embodiments, a maintenance dose is administered once or twice per day, and the daily maintenance dose is lower than the total daily loading dose.

As used herein the term "RNA interference agent" (RNAi agent), refers to a short single or double-stranded RNA polynucleotide capable of decreasing or inhibiting expression of a target gene, typically by cleavage of the target mRNA molecule. Non-limiting examples of RNAi agents include short interfering RNA (siRNA), short hairpin RNA (shRNA), microRNA (miRNA), and PIWI-interacting RNA (piRNA).

In any of the previously aforementioned embodiments, the method comprises administering a MNK-specific inhibitor and optionally a compound that induces or enhances an anti-cancer response. In certain embodiments, an induced or enhanced anti-cancer response is an anti-tumor response. In further embodiments, a therapy that induces or enhances an anti-cancer response is a vaccine, an inhibitor of an immunosuppression signal, a tyrosine kinase inhibitor, a cytotoxic agent, a chemotherapeutic agent, or any combination thereof. In certain embodiments, a therapy that induces or enhances an anti-cancer response is a chemotherapeutic agent, such as a B-Raf inhibitor, a MEK inhibitor, a VEGF inhibitor, or a VEGFR inhibitor.

As used herein, the term "B-Raf inhibitor" refers to any agent that reduces or inhibits the activity of B-Raf, also known as B-Raf protooncogene. B-Raf is a serine/threonine kinase that plays a role in regulating the MAP kinase/ERK signaling pathway, which affects cell division, differentiation, and secretion. Non-limiting examples of B-Raf inhibitors include sorafenib, vemurafenib, and dabrafenib. In certain embodiments, a MNK-specific inhibitor is used in combination with a B-Raf inhibitor, such as sorafenib, vemurafenib, dabrafenib, or any combination thereof. In further embodiments, a MNK-specific inhibitor is used in combination with a B-Raf inhibitor and a PD-1 specific antibody or binding fragment thereof. In still further embodiments, a MNK-specific inhibitor is used in combination with a B-Raf inhibitor and a PD-L1 specific antibody or binding fragment thereof. In yet further embodiments, a MNK-specific inhibitor is used in combination with a B-Raf inhibitor and a CTLA4 specific antibody or binding fragment thereof, or fusion protein. In yet further embodiments, a MNK-specific inhibitor is used in combination with a B-Raf inhibitor and a LAG3 specific antibody or binding fragment thereof, or fusion protein.

As used herein, the term "MEK inhibitor" refers to any agent that reduces or inhibits the activity of mitogen-activated protein kinase kinase enzymes MEK1 and/or MEK2. Non-limiting examples of MEK inhibitors include trametinib, selumetinib, binimetinib, PD-325901, cobimetinib, CI-1040, and PD035901. In certain embodiments, a MNK-specific inhibitor is used in combination with a MEK inhibitor, such as trametinib, selumetinib, binimetinib, PD-325901, cobimetinib, CI-1040, PD035901, or any combination thereof. In further embodiments, a MNK-specific inhibitor is used in combination with a MEK inhibitor and a PD-1 specific antibody or binding fragment thereof. In still further embodiments, a MNK-specific inhibitor is used in combination with a MEK inhibitor and a PD-L1 specific antibody or binding fragment thereof. In yet further embodiments, a MNK-specific inhibitor is used in combination with a MEK inhibitor and a CTLA4 specific antibody or binding fragment thereof, or fusion protein. In yet further embodiments, a MNK-specific inhibitor is used in combination with a MEK inhibitor and a LAG3 specific antibody or binding fragment thereof, or fusion protein.

As used herein, the term "vascular endothelial growth factor inhibitor" or "VEGF inhibitor" refers to any agent that reduces or inhibits the activity of VEGF. VEGF is a pro-angiogenic factor that promotes vasculogenesis, angiogenesis, and increases vascular permeability. VEGF may refer to VEGF-A, VEGF-B, VEGF-C, VEGF-D, VEGF-E, or any combination thereof. Non-limiting examples of VEGF inhibitors include bevacizumab, ranibizumab, AZD2171, cannbidiol, THC, or any combination thereof. In further embodiments, a MNK-specific inhibitor is used in combination with a VEGF inhibitor and a PD-1 specific antibody or binding fragment thereof. In still further embodiments, a MNK-specific inhibitor is used in combination with a VEGF inhibitor and a PD-L1 specific antibody or binding fragment thereof. In yet further embodiments, a MNK-specific inhibitor is used in combination with a VEGF inhibitor and a CTLA4 specific antibody or binding fragment thereof, or fusion protein. In yet further embodiments, a MNK-specific inhibitor is used in combination with a VEGF inhibitor and a LAG3 specific antibody or binding fragment thereof, or fusion protein.

As used herein, the term "vascular endothelial growth factor receptor inhibitor" or "VEGFR inhibitor" refers to any agent that inhibits the activity of VEGF-specific tyrosine kinase receptors VEGFR1, VEGFR2, VEGFR3, or any combination thereof. Non-limiting examples of VEGFR inhibitors include axitinib, sunitinib, vatalanib, sorafenib, GW-786034, CP-547632, AG-013736, lenvatinib, motesanib, pazopanib, regorafenib, ramucirumab, CDP-791, or any combination thereof. In further embodiments, a MNK-specific inhibitor is used in combination with a VEGFR inhibitor and a PD-1 specific antibody or binding fragment thereof. In still further embodiments, a MNK-specific inhibitor is used in combination with a VEGFR inhibitor and a PD-L1 specific antibody or binding fragment thereof. In yet further embodiments, a MNK-specific inhibitor is used in combination with a VEGFR inhibitor and a CTLA4 specific antibody or binding fragment thereof, or fusion protein. In yet further embodiments, a MNK-specific inhibitor is used in combination with a VEGFR inhibitor and a LAG3 specific antibody or binding fragment thereof, or fusion protein.

As used herein, the term "tyrosine kinase inhibitor" refers to any agent that inhibits a tyrosine kinase. Tyrosine kinase inhibitors include inhibitors that provide competitive ATP inhibition at the catalytic binding site of tyrosine kinase and allosteric inhibitors. Non-limiting examples of tyrosine kinase inhibitors include axitinib, imatinib, gefitinib, erlotinib, lapatinib, sorafenib, sunitinib, pazopanib, vandetanib, and dasatinib. In certain embodiments, a MNK-specific inhibitor is used in combination with a tyrosine kinase inhibitor, such as imatinib, gefitinib, erlotinib, lapatinib, sorafenib, sunitinib, pazopanib, vandetanib, dasatinib, or any combination thereof. In further embodiments, a MNK-specific inhibitor is used in combination with a tyrosine kinase inhibitor and a PD-1 specific antibody or binding fragment thereof. In still further embodiments, a MNK-specific inhibitor is used in combination with a tyrosine kinase inhibitor and a PD-L1 specific antibody or binding fragment thereof. In yet further embodiments, a MNK-specific inhibitor is used in combination with a tyrosine kinase inhibitor and a CTLA4 specific antibody or binding fragment thereof, or fusion protein. In yet further embodiments, a MNK-specific inhibitor is used in combination with a tyrosine kinase inhibitor and a LAG3 specific antibody or binding fragment thereof, or fusion protein.

As used herein the term "cytotoxic agent," refers to any agent that inhibits cell growth, inhibits cell proliferation, leads to cell death or the like. In certain embodiments, a MNK-specific inhibitor is used in combination with a cytotoxic agent, such as actinomycin, belomycin, plicamycin, mitomycin, doxorubicin, daunorubicin, epirubicin, idarubicin, pirarubucin, aclarubicin, mitoxantrone, or a combination thereof. An anti-mitotic agent, or anti-microtubule agent, may be paclitaxel, docetaxel, vinblastine, vincristine, vindesine, vinorelbine, or a combination thereof. In further embodiments, a MNK-specific inhibitor is used in combination with a cytotoxic agent and a PD-1 specific antibody or binding fragment thereof. In still further embodiments, a MNK-specific inhibitor is used in combination with a cytotoxic agent and a PD-L1 specific antibody or binding fragment thereof. In yet further embodiments, a MNK-specific inhibitor is used in combination with a cytotoxic agent and a CTLA4 specific antibody or binding fragment thereof, or fusion protein. In yet further embodiments, a MNK-specific inhibitor is used in combination with a cytotoxic agent and a LAG3 specific antibody or binding fragment thereof, or fusion protein.

In certain embodiments, immune modulation by a MNK-specific inhibitor is used with at least one anti-cancer agent. Anti-cancer agents include chemotherapeutic drugs. A chemotherapeutic agent includes, for example, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), or a DNA repair inhibitor. In further embodiments, a MNK-specific inhibitor is used in combination with a chemotherapeutic agent and a PD-1 specific antibody or binding fragment thereof. In still further embodiments, a MNK-specific inhibitor is used in combination with a chemotherapeutic agent and a PD-L1 specific antibody or binding fragment thereof. In yet further embodiments, a MNK-specific inhibitor is used in combination with a chemotherapeutic agent and a CTLA4 specific antibody or binding fragment thereof, or fusion protein. In yet further embodiments, a MNK-specific inhibitor is used in combination with a chemotherapeutic agent and a LAG3 specific antibody or binding fragment thereof, or fusion protein.

Chemotherapeutic agents include, for example, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (methotrexate, pemetrexed, mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones, eribulin and navelbine; epipidophyllotoxins (etoposide, teniposide); DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); DNA methyltransferase inhibitors (azacytidine); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkylsulfonates (busulfan), nitrosoureas (carmustine (BCNU) and analogs, streptozocin), triazenes (dacarbazine (DTIC)); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein, pomalidomide) and growth factor inhibitors (vascular endothelial growth factor (VEGF) inhibitors, such as ziv-aflibercept; fibroblast growth factor (FGF) inhibitors); inhibitors of apoptosis protein (IAP) antagonists (birinapant); histone deacetylase (HDAC) inhibitors (vorinostat, romidepsin, chidamide, panobinostat, mocetinostat, abexinostat, belinostat, entinostat, resminostat, givinostat, quisinostat, SB939); proteasome inhibitors (ixazomib); angiotensin receptor blocker; nitric oxide donors; anti-sense oligonucleotides; antibodies (trastuzumab, panitumumab, pertuzumab, cetuximab, adalimumab, golimumab, infliximab, rituximab, ocrelizumab, ofatumumab, obinutuzumab, alemtuzumab, abciximab, atlizumab, daclizumab, denosumab, efalizumab, elotuzumab, rovelizumab, ruplizumab, ustekinumab, visilizumab, gemtuzumab ozogamicin, brentuximb vedotin); chimeric antigen receptors; cell cycle inhibitors (flavopiridol, roscovitine, bryostatin-1) and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); PARP inhibitors (niraparib, olaparib); focal adhesion kinase (FAK) inhibitors (defactinib (VS-6063), VS-4718, VS-6062, GSK2256098); growth factor signal transduction kinase inhibitors (cediranib, galunisertib, rociletinib, vandetanib, afatinib, EGF816, AZD4547); c-Met inhibitors (capmatinib, INC280); ALK inhibitors (ceritinib, crizotinib); mitochondrial dysfunction inducers, toxins such as Cholera toxin, ricin, *Pseudomonas* exotoxin, *Bordetella*

*pertussis* adenylate cyclase toxin, or diphtheria toxin, and caspase activators; and chromatin disruptors.

In certain embodiments, a chemotherapeutic is a B-Raf inhibitor, a MEK inhibitor, a VEGF inhibitor, a VEGFR inhibitor, a tyrosine kinase inhibitor, an anti-mitotic agent, or any combination thereof. In a specific embodiment, the chemotherapeutic is vemurafenib, dabrafenib, trametinib, cobimetinib, sunitinib, erlotinib, paclitaxel, docetaxel, or any combination thereof.

In certain embodiments, a therapy that induces or enhances an anti-cancer response, for example, a vaccine, an inhibitor of an immunosuppression signal, a B-Raf inhibitor, a MEK inhibitor, a VEGF inhibitor, a VEGFR inhibitor, a tyrosine kinase inhibitor, a cytotoxic agent, a chemotherapeutic, or any combination thereof, is used in combination with a MNK-specific inhibitor in the immune modulation methods described herein, wherein the therapy that induces or enhances an anti-cancer response does not antagonize, reduce, diminish, or decrease the inhibitory activity of a MNK-specific inhibitor on one or more inhibitory immune checkpoint molecules. An antagonistic combination with a MNK-specific inhibitor may be ascertained by measuring the level of T cell activation (e.g., as described in Example 2 herein) as a readout of the inhibitory activity of a MNK-specific inhibitor, with and without the therapy that induces or enhances anti-cancer response, on one or more inhibitory immune checkpoint molecules. In certain embodiments, a combination of a MNK-specific inhibitor and a therapy that induces or enhances anti-cancer response will not antagonize the inhibitory activity of the MNK-specific inhibitor against one or more inhibitory immune checkpoint molecules or will only decrease the inhibitory activity of the MNK-specific inhibitor against one or more inhibitory immune checkpoint molecules by less than about 25%, 20%, 15%, 10%, 5%, 2%, 1%, 0.5%, 0.25%, or 0.1%.

In the context of infection or infectious disease, immune modulation by a MNK-specific inhibitor is used in combination with antiviral agents (e.g., anti-HIV agents), antibiotic agents, antimicrobial agents, anti-parasitic agents, or anti-fungal agents. Examples of anti-HIV drugs include, for example, reverse transcriptase inhibitors (e.g., AZT, ddI, 3TC, and d4T), protease inhibitors (e.g., saquinavir mesylate, ritonavir, nelfinavir mesylate, amprenavir, delavirdine mesylate, saquinavir, and lopinavir/ritonavir) or CCR5 receptor antagonists. Antiviral agents include, for example, anti-herpesvirus agents, anti-influenza virus agents, interferon-α and β, or various immunoglobulins.

Immune modulation by a MNK-specific inhibitor may be used together with an anti-viral vaccine, an anti-bacterial vaccine, an anti-fungal vaccine, an anti-parasitic vaccine, or made as a formulation with such vaccines. Vaccines for infectious disease include, for example, poliovaccine, measles vaccine, Japanese encephalitis vaccine, BCG vaccine, triple vaccine, mumps virus vaccine, varicella virus vaccine, influenza vaccine, hepatitis A vaccine, hepatitis B vaccine, HIV vaccine, malaria vaccine, and cholera vaccine.

A "subject in need thereof" refers to a subject at risk of, or suffering from, a disease, disorder or condition (e.g., hyperproliferative disorder like cancer, chronic infection) that is amenable to treatment or amelioration with a compound or a composition thereof provided herein. Subjects in need of administration of therapeutic agents as described herein include subjects suspected of having a cancer, subjects presenting with an existing cancer, subjects receiving a cancer vaccine, subjects suspected of being infected with an infectious agent, subjects presenting with an infection or infectious disease, or subjects receiving a vaccine against an infectious agent. A subject may be any organism capable of developing cancer or being infected, such as humans, pets, livestock, show animals, zoo specimens, or other animals. For example, a subject may be a human, a non-human primate, dog, cat, rabbit, horse, or the like. In certain embodiments, a subject in need is a human. In particular embodiments, a subject in need has a disease, such as cancer or chronic infection, associated with immune resistance.

In any of the aforementioned embodiments, a pharmaceutical composition comprising a MNK-specific inhibitor (e.g., as compound of structure (I)) is administered to a subject in an amount sufficient to inhibit MNK-specific activity and reduce immunosuppression, and preferably with acceptable toxicity to the same. Appropriate concentrations and dosages can be readily determined by one skilled in the art.

A MNK-specific inhibitor, or a pharmaceutically acceptable salt thereof, is administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

"Effective amount" or "therapeutically effective amount" refers to that amount of a MNK-specific inhibitor described herein which, when administered to a mammal (e.g., human), is sufficient to effect relief from immune suppression, as defined herein, to aid in treating a disease in the mammal, such as a human. The amount of a MNK-specific inhibitor that constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure. When referring to an individual active ingredient, administered alone, a therapeutically effective dose refers to that ingredient alone. When referring to a combination, a therapeutically effective dose refers to combined amounts of the active ingredients that result in the therapeutic effect, whether administered serially, concurrently or simultaneously.

The therapeutic MNK-specific inhibitors and pharmaceutical compositions thereof that increase the activity of an immune cell; induce, enhance, or prolong an immune response; stimulate an antigen-specific T cell response; inhibit an immunosuppressive signaling pathway; promote endogenous anti-cancer or anti-infectious agent immunity; or inhibit immune resistance of cancer cells or infectious agents/infected cells provided herein are administered to a subject who has or is at risk of developing a cancer, infection, or infectious disease at a therapeutically effective amount or dose. Such a dose may be determined or adjusted depending on various factors including the specific therapeutic agents or pharmaceutical compositions, the routes of administration, the subject's condition, that is, stage of the disease, viral/bacterial/fungal/parasite load, severity of symptoms caused by the disease, general health status, as well as age, gender, and weight, and other factors apparent to a person skilled in the medical art. Similarly, the dose of the therapeutic for treating a disease or disorder may be determined according to parameters understood by a person skilled in the medical art.

An example where monotherapy may be sufficient as an anti-cancer therapy is in the context of a patient with a strong, endogenous (pre-existing) anti-cancer immune response. For example, a tumor may have a large population of antigen specific tumor infiltrating lymphocytes (TILs). But, an active anti-cancer immune response within the tumor microenvironment may induce tumor cells and tumor-associated macrophages to express immune inhibitory signals (e.g., PD-L1) that down-modulate the anti-cancer immune response. Addition of an inhibitor of an immunosuppression signal, such as a MNK-specific inhibitor, may inhibit the tumor's adaptive immune resistance mechanism and allow tumor regression via the endogenous anti-cancer immune response (e.g., TILs). In certain embodiments, a monotherapy that promotes an anti-cancer response may be a MNK-specific inhibitor, a vaccine, a B-Raf inhibitor, a MEK inhibitor, a VEGF inhibitor, a VEGFR inhibitor, a tyrosine kinase inhibitor, a cytotoxic agent, a chemotherapeutic, or any combination thereof. In certain embodiments, an inhibitor of an immunosuppression signal component is an inhibitor of MNK, PD-1, PD-L1, PD-L2, CTLA4, CD80, CD86, B7-H3, B7-H4, HVEM, BTLA, KIR, LAG3, GAL9, TIM3, 2B4, adenosine, A2aR, TGFβ, IL-10, IL-35, arginase, IDO, or any combination thereof.

In other examples, a combination therapy may be useful in the context of a patient with a weak, endogenous anti-cancer immune response. For example, a tumor environment may have lower numbers of TILs because the tumor might be less immunogenic. A therapy that induces or enhances an anti-cancer response de novo can promote or increase the endogenous anti-cancer immune response. But, as with the single therapy, the efficacy of this anti-cancer immune response may be limited by up-regulation of immunosuppression signal components (e.g., PD-L1). For example, combining a therapy that induces or enhances an anti-cancer response ("prime") with an inhibitor of an immunosuppression signal ("boost") may induce promote or improve the likelihood of tumor regression. Alternatively, a combination therapy may comprise an inhibitor of an immunosuppression signal component ("prime") with an agent that induces or enhances an anti-cancer response ("boost") may induce or promote or improve the likelihood of tumor regression. Combining a therapy that induces or enhances an anti-cancer response ("prime") with an inhibitor or down-regulator of an immunosuppression signal component ("boost") may induce tumor regression by allowing an endogenous anti-tumor immune response to function as such. In certain embodiments, a combination therapy that induces or enhances or promotes an anti-cancer response may be a MNK-specific inhibitor used with one or more of the following: a vaccine, a B-Raf inhibitor, a MEK inhibitor, a VEGF inhibitor, a VEGFR inhibitor, a tyrosine kinase inhibitor, a cytotoxic agent, a chemotherapeutic, or any combination thereof. In certain embodiments, an inhibitor of an immunosuppression signal component is an inhibitor of MNK, PD-1, PD-L1, PD-L2, CTLA4, CD80, CD86, B7-H3, B7-H4, HVEM, BTLA, KIR, LAG3, GAL9, TIM3, 2B4, adenosine, A2aR, TGFβ, IL-10, IL-35, arginase, or IDO. In certain embodiments, a combination therapy comprises a "prime" and a "boost" treatment, wherein each treatment is administered to a subject simultaneously or concurrently. In other embodiments, the "boost" treatment is administered sequentially after the "prime" treatment.

Generally, a therapeutic agent is administered at a therapeutically effective amount or dose. A therapeutically effective amount or dose will vary according to several factors, including the chosen route of administration, formulation of the composition, patient response, severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. In addition, a patient may be given a plurality of doses over a determined period of time and in particular time increments (such as daily, weekly, biweekly, monthly, quarterly, biannually, annually or the like). Determination of an effective amount or dosing regimen is well within the capability of those skilled in the art.

When referring to a combination, a therapeutically effective dose refers to combined amounts of the active ingredients that result in the therapeutic effect, whether administered serially or simultaneously (in the same formulation or concurrently in separate formulations). The most effective doses may generally be determined using experimental models and/or clinical trials. Design and execution of preclinical and clinical studies for a therapeutic agent (including when administered for prophylactic benefit) described herein are well within the skill of a person skilled in the relevant art.

The route of administration of a therapeutic agent can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art.

EXAMPLES

Example 1

MNK-Specific Inhibition Decreases Expression of Immune Checkpoint Receptors and Ligands Upon activation of T cell receptor (TCR) signaling, T cells proliferate, produce cytokines (e.g., IL-2) and induce the expression of immune checkpoint receptors. Programmed death 1 (PD-1) is an inhibitory checkpoint receptor expressed on the surface of activated T cells, as well as on myeloid cells. The ligand for PD-1, programmed death ligand-1 (PD-L1, B7-H1/CD274) is not expressed by T cells or normal epithelial cells, but is expressed by antigen presenting cells and overexpressed in several cancers. Interaction of PD-1 with PD-L1 results in an anti-proliferative effect on T cells and ultimately T cell exhaustion and apoptosis. To study the role of MNK in activated T cells and tumor cells, the effect of a MNK-specific inhibitor on molecules of immune checkpoint control was examined.

PD-1 (CD279) Expression

To examine the effect of MNK-specific inhibitors on PD-1 expression, Jurkat cells (Clone E6.1, ATCC, transformed T cells) were used, which express PD-1 when activated through T cell receptor (TCR) signaling. Briefly, Jurkat cells were grown in 1×RPMI with 1× Pen/Strep, and 10% FBS, then about $3 \times 10^6$ Jurkat cells were activated in presence of 1 μg/mL PHA (Sigma) and 50 ng/mL PMA (Sigma). Test Cells were treated simultaneously with various concentrations of MNK-specific inhibitor Compound 107 (0, 0.01, 0.1, 1, 3 and 10 μM). After 48 hours, culture supernatants were harvested and examined via sandwich ELISA for the presence of IL-2 using human IL-2 ELISA DuoSet® (R&D Systems, Minneapolis, Minn.). The level of PD-1 on Jurkat cells was examined by incubating cells with fixable dead cell stain (1:20,000; BD Biosciences, San Jose, Calif.) for 15 minutes at 4° C., washed twice with flow staining buffer (1×PBS, 4% FBS and 1 mM EDTA), incubated with human FcR block, then contacted with allophycocyanin (APC) conjugated anti-PD-1 antibody (Biolegend, San Diego, Calif.) for 30 minutes at 4° C., washed two times with flow buffer, and finally cells were fixed with fixation buffer for 20 minutes at 4° C. After fixation, cells were washed twice with flow buffer and re-suspended in flow buffer and assessed for fluorescence using BD Accuri C6 flow cytometer. Data were analyzed using the C6 cytometer software (BD Biosciences, San Jose, Calif.).

Figure 1B:
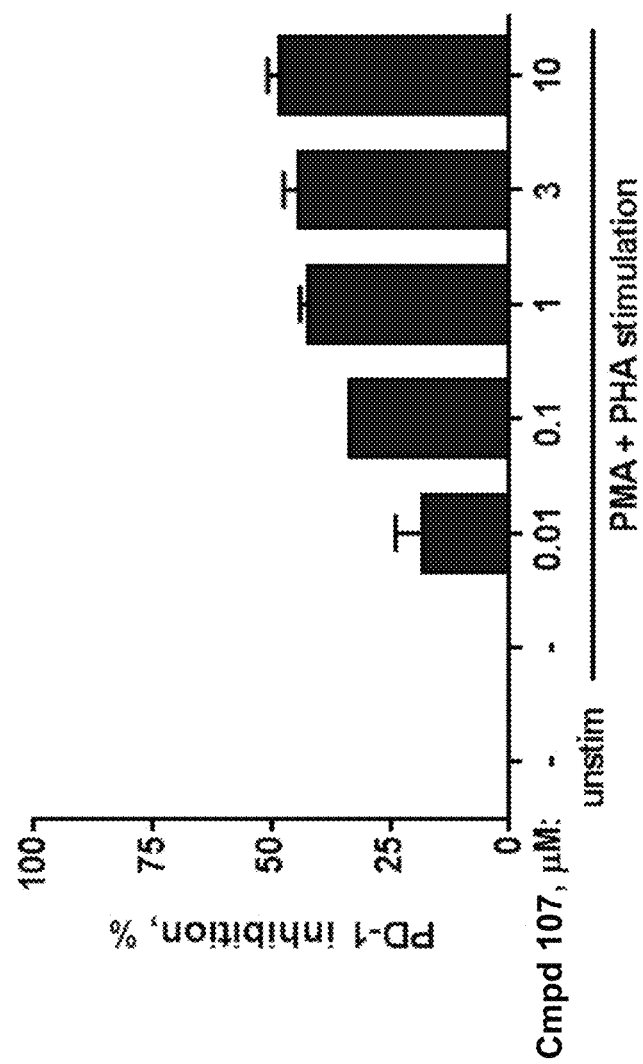
Figure 1C:
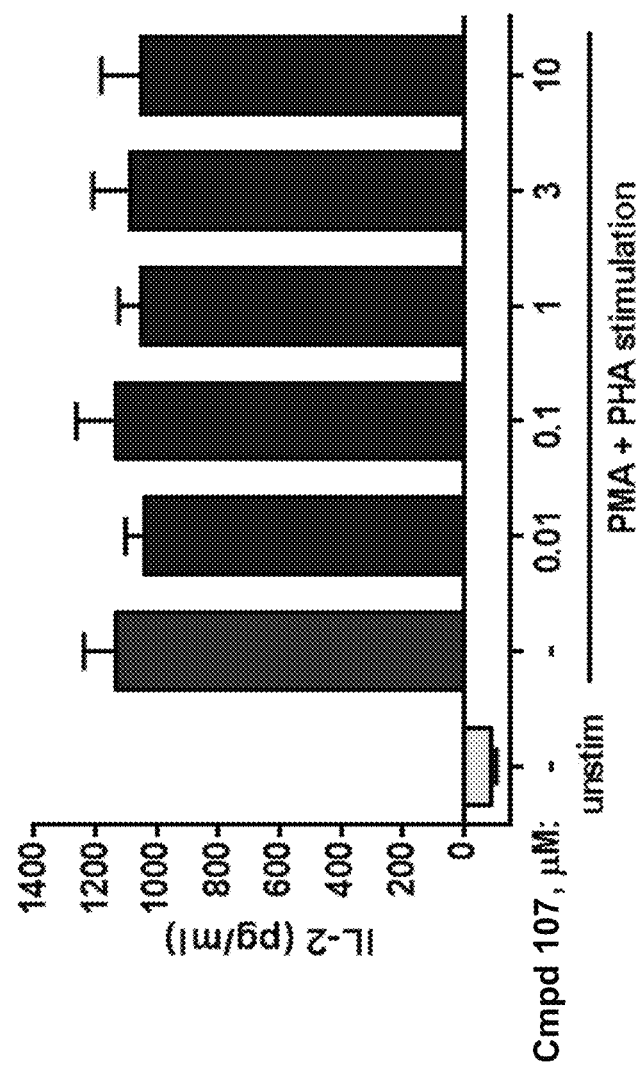
Figure 1D:
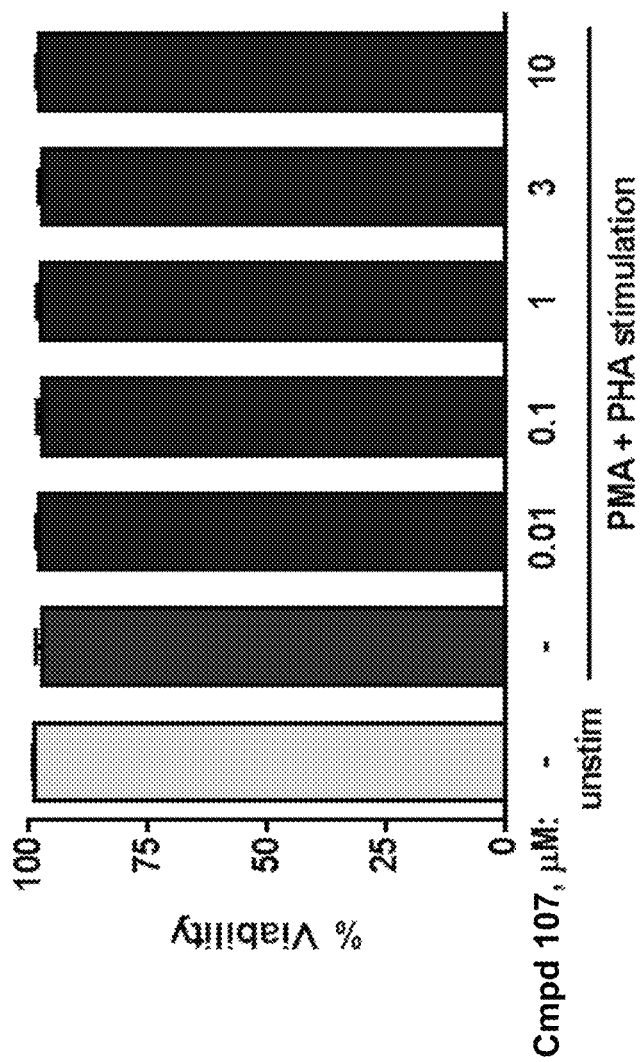
Figure 2A:
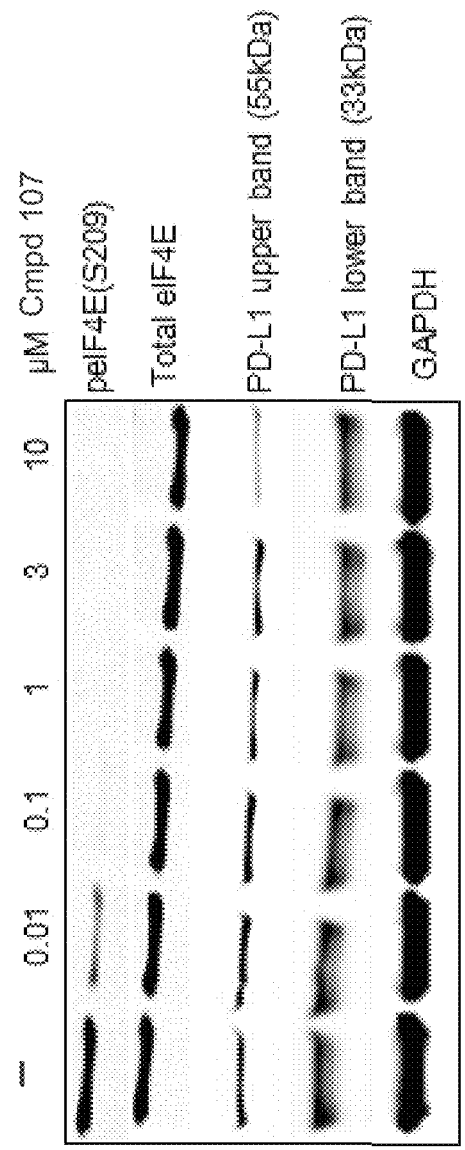
FIGS. 2A to 2E show that the expression of PD-L1 detected by western blot (A) in MDA-MB-231, a metastatic human breast cancer cell line, (B) in HBL-1, a human activated B-cell-like (ABC) subtype of diffuse large B-cell lymphoma (DLBCL) cell line, (C) in A549, a human lung adenocarcinoma epithelial cell line, (D) in MDA-MB-361, a human breast adenocarcinoma cell line, and (E) AMO-1, a human plasmacytoma cell line, is reduced in a dose dependent manner in the presence of MNK-specific inhibitor Compound 107 (used at 0.01, 0.1, 1, 3 and 10 μM) as compared to the DMSO vehicle control (column labeled '-').
Figure 2B:
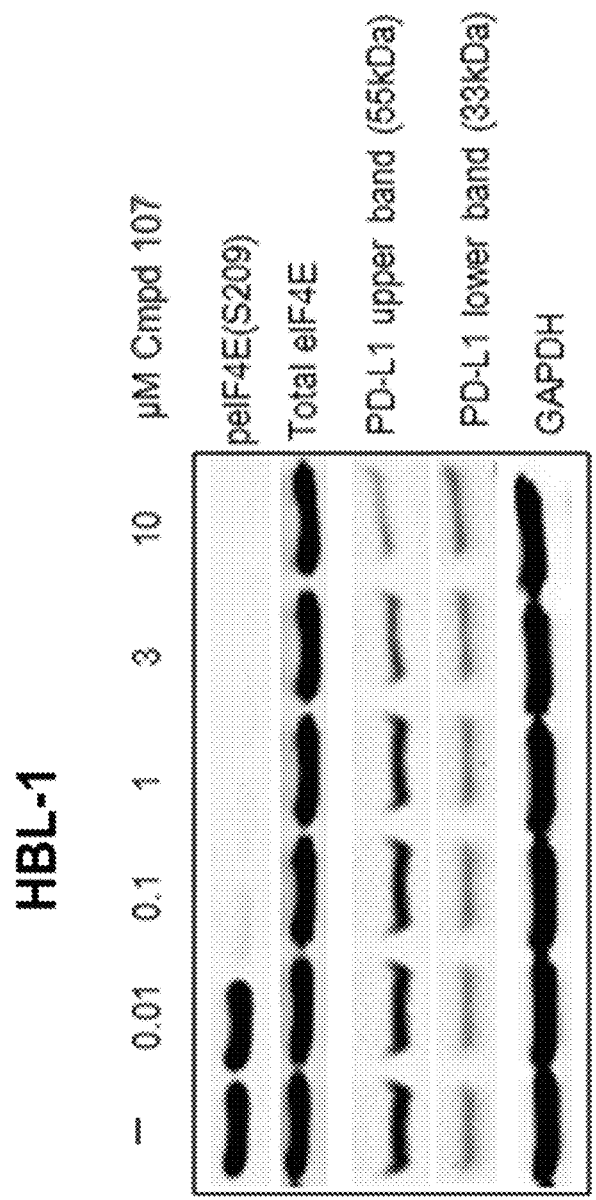
Figure 2C:
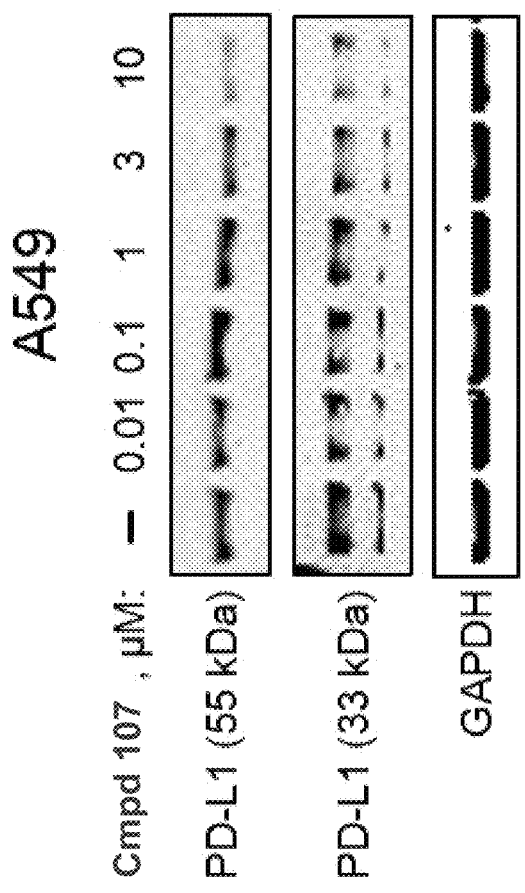
Figure 2D:
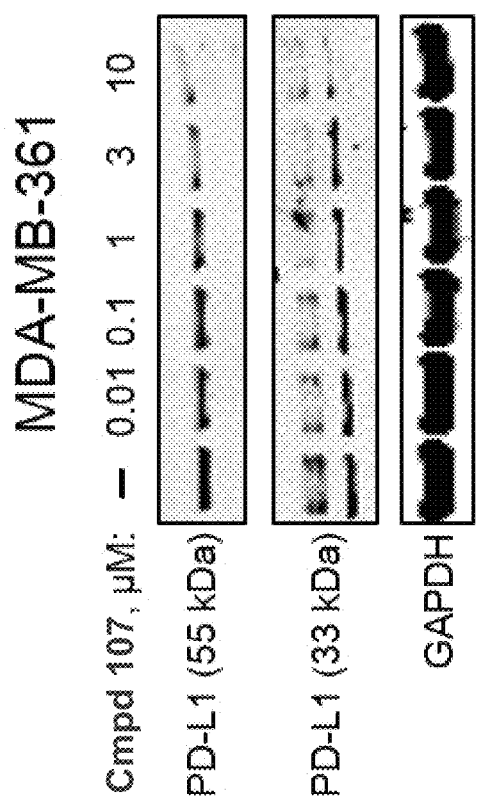
Figure 2E:
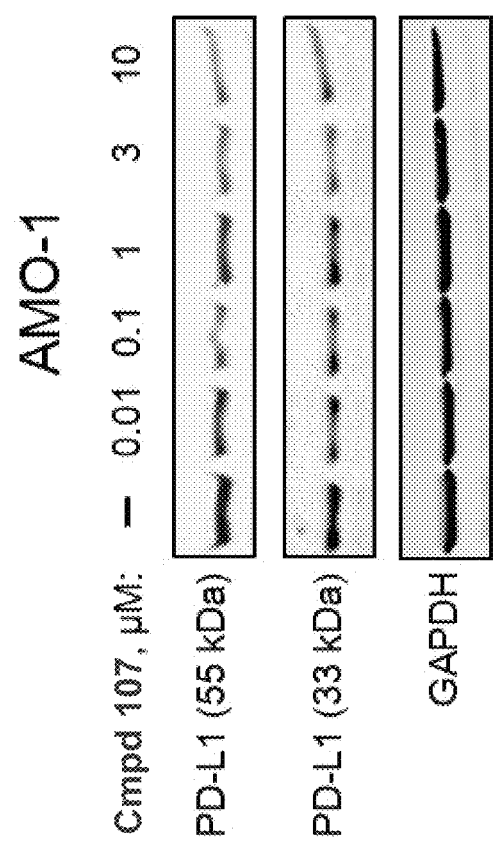

As shown in FIGS. 1A and 1C, activation of Jurkat T cells with PHA and PMA induced the expression of PD-1 on the cell surface of about 25-30% of the stimulated Jurkat cells as compared to uninduced cells (Unstim) and induced a 1,000-fold increase in IL-2 cytokine production, respectively. Treatment of PHA/PMA activated Jurkat T cells with the MNK-specific inhibitor Compound 107 resulted in a concentration dependent decrease in the expression of the immune inhibitory receptor PD-1, up to a 50% reduction at the highest concentration as compared to control (see FIG. 1B). In addition, FIG. 1C shows that this reduction of PD-1 was not due to a block in Jurkat T cell activation per se since MNK-specific inhibition by Compound 107 did not alter cytokine production as measured by IL-2 levels (see FIG. 1C). Lastly, MNK-specific inhibition with Compound 107 had no effect on cell viability (FIG. 1D).

In fact, various different MNK-specific inhibitors in the Jurkat T cell assay showed the ability to downregulate immune checkpoint inhibitors without affecting cell viability. Such compounds are summarized in Table 2A.

TABLE 2A

Effect of Various MNK-Specific Inhibitors on Immune Checkpoint Expression and Jurkat T Cell Viability

| Compound | Structure | % PD-1 + Inhibition* | Cell Death† |
|---|---|---|---|
| 98 | 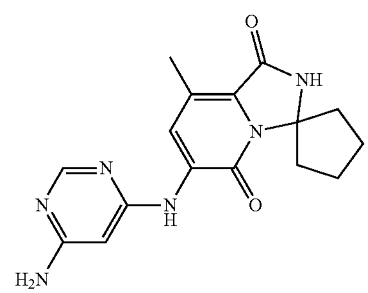 [SMILES: Cc1cc(Nc2cc(N)ncn2)c(=O)n2c1C(=O)NC21CCCC1] | +++ | − |
| 107 | 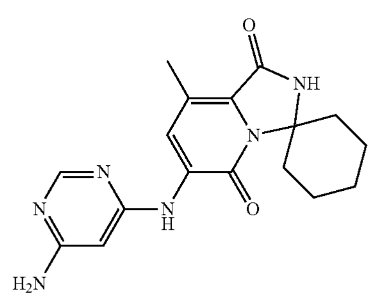 [SMILES: Cc1cc(Nc2cc(N)ncn2)c(=O)n2c1C(=O)NC21CCCCC1] | +++ | − |
| 440 | 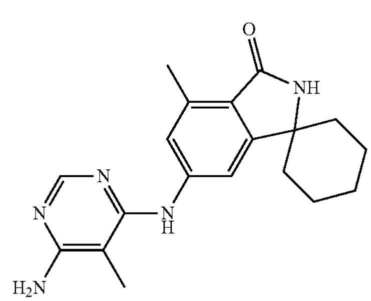 | ++++ | − |

TABLE 2A-continued
Effect of Various MNK-Specific Inhibitors on Immune Checkpoint Expression and Jurkat T Cell Viability
| Compound | Structure | % PD-1 + Inhibition* | Cell Death† |
|---|---|---|---|
| 462 | 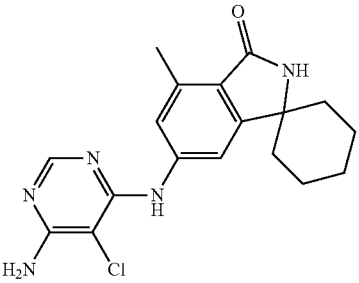 [SMILES: Cc1cc(Nc2ncnc(N)c2Cl)cc2c1C(=O)NC21CCCCC1] | ++++ | + |
| 474 | 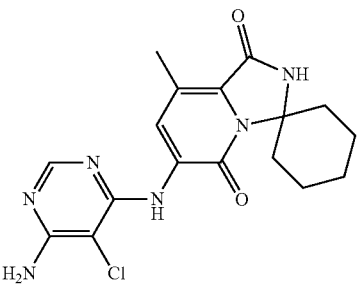 [SMILES: Cc1cc(Nc2ncnc(N)c2Cl)c(=O)n2c1C(=O)NC21CCCCC1] | +++ | − |
| 590 | 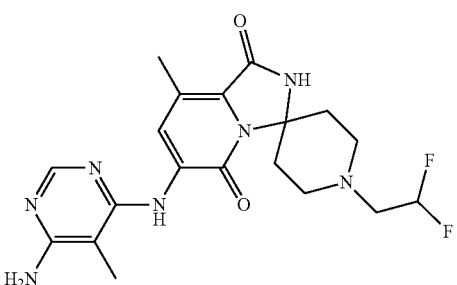 | ++ | − |
| 611 | 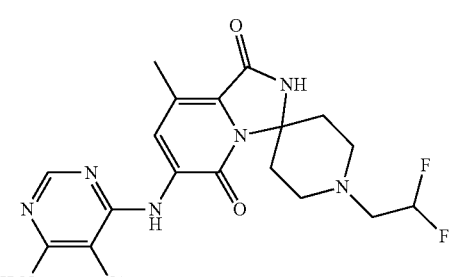 | ++ | − |
| 622 | 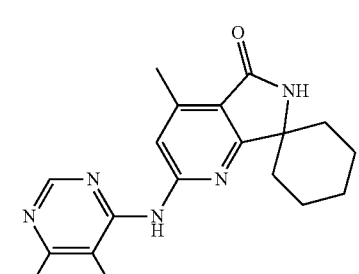 | ++++ | − |

TABLE 2A-continued

Effect of Various MNK-Specific Inhibitors on Immune Checkpoint Expression and Jurkat T Cell Viability

| Compound | Structure | % PD-1 + Inhibition* | Cell Death† |
|---|---|---|---|
| 624 | 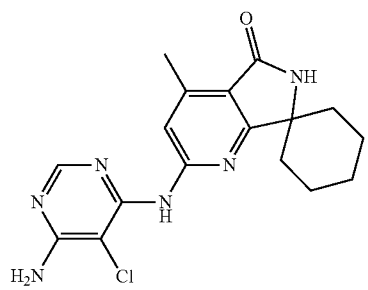 [SMILES: Cc1cc(Nc2ncnc(N)c2C)nc2c1C(=O)NC21CCCCC1] | ++++ | + |
| 626 | 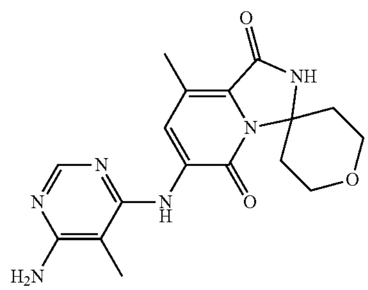 [SMILES: Cc1cc(Nc2ncnc(N)c2C)c(=O)n2c1C(=O)NC21CCOCC1] | ++ | − |
| 637 | 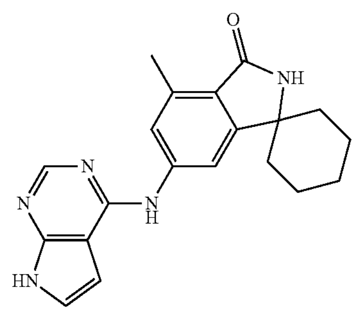 [SMILES: Cc1cc(Nc2ncnc3[nH]ccc23)cc2c1C(=O)NC21CCCCC1] | ++++ | ++ |
| 652 | 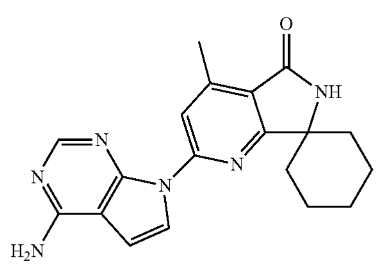 [SMILES: Cc1cc(-n2ccc3c(N)ncnc32)nc2c1C(=O)NC21CCCCC1] | ++++ | − |
| 750 | 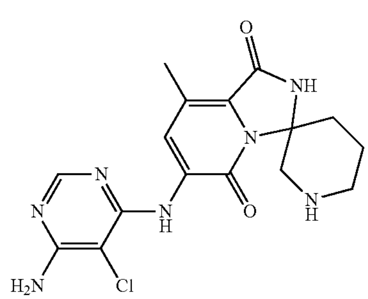 [SMILES: Cc1cc(Nc2ncnc(N)c2Cl)c(=O)n2c1C(=O)NC21CCCNC1] | +++ | − |

TABLE 2A-continued

Effect of Various MNK-Specific Inhibitors on Immune Checkpoint Expression and Jurkat T Cell Viability

| Compound | Structure | % PD-1 + Inhibition* | Cell Death† |
|---|---|---|---|
| 752 | 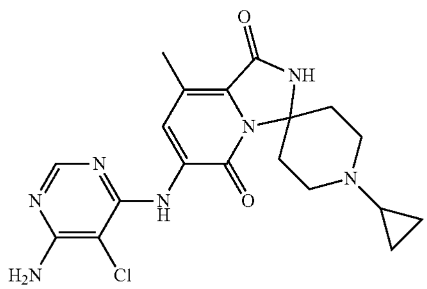 [SMILES: Cc1cc(Nc2ncnc(N)c2Cl)c(=O)n2c1C(=O)NC21CCN(C2CC2)CC1] | − | − |
| 753 | 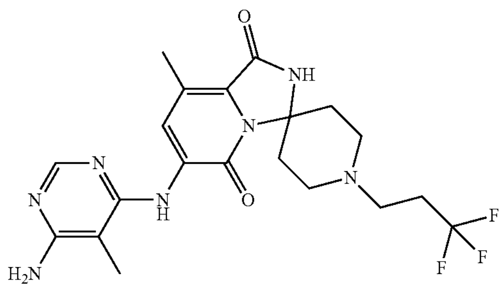 [SMILES: Cc1cc(Nc2ncnc(N)c2C)c(=O)n2c1C(=O)NC21CCN(CCC(F)(F)F)CC1] | − | − |
| 775 | 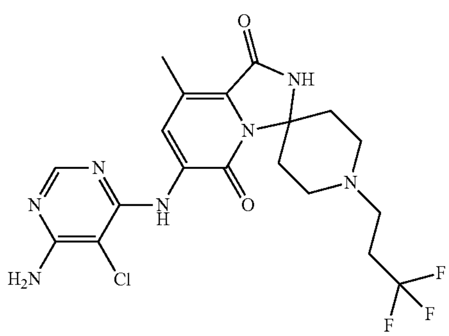 [SMILES: Cc1cc(Nc2ncnc(N)c2Cl)c(=O)n2c1C(=O)NC21CCN(CCC(F)(F)F)CC1] | − | − |
| 776 | 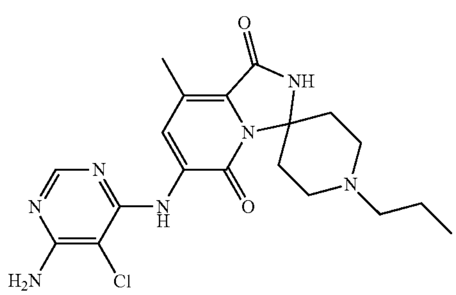 [SMILES: CCCN1CCC2(CC1)NC(=O)c1c(C)cc(Nc3ncnc(N)c3Cl)c(=O)n12] | + | − |
| 827 | 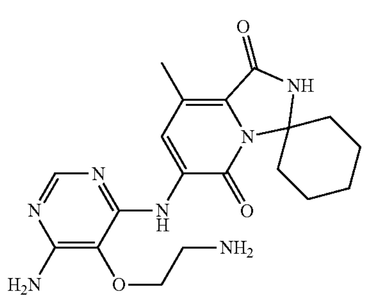 [SMILES: Cc1cc(Nc2ncnc(N)c2OCCN)c(=O)n2c1C(=O)NC21CCCCC1] | ++ | − |

TABLE 2A-continued

Effect of Various MNK-Specific Inhibitors on Immune Checkpoint Expression and Jurkat T Cell Viability

| Compound | Structure | % PD-1 + Inhibition* | Cell Death† |
|---|---|---|---|
| 917 | 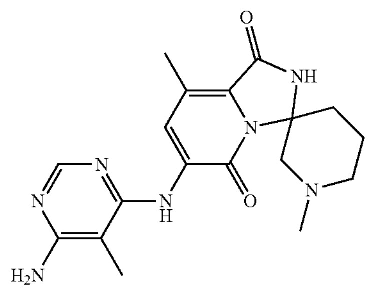 [SMILES: Cc1cc(Nc2ncnc(N)c2C)c(=O)n2c1C(=O)NC21CCCN(C)C1] | ++ | + |
| 969 | 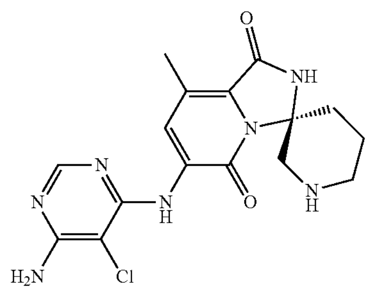 [SMILES: Cc1cc(Nc2ncnc(N)c2Cl)c(=O)n2c1C(=O)N[C@]21CCCNC1] | +++ | − |
| 970 | 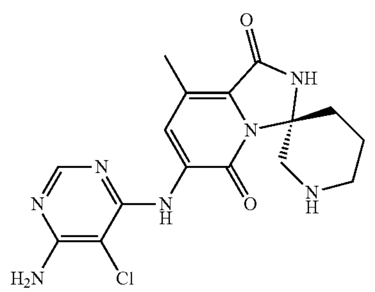 [SMILES: Cc1cc(Nc2ncnc(N)c2Cl)c(=O)n2c1C(=O)N[C@@]21CCCNC1] | +++ | − |
| 1008 | 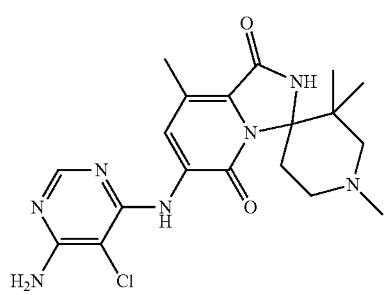 [SMILES: Cc1cc(Nc2ncnc(N)c2Cl)c(=O)n2c1C(=O)NC21CCN(C)CC1(C)C] | +++ | ++ |
| 1031 | 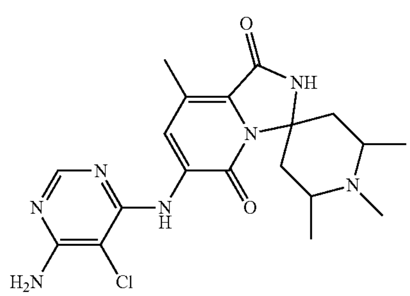 [SMILES: Cc1cc(Nc2ncnc(N)c2Cl)c(=O)n2c1C(=O)NC21CC(C)N(C)C(C)C1] | +++ | +++ |

TABLE 2A-continued

Effect of Various MNK-Specific Inhibitors on Immune Checkpoint Expression and Jurkat T Cell Viability

| Compound | Structure | % PD-1 + Inhibition* | Cell Death† |
|---|---|---|---|
| 1053 | 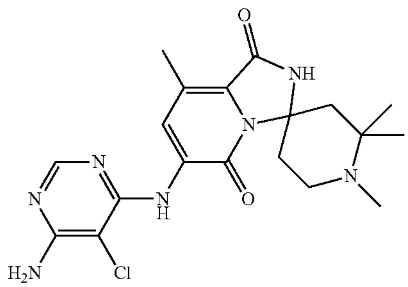 [SMILES: Cc1cc(Nc2ncnc(N)c2Cl)c(=O)n2c1C(=O)NC21CCN(C)C(C)(C)C1] | + | − |
| 1090 | 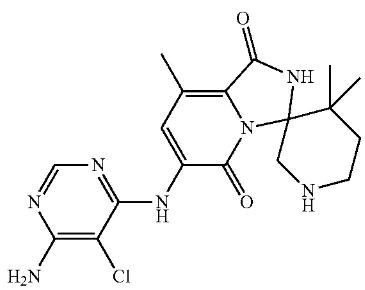 | +++ | + |
| 1091 | 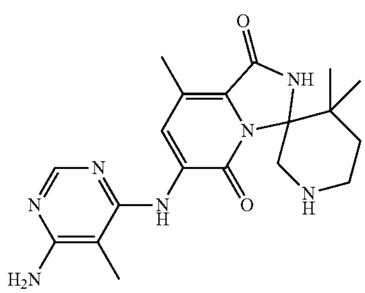 [SMILES: Cc1cc(Nc2ncnc(N)c2C)c(=O)n2c1C(=O)NC21CNCCC1(C)C] | ++ | − |
| 1092 | 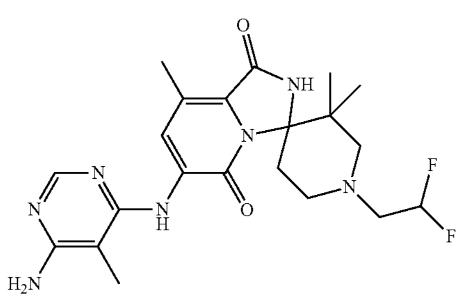 [SMILES: Cc1cc(Nc2ncnc(N)c2C)c(=O)n2c1C(=O)NC21CCN(CC(F)F)CC1(C)C] | ++ | − |

*− = 0-10%; + = 10-25%; ++ = 25-50%; +++ = 50-75%; ++++ = 75-100%
†− = 0-10%; + = 10-25%; ++ = 25-50%; +++ = 50-75%; ++++ = 75-100%

TABLE 2B

Effect of Non-Specific MNK Inhibitors on Immune Checkpoint Expression and Jurkat T Cell Viability

| Compound | Structure | % PD-1 + Inhibition* | Cell Death† |
|---|---|---|---|
| trans-3-{[3-(4-fluoro-1-benzofuran-2-yl)imidazo[1,2-b]pyridazin-6-yl]oxy}-cyclobutanamine[a] | 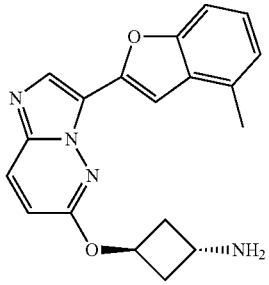 [SMILES: Cc1cccc2oc(-c3cnc4ccc(O[C@H]5C[C@H](N)C5)nn34)cc12] | ++ | ++++ |
| LY2801653[b] | 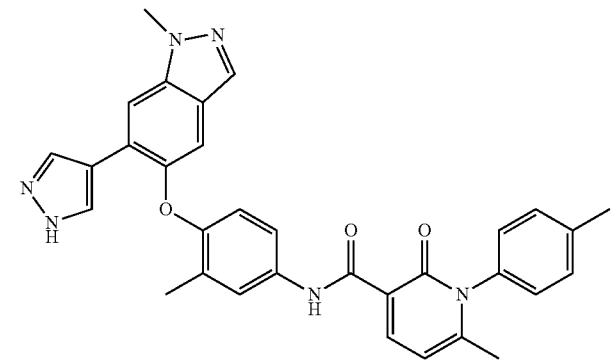 [SMILES: Cc1ccc(-n2c(C)ccc(C(=O)Nc3ccc(Oc4cc5cnn(C)c5cc4-c4cn[nH]c4)c(C)c3)c2=O)cc1] | − | ++ |

*− = 0-10%; + = 10-25%; ++ = 25-50%; +++ = 50-75%; ++++ = 75-100%
†− = 0-10%; + = 10-25%; ++ = 25-50%; +++ = 50-75%; ++++ = 75-100%
[a]See WO 2013/034570;
[b]See Yan et al., Invest. New Drugs 31:833, 2013

While some of the specific MNK inhibitor compounds had little anti-PD-1 activity and some had an effect on cell viability, the majority of the compounds tested were capable of translationally downregulating immune checkpoint inhibitors with no detectable toxicity, whereas non-specific MNK inhibitors were either toxic or had no effect on immune checkpoint expression (PD-1).

PD-L1 (B7-H1, CD274) Expression

PD-L1, the ligand for PD-1, has been shown to be upregulated in a variety of tumor types (Mahoney et al., Nat. Rev. Drug Discov. 14:561, 2015). To examine whether specific inhibition of MNK had an effect on PD-L1 expression, several tumor cell lines that constitutively express PD-L1, including and cells were treated with the indicated concentrations of eFT508 or vehicle (DMSO) for 48 hours. Cells were lysed in 1×RIPA lysis buffer (Millipore, Billerica Mass.) supplemented with protease and phosphatase inhibitors (Biotool, Houston Tex.). Protein concentrations in cell lysates were quantitated by BCA protein assay (Thermo-Fisher, Waltham Mass.) and equal amounts of total protein were resolved by SDS-PAGE, immunoblotted with anti-PD-L1 and GAPDH antibodies (Santa Cruz Biotechnology, Dallas Tex.), and visualized by LI-COR Odyssey imager (LI-COR, Lincoln Nebr.). A549 (human lung adenocarcinoma epithelial cell line), HBL-1 (human activated B-cell-like (ABC) subtype of diffuse large B-cell lymphoma (DLBCL) cell line), AMO-1 (human plasmacytoma cell line), MDA-MB-361 (human breast adenocarcinoma cell line), and MDA-MB-231 (metastatic human breast cancer cell line) were tested. HBL-1 and AMO-1 cells were separately grown in 1×RPMI with 1× Pen/Strep and 10% fetal bovine serum FBS, and then 2-4×10⁶ HBL-1 or AMO-1 cells in fresh media were separately contacted with vehicle only (DMSO) or MNK-specific inhibitor Compound 107 at various concentrations (at 0.01, 0.1, 1, 3 or 10 μM) for 48 hours. A549 cells, MDA-MB-361 cells, and MDA-MB-231 cells were separately grown in 1×DMEM with 1× Pen/Strep and 10% FBS, and then 2-4×10⁶ A549, MDA-MB-361 or MDA-MB-231 cells in fresh media were separately contacted with vehicle only (DMSO) or MNK-specific inhibitor Compound 107 at various concentrations (at 0.01, 0.1, 1, 3 or 10 μM) for 48 hours. Whole cell lysates were prepared using 1× radioimmunoprecipitation assay (RIPA) buffer (Millipore, Billerica, Mass.) supplemented with 1× protease and phosphatase inhibitors (BioTool, Houston, Tex.). Protein concentration was estimated with BCA protein assay reagent (Thermo Fisher, Waltham, Mass.), with about 25 μg total protein resolved on 4-12% Bis-Tris SDS-PAGE gels (Invitrogen) and probed by Western blot with the following antibodies: (a) anti-PD-L1 (EMD Milipore, Billerica, Mass.) to detect PD-L1, (b) anti-phospho eIF4E (Santa Cruz Biotechnology, Dallas, Tex.) to detect phosphorylated eIF4e, and (c) anti-GAPDH antibodies (Santa Cruz Biotechnology, Dallas, Tex.) to detect GAPDH as an internal control. Protein levels detected by Western blot were quantified using Image Studio™ Lite Software (LI-COR, Lincoln, Nebr.).

FIGS. 2A to 2E show that all cell lines tested showed expression of the highly glycosylated form of PD-L1 (upper band, 55 kDa) as well as lower glycosylated form of PD-L1 (33 kDa). MNK-specific inhibition resulted in about a 30-40% reduction of the highly glycosylated PD-L1 protein (upper band) in all the cancer cell types tested: (A) breast cancer MDA-MB-231 cells; (B) B cell lymphoma HBL-1 cells; (C) lung adenocarcinoma A549 cells; (D) breast adenocarcinoma MDA-MB-361 cells; and (E) multiple myeloma AMO-1 cells. As a positive control, inhibition of MNK was confirmed by detecting the abrogation of eIF4E phosphorylation since eIF4E is a direct target of MNK enzymatic activity (data shown in FIGS. 2A and 2B only), which can impact regulation of gene expression via cap dependent translation.

Conclusion

These data demonstrate that MNK affects the expression of immune checkpoint system molecules in both effector cells (e.g., PD-1 in T cells) and target cells (e.g., PD-L1 in antigen presenting cells). The data also indicate that specific inhibition of MNK function will remove inhibitory immune checkpoint signaling without diminishing T cell function since the presence of a MNK-specific inhibitor had minimal to no effect on cytokine (e.g., IL-2) production and on cell viability.

Example 2

MNK-Specific Inhibition Effect on Expression of Immune Checkpoint Receptors on Primary T Cells To examine whether specific inhibition of MNK has an effect on PD-1 and LAG3 expression in patient T cells, fresh human Pan-T cells (99% pure for CD3+ marker) from healthy donors purchased from All Cells (Alameda, Calif.), which were negatively isolated from mononuclear cells using an indirect immunomagnetic Pan-T labeling system, were tested. About $3 \times 10^5$ T cells were activated using anti-CD3/anti-CD28 magnetic beads as per manufacturer's protocol (Dynabeads®, Invitrogen, Carlsbad, Calif.). Briefly, a ratio of fresh primary T cells to beads used to activate the T cells was 1:1 (for every 80,000 T cells, 2 µl of beads were added). Test cells were treated simultaneously with various concentrations of MNK-specific inhibitor Compound 107 (0.01, 0.1, 1, 3 and 10 µM). After 48 hours, culture supernatants were harvested and examined via sandwich ELISA for the presence of IL-2 using human IL-2 ELISA DuoSet® (R&D Systems, Minneapolis, Minn.). The level of PD-1 expression, LAG3 expression and other T cell markers were examined by incubating cells with fixable dead cell stain (1:20,000; BD Biosciences) for 15 minutes at 4° C., washed twice with flow staining buffer (1x PBS, 4% FBS and 1 mM EDTA), incubated with human FcR block, then contacted with allophycocyanin (APC) conjugated anti-PD-1 antibody (Biolegend, San Diego, Calif.) or allophycocyanin (APC) conjugated anti-LAG3 antibody (eBioscience, San Diego, Calif.), as well as with phycoerythrin (PE) labelled anti-CD3 (BD Biosciences, San Jose, Calif.), and PE labelled anti-CD45 (BD Biosciences, San Jose, Calif.) for 30 minutes at 4° C., washed two times with flow buffer, and finally cells were fixed with fixation buffer (Cytofix™, BD Sciences, San Jose, Calif.) for 10 minutes at 4° C. After fixation, cells were washed twice with flow buffer and re-suspended in flow buffer and assessed for fluorescence using BD Accuri C6 cytometer. Data were analyzed using the C6 cytometer software (BD Biosciences, San Jose, Calif.).

PD-1 (CD279) Expression

Figure 3A:
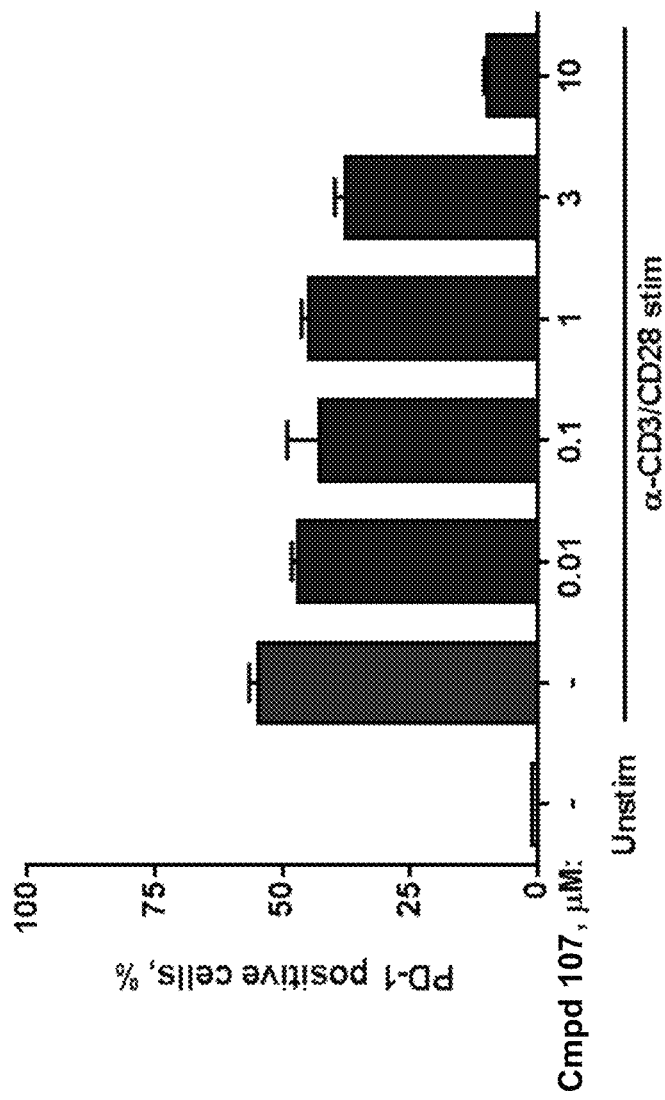
FIGS. 3A to 3G show that MNK-specific inhibitors can block the expression of various immune checkpoint proteins in fresh T cells activated with anti-CD3/anti-CD28 beads, without affecting T cell viability or activation. Flow cytometry shows that (A) and (B) PD-1 expression and (C) and (D) LAG3 are individually increased on primary T cells activated with anti-CD3/anti-CD28 beads, whereas PD-1 and LAG3 expression, respectively, is reduced in a dose dependent manner in the presence of MNK-specific inhibitor Compound 107 (used at 0.01, 0.1, 1, 3 and 10 μM). (E) An ELISA assay detected increased levels of human IL-2 production in T cells activated with anti-CD3/anti-CD28 beads. The presence of MNK-specific inhibitor Compound 107 did not detectably alter IL-2 production. (F) The viability of T cells activated with anti-CD3/anti-CD28 beads or activated with anti-CD3/anti-CD28 beads in the presence of Compound 107 was unaffected as determined by the percentage of dead cells detected using fixable dead cell stain (BD Biosciences, San Jose, Calif.). (G) Expression of IL-10, an immunosuppressive cytokine, was inhibited in primary T cells by Compound 107 in a dose dependent manner.
Figure 3B:
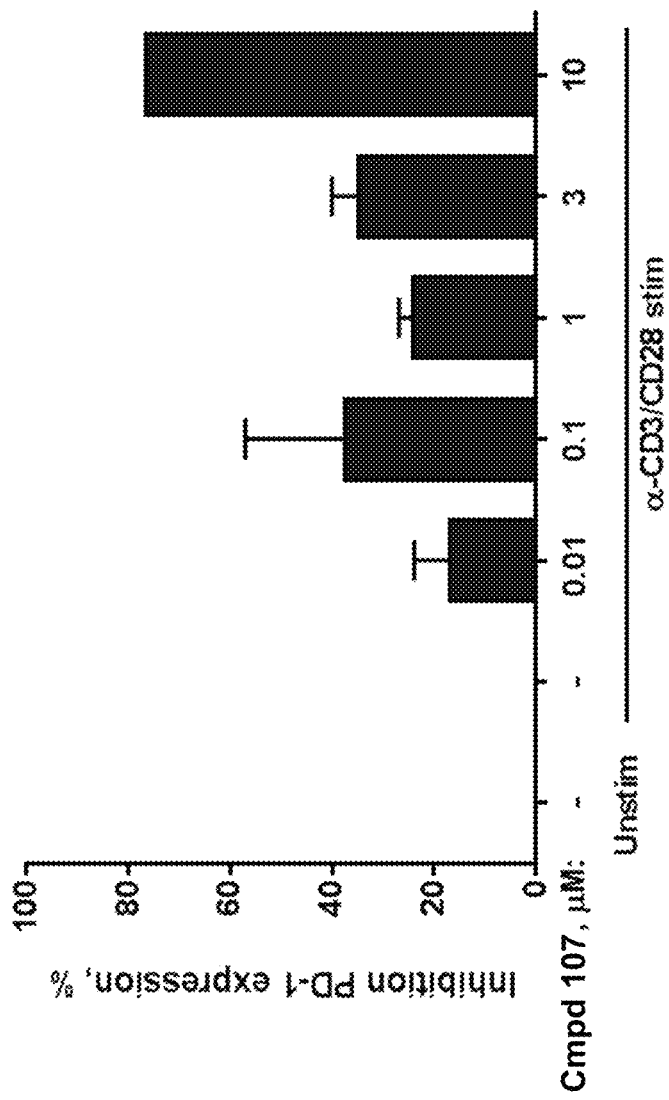
Figure 3C:
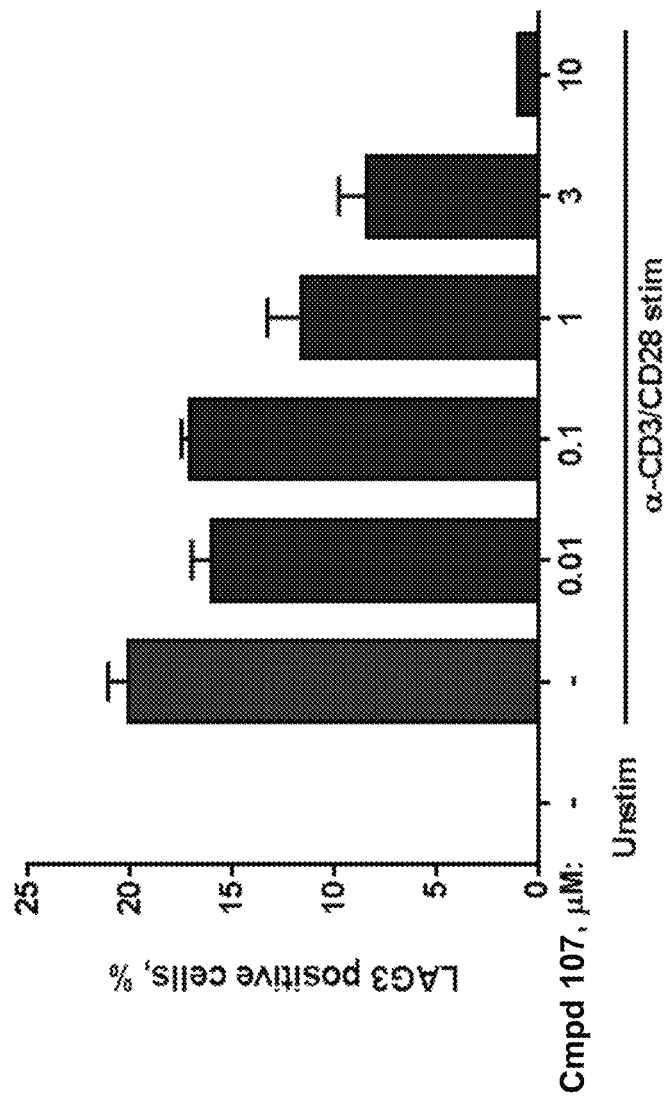
Figure 3D:
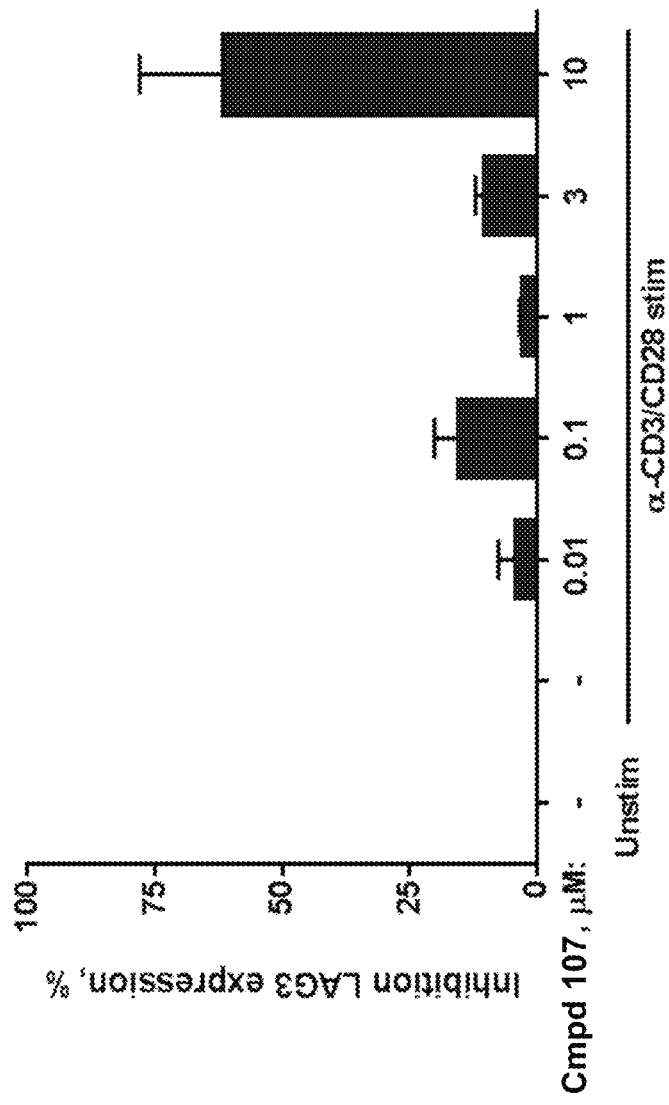
Figure 3E:
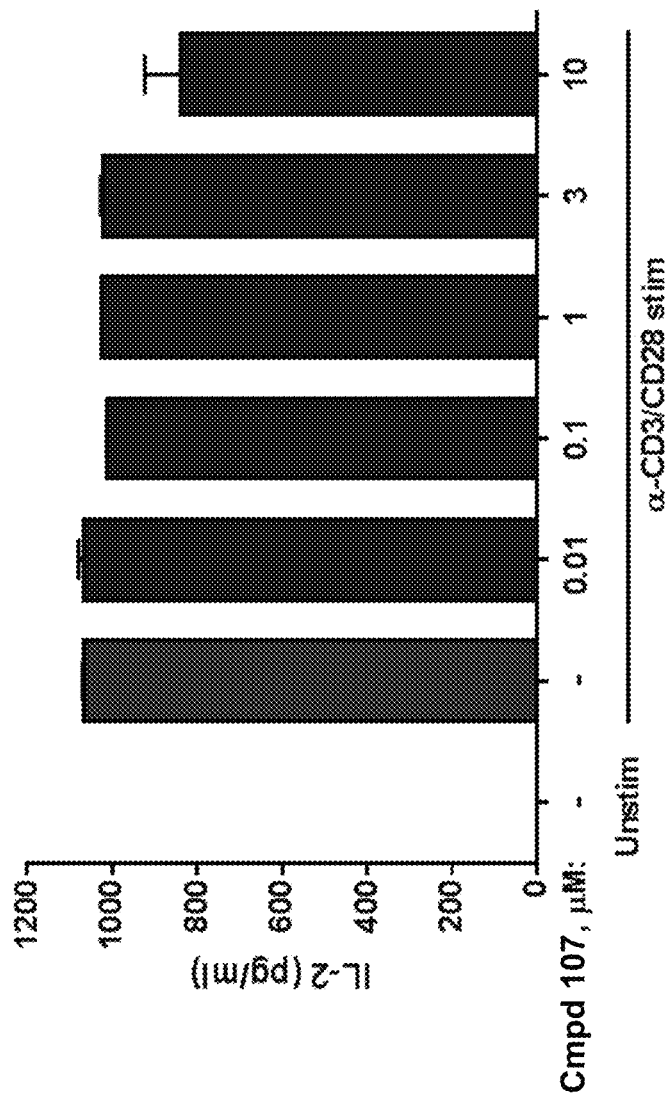
Figure 3F:
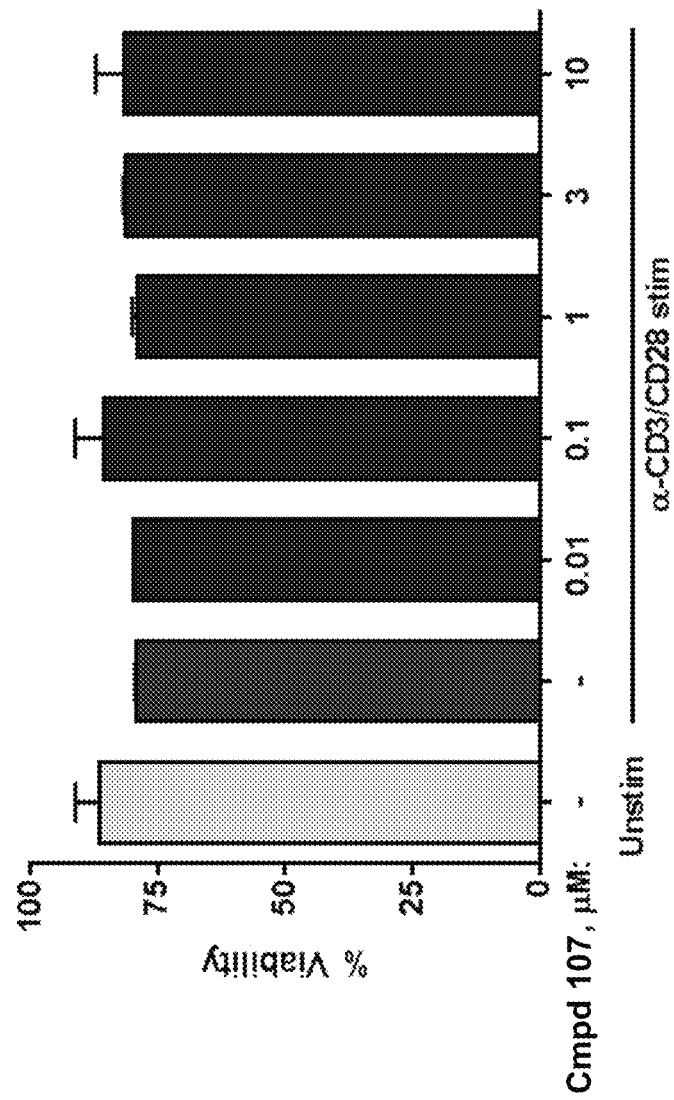

Consistent with the observation in Jurkat T cells, T cells activated with anti-CD3/anti-CD28 beads had increased cell surface expression of PD-1 on about 50% of the activated T cells (FIG. 3A), which indicated that the T cells were being activated via their T cell receptors (TCRs). Activation of the fresh primary T cells was further confirmed by examining the induction of a cytokine response. In particular, FIG. 3E shows that IL-2 was induced over 1,000-fold upon exposure to anti-CD3/anti-CD28 beads, which further indicated activation via TCRs. Treatment of activated T cells with the MNK-specific inhibitor Compound 107 resulted in a dose dependent decrease in the expression of the immune inhibitory receptor PD-1, with a maximum inhibition of 76% observed at 10 µM (see FIG. 3B). In addition, MNK-specific inhibition by Compound 107 did not detectably alter activation of cytokine production as measured by IL-2 level (see FIG. 3E), indicating that T cell activation is unaffected by the MNK-specific inhibitor. Lastly, MNK-specific inhibition with Compound 107 had no effect on T cell viability (FIG. 3F).

LAG3 (CD223) Expression

Also consistent with the observations in Jurkat T cells, stimulation of primary T cells through the T cell receptor (TCR) via anti-CD3/anti-CD28 crosslinking induced the expression of LAG3, which resulted in approximately 20% of T cells staining positive for LAG3 on their cell surface (FIG. 3C), as well as an increase in IL-2 production (FIG. 3E). LAG3 is found on CD8+ T cells and $T_{reg}$ cells, which functions to inhibit the innate immune response. Treatment of CD3/CD28 antibody bead activated T cells with the MNK-specific inhibitor Compound 107 resulted in a concentration dependent decrease in the expression of the immune inhibitory receptor LAG3, with a 62% reduction observed at 10 µM (FIG. 3D).

IL-10 Production

Figure 3G:
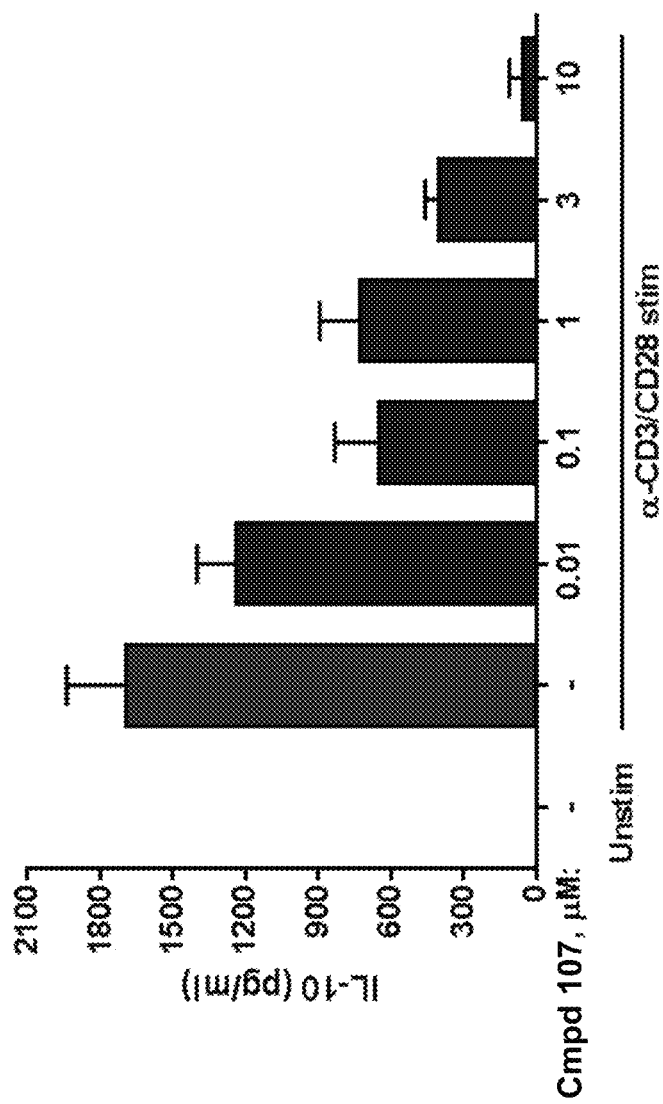

IL-10 is an immunosuppressive cytokine secreted by multiple cell types (e.g., Treg, Th1, Th2, cytotoxic T cells, dendritic cells, macrophages, myeloid-derived suppressor cells), which can inhibit immune responses in the context of a tumor microenvironment (see, e.g., Rabinovich et al., *Annu. Rev. Immunol.* 25:267, 2007; Rowlett et al., *Am. J. Physiol. Gastrointest. Liver Physiol.* 294:G452, 2008; and Ruffell and Coussens, *Cancer Cell* 27:462 2015). Interestingly, Compound 107 inhibited the production of IL-10 in a dose-dependent manner with a maximum inhibition of 96% at 10 µM (FIG. 3G), as did several other MNK-specific inhibitor compounds (Table 3).

TABLE 3

Effect of Various MNK-Specific Inhibitors on IL-10 Expression

| Compound | Structure | % IL-10 Inhibition* |
|---|---|---|
| 107 | 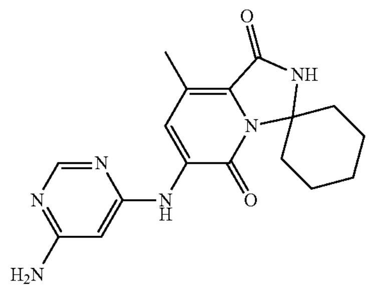 [SMILES: Cc1cc(Nc2cc(N)ncn2)c(=O)n2c1C(=O)NC21CCCCC1] | ++++ |
| 474 | 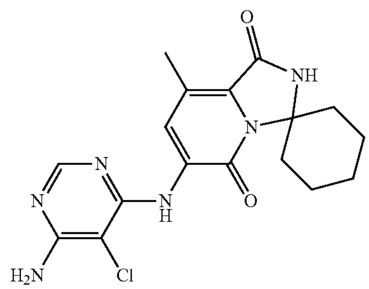 | ++++ |
| 590 | 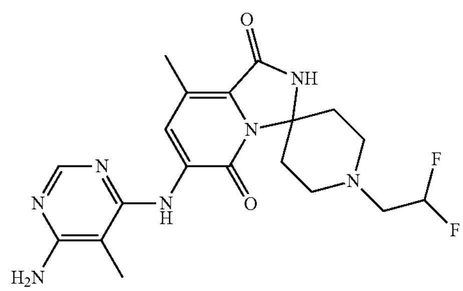 [SMILES: Cc1cc(Nc2ncnc(N)c2C)c(=O)n2c1C(=O)NC21CCN(CC(F)F)CC1] | ++++ |
| 750 | 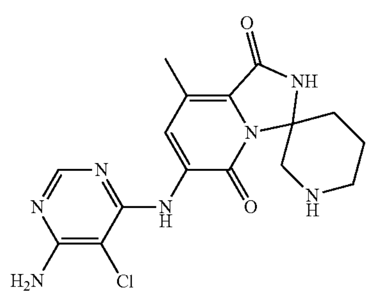 [SMILES: Cc1cc(Nc2ncnc(N)c2Cl)c(=O)n2c1C(=O)NC21CCCNC1] | ++++ |

*— = 0-10%; + = 10-25%; ++ = 25-50%; +++ = 50-75%; ++++ = 75-100%

Conclusion

Taken together with the results of Example 1, these data demonstrate that MNK either directly, or at the protein translation level, controls the expression of multiple immune checkpoint receptors (e.g., PD-1 and LAG3 in T cells) and ligands (e.g., PD-L1 in antigen presenting cells). In addition, specific inhibition of MNK resulted in a reduction in the production of the immunosuppressive cytokine IL-10. Finally, normal T cell function appeared to be undiminished by Compound 107 as assessed by IL-2 expression arising from TCR stimulation or T cell viability, again demonstrating a selective effect of Compound 107 on cellular signaling pathways.

Example 3

Effect of MNK-Specific Inhibitor on Antigen Presentation and Immune Recognition

Figure 7:
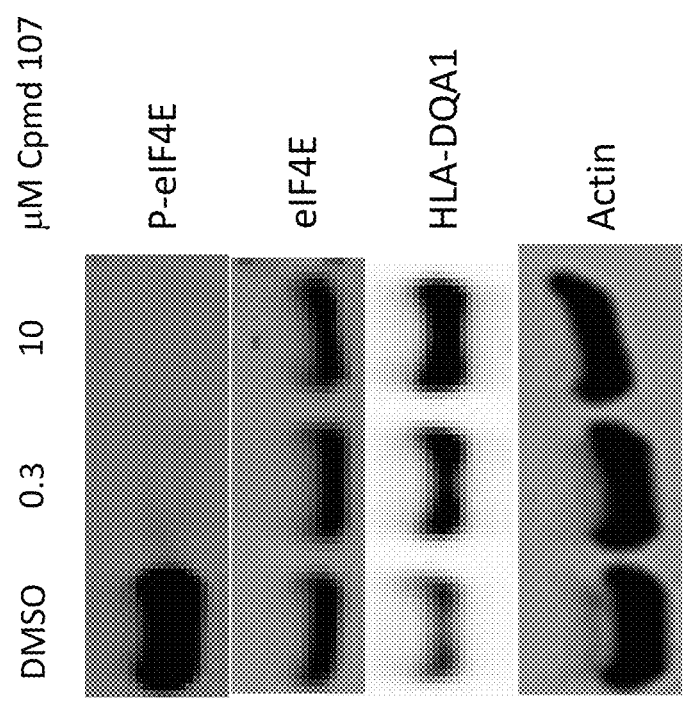
FIG. 7 shows a Western blot analysis of HLA-II (HLA-DQA1) protein levels in the diffuse large B-cell lymphoma (DLBCL) cell line TMD8 treated with a MNK-specific inhibitor for 48 hours.

The ability of MNK-specific inhibitor compounds to regulate the level of HLA class II proteins was evaluated in a diffuse large B-cell lymphoma (DLBCL) cell line, TMD8. Briefly, human DLBCL cell line TMD8 (ATCC), was cultured in RPMI media supplemented with penicillin G (100 U/ml), streptomycin (100 µg/ml), and 10% FBS in a humidified atmosphere of 5% $CO_2$ maintained at 37° C. About $2-4 \times 10^6$ TMD8 cells were seeded in 10 cm plates 24 hours prior to drug treatment. The following day, cells were treated with either vehicle control (DMSO) or Compound 107 at the indicated concentration (FIG. 7). Cells were harvested 48 hours post-treatment.

Treated cells were harvested, washed with PBS and lysed in 1×RIPA buffer (Thermo Fisher) for 15 minutes at 4° C. Lysates were clarified by centrifugation for 15 min at 14,000×rpm and supernatants were collected. Protein concentration in the soluble fraction was determined using the BCA protein assay (Thermo Scientific). Proteins were resolved on 4-20% Bis-Tris gradient polyacrylamide gel (Invitrogen) and transferred to nitrocellulose membrane. The resulting blots were blocked for 1 hour at room temperature with Odyssey blocking solution (LI-COR) and then incubated with anti-HLA-DQA1 (Abcam ab128959; 1:5000 dilution), anti-phospho-eIF4E (Millipore) and anti-eIF4E (Santa Cruz) at 4° C. overnight. The following day, the blots were washed for 10 minutes in TBST three times, and incubated with goat anti-rabbit fluorescent conjugated secondary antibody (IRDye 800 CW at 1:20,000; LI-COR) for 1 hour at room temperature. The blots were washed, scanned, and specific proteins detected using the LI-COR Odyssey infrared imager. The load control used was β-actin (Cell Signaling Technology at 1:3000).

Results

Expression of HLA class II protein HLA-DQA1 and the phosphorylation of eIF4E were analyzed by western blot analysis. Compound 107 potently inhibited the phosphorylation of eIF4E without affecting the total level eIF4E protein. Basal levels of HLA-DQA1 protein were low in the lymphoma TMD8 cell line. However, after 48 hours of Compound 107 treatment at either 300 nM or 10 µM, a dose dependent increase in HLA-DQA1 protein level was observed (estimated $EC_{50}$ of about 300 nM), while the level of β-actin (control) did not change (FIG. 7).

Conclusion

The detectable loss of HLA class II gene and protein expression in DLBCL has been related to decreased tumor immunosurveillance and poor patient survival. Treatment of the DLBCL cell line TMD8 with Compound 107 resulted in a dose dependent increase in protein expression of HLA-II HLA-DQA1. These results indicate that specific MNK-specific inhibitors can play an important role in antigen presentation by regulating the level of HLA/MHC class II protein, which can be important for eliciting an immune response.

Example 4

In Vivo Effect of a MNK-Specific Inhibitor or a MNK-Specific Inhibitor Combined with an Immune Checkpoint Inhibitor To evaluate the efficacy of a MNK-specific inhibitor in cancer, an in vivo allograft tumor model was used. Briefly, CT26 (mouse colon carcinoma) cells grown in DMEM supplemented with 10% FBS were harvested during exponential growth and counted for tumor inoculation in immune competent BALB/c mice. Each mouse was inoculated with $0.3\times10^6$ CT26 tumor cells in the right flank region in a 0.2 ml volume comprising a 1:1 ratio (volume to volume) of cells in growth media (0.1 ml) and Matrigel® matrix (0.1 ml) (BD Biosciences, San Jose Calif.). Tumors were allowed to grow to 100-200 mm³ prior to study initiation. Before beginning treatment, all animals were weighed and tumor volumes measured using a caliper. Since the tumor volume can affect the effectiveness of any given treatment, mice were randomly assigned into vehicle and test article treatment groups after tumors had reached a similar size. Each study group contained 8 mice, with each group receiving one of the following treatments: (1) Compound 107 in 10% 1-methyl-2-pyrrolidinone and 90% propylene glycol and given at a dose of 1 mg/kg orally, once a day; (2) anti-PD1 (BioXcell, Lebanon, N.H.) in PBS and given at a dose of 0.5 mg/mouse intraperitoneally, once every four days (as described by Wei et al., *PLoS One* 8:e84927, 2013); (3) a combination of Compound 107 at 1 mg/kg orally, once a day and anti-PD1 at 0.5 mg/mouse intraperitoneally, once every four days; (4) vehicle only control.

During the study, tumor size (for subcutaneous implants) was measured in length and width with a caliper twice a week. The tumor volume was calculated by the formula L×W×W/2 according to NCI standards. Tumor growth inhibition (TGI %) is an indication of anti-tumor effectiveness, which is expressed as follows: TGI (%)=100×(1−(ΔT/ΔC)). ΔT and ΔC were the change in mean tumor volume of the treated and control groups, relative to mean tumor volume at the start of treatment. All experiments continued until group mean tumor volume reached about 2000 to 2,500 mm³ in size. Groups that had a mean tumor size bigger than about 2000 mm³ to 2,500 were euthanized to ensure the quality of tumors for drug validation. Also, the body weight for each mouse was collected at least once prior to the study start, and twice a week during the study. Body weight change is an indication of tolerability, so percent body weight change is calculated as follows: body weight change (%)=100×(body weight$_{end}$−body weight$_{start}$)/body weight$_{start}$. Mice were also observed daily for mortality, mobility, hunched posture, piloerection, or other signs of distress while dosing. If a mouse lost greater than 20% body weight due to toxicity, or the combination of toxicity and tumor burden, it was euthanized. If there was apparent toxicity, the mice were taken off treatment and clinical observation and body weight measurement were done daily.

Results

Compound 107 was evaluated in vivo as a single agent and in combination with an anti-PD-1 monoclonal antibody in a BALB/c mouse allograft CT26 colon carcinoma tumor model. The measured tumor growth inhibition (TGI) and body weight changes are summarized in Table 3.

TABLE 3

Activity of MNK-Specific Inhibitor Alone and in Combination with Anti-PD-1 Antibody in a Mouse Colon Carcinoma Allograft Tumor Model

| Treatment | Dose | Body Weight Change[b] Average % | Tumor Growth Inhibition (% TGI)[c] | Mean Tumor Volume[c] (mm³) ± SEM | p-value[d] |
|---|---|---|---|---|---|
| Vehicle | —/day | 13.8 | —, — | 727.5 ± 233.5; 2594.1 ± 743.2 | — |
| Cmpd 107 | 1 mg/kg/day | 13.9 | 34, 54 | 522.3 ± 174.4; 1260.8 ± 499.1 | 0.354 |
| Anti-PD-1 | 0.5 mg/mouse[a] | 21.1 | 23, 33 | 586.0 ± 275.1; 1768.6 ± 991.3 | 0.664 |
| Cmpd 107 + anti-PD1 | 1 QD/ 0.5[a] | 3.8 | 99, 103 | 131.9 ± 55.0; 38.8 ± 17.5 | 0.0003 |

[a] anti-PD-1 antibody was dosed intraperitoneally once every 4 days (Q4D)
[b] Group average % body weight change calculated on final day of study (day 22)
[c] TGI and mean tumor volume was calculated 15 and 22 days after initiation of dosing
[d] p-value was calculated using a two-way ANOVA, no matching, corrected for multiple comparisons using Dunnett t-test (2-sided, equal variance assumed), relative to vehicle (day 22)

Figure 4A:
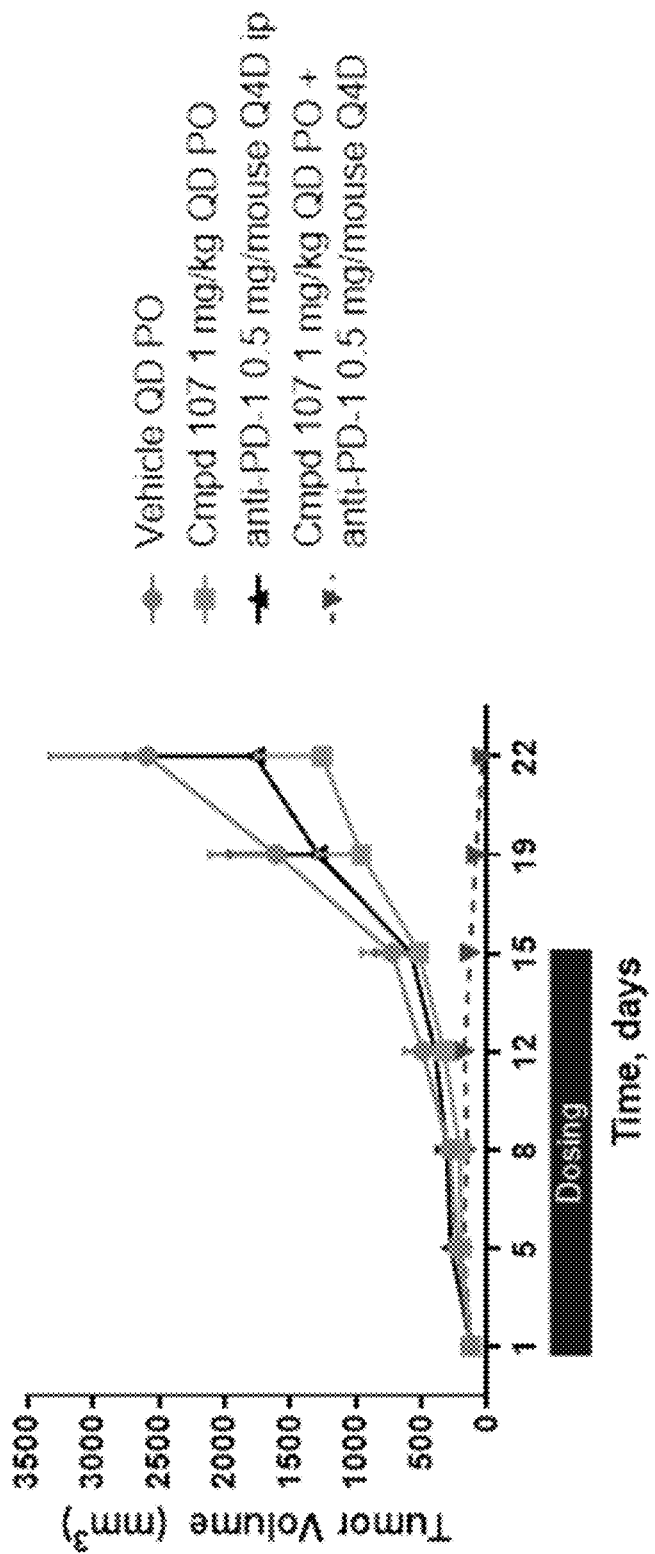
FIGS. 4A and 4B show that a MNK-specific inhibitor alone or a MNK-specific inhibitor in combination with an anti-PD-1 antibody can (A) inhibit tumor growth in an in vivo mouse CT26 allograft tumor model (B) without affecting body weight (which indicates tolerability).
Figure 4B:
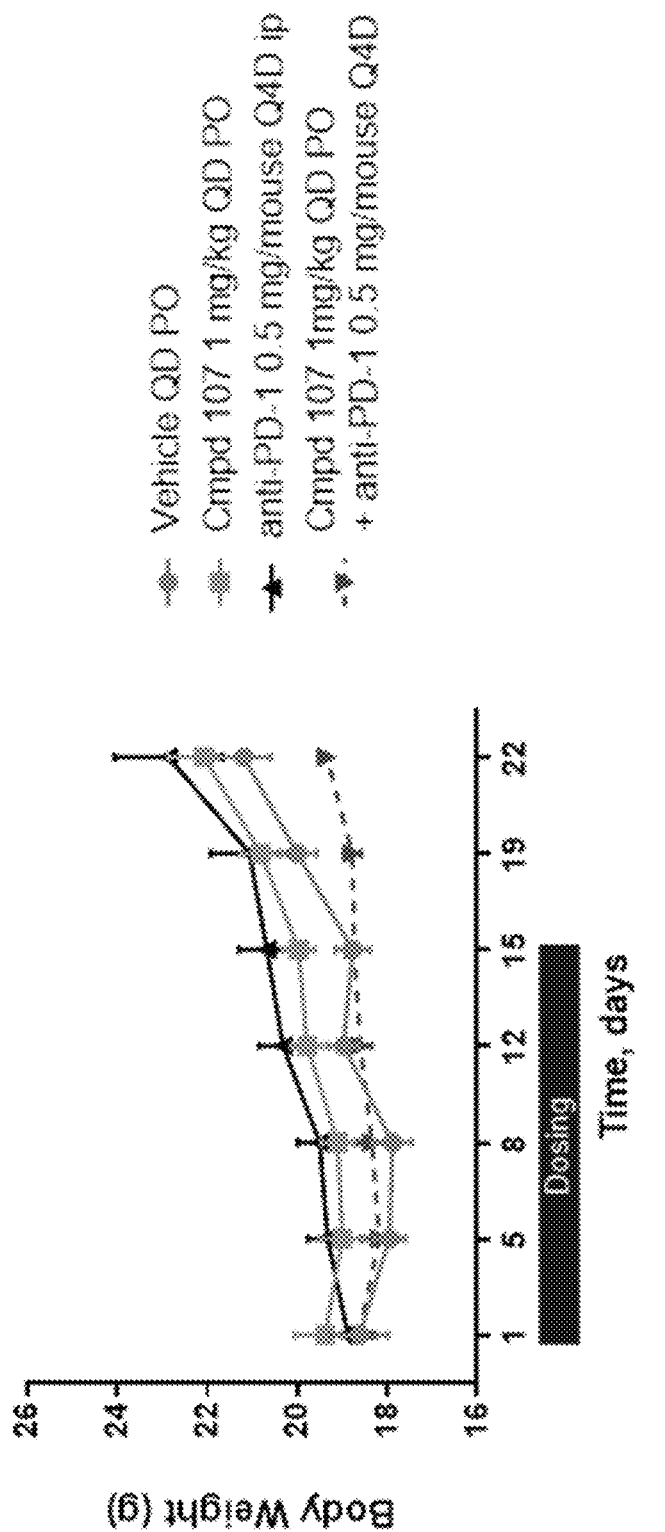

Oral treatment with 1 mg/kg once daily (QD) of Compound 107 yielded moderate tumor growth inhibition of about 34% (FIG. 4A) during the 15 day treatment period, although it is important to note that several Compound 107-treated animals had tumors that continued to regress after cessation of dosing (about 55% at day 22). Intraperitoneal treatment of mice having a CT26 allograft tumor with anti-PD-1 antibody at a dose of 0.5 mg/mouse once every four days also resulted in a somewhat less tumor growth inhibition of about 23%. Similar to the Compound 107 group, multiple anti-PD-1 treated animals had tumors that continued to regress after treatment was stopped (about 33% at day 22). Body weight was not significantly impacted (FIG. 4B), meaning the treatments were well tolerated. Surprisingly, the combination of Compound 107 with anti-PD-1 antibody yielded a remarkable synergistic tumor growth inhibition of about 99% on day 15 (FIG. 4A), with the majority of animals becoming tumor free by the end of study (day 22).

Tumor Re-Challenge

Previously treated allograft mice that responded to therapy or were tumor-free from each treatment group (8 days post-treatment) were tested for development of long-term immune memory by re-implanting new CT26 tumors and assessing for tumor growth compared to naïve BALB/c mice. Briefly, treated mice were re-implanted and naïve were implanted for the first time with tumor cells in the left flank region in 0.1 ml of growth media and an equal 0.1 ml volume ratio of Matrigel® matrix (1:1 volume to volume ratio), as before. Tumors in these untreated mice were measured following implantation as described herein. Results from the re-challenge experiment are summarized in Table 4.

TABLE 4

CT26 Tumor Re-Challenge of Complete Responders

| Prior treatment | No./Study Group | Tumor Formation | Mean Tumor Volume$^a$ (mm$^3$) ± SEM | p value$^b$ |
|---|---|---|---|---|
| Naïve | 10 | 10/10 | 156.2 ± 15.6 | — |
| Cmpd 107 | 4 | 0/4 | 22.4 ± 4.5 | <0.0001 |
| Anti-PD-1 | 4 | 0/4 | 18.8 ± 3.5 | <0.0001 |
| Cmpd 107 + Anti-PD-1 | 7 | 0/7 | 6.0 ± 2.6 | <0.0001 |

$^a$Mean tumor volume was calculated 8 days after tumor implant.
$^b$p-value was calculated using a one-way ANOVA, no matching, corrected for multiple comparisons using Dunnett t-test, relative to naïve control.

Figure 5:
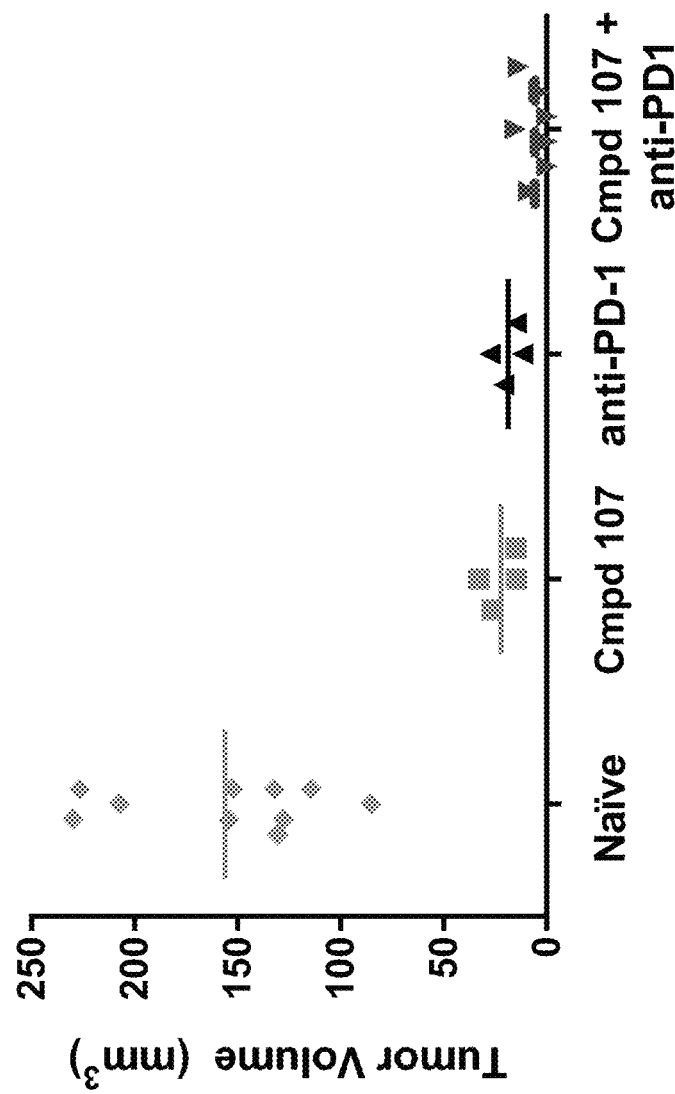
FIG. 5 shows that mice that had responded to treatment with a MNK-specific inhibitor alone, an anti-PD-1 antibody alone, or a MNK-specific inhibitor in combination with an anti-PD-1 antibody rejected CT26 tumor upon re-challenge. Tumor growth was assessed in the absence of further drug treatment as compared to naïve BALB/c mice implanted with the same CT26 allograft tumor, which indicates that prior treatment with a MNK-specific inhibitor established long-term immune memory.

All re-challenged mice were resistant to CT26 tumor formation, with 0/4 animals previously exposed to Compound 107, 0/4 animals previously exposed to anti-PD-1, and 0/7 animals previously exposed to the combination of Compound 107 with anti-PD-1 showing any measurable tumor (FIG. 5). In contrast, all naïve BALB/c control mice (10/10) had measurable CT26 tumors form. Unexpectedly, this result indicates that mice that demonstrated a previous response to Compound 107 monotherapy or the combination of Compound 107 plus anti-PD-1 had long-term immune memory to tumor antigens expressed in the CT26 tumor.

Example 5

In Vivo Effect of a MNK-Specific Inhibitor on $T_{reg}$ Cells

Tumor-induced immune suppression involves a multitude of mechanisms, including accumulation of immune-suppressive infiltrates in the tumor microenvironment, such as T regulatory ($T_{reg}$) cells. There is increasing evidence that $T_{reg}$ cells may play a role in immune evasion mechanisms in cancer and that tumors may potently abrogate antitumor immunity through $T_{Reg}$ cells (Schabowsky et al., Curr. Opin. Investig. Drugs 8:1002, 2007; Liu et al., J. Immunol. 182:6160, 2009). To examine whether altering immune checkpoint mechanisms had an effect on $T_{reg}$ cells in a CT26 allograft model, tumor infiltrating lymphocytes (TILs) in tumors isolated from treated mice were examined for changes in T effector (CD8$^+$) and T regulatory (FOXP3$^+$) cell populations.

Mice having established CT26 tumors (100-200 mm$^3$) were treated with compound 107, anti-PD1 antibody or a combination of compound 107 and anti-PD-1 antibody, as described in Example 4. After 4 days of treatment, the mice were euthanized and tumors were excised. A single cell suspension was generated by dissecting excised tumors into fine pieces with a razor blade, incubating with collagenase, hyaluronidase and DNAse I (Worthington Biochemical, Lakewood N.J.) in RPMI, incubating in 1× trypsin-EDTA, and finally passaging through a 70 micron cell strainer filter (BD Biosciences, San Jose Calif.). To analyze the amount of T effector ($T_E$, CD3$^+$/CD8$^+$) and T regulatory ($T_{reg}$, CD4$^+$/FOXP3$^+$) cells present in the tumor, cells were incubated with fixable dead cell stain (1:20,000; BD Biosciences, San Jose, Calif.) for 15 minutes at 4° C., washed twice with flow staining buffer (1×PBS, 4% FBS and 1 mM EDTA), incubated with human FcR block (Miltenyi Biotech, San Diego Calif.), and stained with antibody cocktails specific for CD45 (CD45 PerCP-Cy5.5, BD Biosciences, San Jose Calif.), CD3 (CD3-APC, EBiosciences, San Diego Calif.), and CD8 (CD8-PE, BD Biosciences, San Jose Calif.) or for CD45 (CD45 PerCP-Cy5.5, BD Biosciences) and CD4 (CD4-APC, BD Biosciences), following the manufacturer's protocol. For samples assessed for CD45/CD3/CD8, cells were washed twice with flow buffer and incubated with fixation buffer for 10 minutes at 4° C. After fixation, cells were washed twice with flow buffer and re-suspended in flow buffer for flow cytometry analysis. Samples assessed for CD45/CD4 were further processed for intracellular staining of FOXP3 using an anti-FOXP3 antibody (FOXP3-PE, BD Biosciences) and the FOXP3/Transcription Factor staining buffer set (eBiosciences, San Diego Calif.) following the manufacturer's protocol. Cells were washed twice with 1× permeabilization buffer and re-suspended in permeabilization buffer for flow cytometry analysis. Data were collected and analyzed using a BD Accuri C6 flow cytometer (BD Biosciences, San Jose Calif.). The ratio of $T_E$ to $T_{reg}$ cells was calculated by determining the percentage of CD3$^+$/CD8$^+$ cells present in the CD45$^+$ lymphocyte population and dividing by the percentage of CD4$^+$/FOXP3$^+$ present from the same population.

Results

Figure 6:
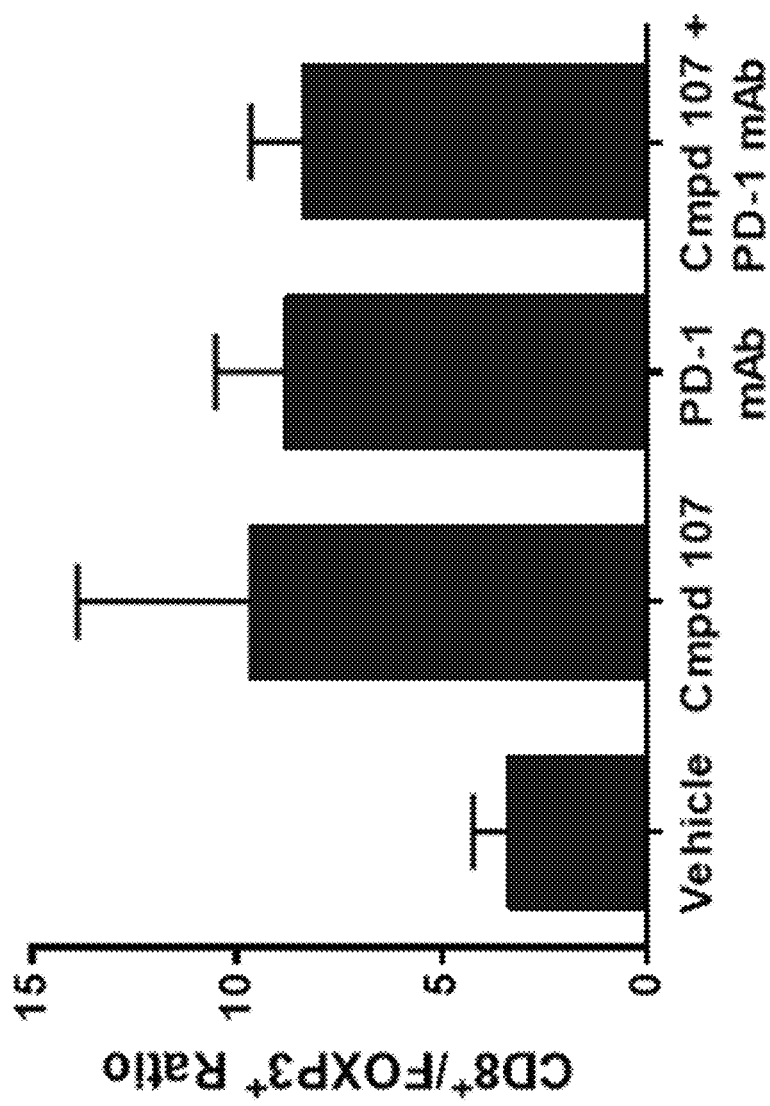
FIG. 6 shows that a MNK-specific inhibitor alone or a MNK-specific inhibitor in combination with an anti-PD-1 antibody can alter the in vivo ratios of T effector cells to T regulatory cells in a population of tumor infiltrating lymphocytes (TILs) isolated four days after treatment from a mouse CT26 allograft tumor.

In the vehicle control, the average $T_E$:$T_{reg}$ ratio was 3.4 (FIG. 6). Mice treated with Compound 107 showed an increased average $T_E$:$T_{reg}$ ratio to 9.7. Similar results were observed with the anti-PD-1 antibody, where treatment increased the average $T_E$:$T_{reg}$ ratio to 8.8, which is consistent with previous reports for this compound (Duraiswamy et al., Cancer Res. 73:3591, 2013). Finally, the combination of Compound 107 with anti-PD-1 antibody increased the average $T_E$:$T_{reg}$ ratio to 8.4.

Conclusion

These results demonstrate that MNK-specific inhibitors can modulate TIL populations within tumors in vivo to reduce the number of $T_{reg}$ cells and allow $T_E$ cells to more effectively clear pathogenic cells.

The various embodiments described herein can be combined to provide further embodiments. All of the patents, patent application publications, patent applications, and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method of inducing or enhancing an immune response, comprising administering a therapeutically effective amount of a MNK-specific inhibitor and an inhibitor of an immunosuppression component to a subject in need thereof, thereby inducing or enhancing an immune response, wherein the inhibitor of an immunosuppression component is an antibody specific for PD-1, PD-L1, CLA4, or a combination thereof, wherein
a) the antibody specific for PD-1 is pidilizumab, nivolumab, pembrolizumab, MK-3475, or any combination thereof,
b) the antibody specific for PD-L1 is MDX-1105, BMS-936559, durvalumab (MEDI4736), atezolizumab (MPDL3280A), MSB0010718C, or any combination thereof; and
c) the antibody specific for CTLA4 is tremelimumab, ipilimumab, or both,
wherein, wherein the MNK-specific inhibitor has the following Formula (I):

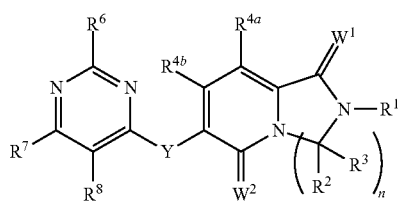

or a stereoisomer, tautomer or pharmaceutically acceptable salt thereof, wherein:
$W^1$ and $W^2$ are independently O, S or N—OR', where R' is lower alkyl;
Y is $N(R^5)$, —O—, —S—, —C(O)—, —S═O, —S(O)$_2$—, or —CHR$^9$—;
$R^1$ is hydrogen, lower alkyl, cycloalkyl or heterocyclyl wherein any lower alkyl, cycloalkyl or heterocyclyl is optionally substituted with 1, 2 or 3 J groups;
n is 1, 2 or 3;
$R^2$ and $R^3$ are each independently hydrogen, alkyl, alkenyl, alkynyl, aryl, araalkylene, heteroaryl, heteroarylalkylene, cycloalkyl, cycloalkylalkylene, heterocyclyl, or heterocyclylalkylene, wherein any alkyl, aryl, araalkylene, heteroaryl, heteroarylalkylene, cycloalkyl, cycloalkylalkylene, heterocyclyl, or heterocyclylalkylene, is optionally substituted with 1, 2 or 3 J groups;
or $R^2$ and $R^3$ taken together with the carbon atom to which they are attached form a cycloalkyl or heterocyclyl, wherein any cycloalkyl or heterocyclyl is optionally substituted with 1, 2 or 3 J groups;

$R^{4a}$ and $R^{4b}$ are each independently hydrogen, halogen, hydroxyl, thiol, hydroxyalkylene, cyano, alkyl, alkoxy, acyl, thioalkyl, alkenyl, alkynyl, cycloalkyl, aryl, or heterocyclyl;
$R^5$ is hydrogen, cyano, or lower alkyl;
or $R^5$ and $R^8$ taken together with the atoms to which they are attached form a fused heterocyclyl optionally substituted with 1, 2 or 3 J groups;
$R^6$, $R^7$ and $R^8$ are each independently hydrogen, hydroxy, halogen, cyano, amino, alkyl, alkenyl, alkynyl, alkoxy, cycloalkyl, cycloalkylalkylene, cycloalkylalkenylene, alkylaminyl, alkylcarbonylaminyl, cycloalkylcarbonylaminyl, cycloalkylaminyl, heterocyclylaminyl, heteroaryl, or heterocyclyl, and wherein any amino, alkyl, alkenyl, alkynyl, alkoxy, cycloalkyl, cycloalkylalkylene, cycloalkylalkenylene, amino, alkylaminyl, alkylcarbonylaminyl, cycloalkylcarbonylaminyl, cycloalkylaminyl, heterocyclylaminyl, heteroaryl, or heterocyclyl is optionally substituted with 1, 2 or 3 J groups;
or $R^7$ and $R^8$ taken together with the atoms to which they are attached form a fused heterocyclyl or heteroaryl optionally substituted with 1, 2 or 3 J groups;
J is —SH, —SR$^9$, —S(O)R$^9$, —S(O)$_2$R$^9$, —S(O)NH$_2$, —S(O)NR$^9$R$^9$, —NH$_2$, —NR$^9$R$^9$, —COOH, —C(O)OR$^9$, —C(O)R$^9$, —C(O)—NH$_2$, —C(O)—NR$^9$R$^9$, hydroxy, cyano, halogen, acetyl, alkyl, lower alkyl, alkenyl, alkynyl, alkoxy, haloalkyl, thioalkyl, cyanoalkylene, alkylaminyl, NH$_2$—C(O)-alkylene, NR$^9$R$^9$—C(O)-alkylene, —CHR$^9$—C(O)-lower alkyl, —C(O)-lower alkyl, alkylcarbonylaminyl, cycloalkyl, cycloalkyl alkylene, cycloalkylalkenylene, cycloalkylcarbonyl aminyl, cycloalkyl aminyl, —CHR$^9$—C(O)-cycl ° alkyl, —C(O)— cycloalkyl, —CHR$^9$—C(O)-aryl, —CHR$^9$-aryl, —C(O)-aryl, —CHR$^9$—C(O)-heterocycloalkyl, —C(O)— heterocycloalkyl, heterocyclylaminyl, or heterocyclyl; or any two J groups bound to the same carbon or hetero atom may be taken together to form oxo; and
$R^9$ is hydrogen, lower alkyl or —OH.

2. The method of claim 1, wherein the subject in need of an induced or enhanced immune response has a disease associated with immune resistance.

3. The method of claim 1, wherein the disease associated with immune resistance is a cancer or an infection.

4. The method of claim 3, wherein the cancer is a solid tumor, melanoma, non-small cell lung cancer, renal cell carcinoma, renal cancer, a hematological cancer, prostate cancer, castration-resistant prostate cancer, colon cancer, rectal cancer, gastric cancer, esophageal cancer, bladder cancer, head and neck cancer, thyroid cancer, breast cancer, triple-negative breast cancer, ovarian cancer, cervical cancer, lung cancer, urothelial cancer, pancreatic cancer, glioblastoma, hepatocellular cancer, myeloma, multiple myeloma, leukemia, Hodgkin's lymphoma, non-Hodgkin's lymphoma, myelodysplastic syndrome, brain cancer, CNS cancer, malignant glioma, or any combination thereof.

5. The method of claim 3, wherein the infection is a viral, bacterial, fungal, or parasitic infection.

6. The method of claim 5, wherein the viral infection is an infection by a flavivirus, herpes virus, hepatitis virus, papillomavirus, paramyxovirus, retrovirus, lentivirus, or varicella-zoster virus.

7. The method of claim 5, wherein the viral infection is an infection by a hepatitis C virus (HCV), hepatitis B virus (HBV), hepatitis A virus, hepatitis E virus, Japanese encephalitis virus, or human immunodeficiency virus (HIV).

8. The method of claim 1, wherein the induced or enhanced immune response is an antigen-specific T cell response.

9. The method of claim 1, wherein the method further comprises administering a therapy that induces or enhances an anti-cancer response.

10. The method of claim 9, wherein the induced or enhanced anti-cancer response is an anti-tumor response.

11. The method of claim 9, wherein the therapy that induces or enhances an anti-cancer response is a vaccine, an inhibitor of an immunosuppression component, a B-Raf inhibitor, a MEK inhibitor, a VEGF inhibitor, a VEGFR inhibitor, a tyrosine kinase inhibitor, a cytotoxic agent, a chemotherapeutic, or any combination thereof.

12. The method of claim 11, wherein the therapy that induces or enhances an anti-cancer response is the inhibitor of an immunosuppression component, the inhibitor of an immunosuppression component comprising an antibody or siRNA.

13. The method of claim 11, wherein the therapy that induces or enhances an anti-cancer response is the chemotherapeutic, the chemotherapeutic comprising a B-Raf inhibitor, a MEK inhibitor, a VEGF inhibitor, a VEGFR inhibitor, a tyrosine kinase inhibitor, an anti-mitotic agent, or any combination thereof.

14. The method of claim 11, wherein the therapy that induces or enhances an anti-cancer response is the chemotherapeutic, the chemotherapeutic is selected from vemurafenib, dabrafenib, trametinib, cobimetinib, sunitinib, erlotinib, paclitaxel, docetaxel, or any combination thereof.

15. The method of claim 1, wherein the MNK-specific inhibitor and inhibitor of an immunosuppression component are administered simultaneously, concurrently, sequentially, or any combination thereof.

16. The method of claim 9, wherein the MNK-specific inhibitor and therapy that induces or enhances an anti-cancer response are administered simultaneously, concurrently, sequentially, or any combination thereof.

17. The method of claim 1, wherein the MNK-specific inhibitor reduces the expression of PD-1, PD-L1, and LAG3.

18. The method of claim 17, wherein the expression of PD-1 and LAG3 is reduced in a T cell.

19. The method of claim 17, wherein the expression of PD-L1 is reduced in an antigen presenting cell or a disease-associated cell.

20. The method of claim 1, wherein the MNK-specific inhibitor reduces or minimizes the ability of MNK to phosphorylate eIF4E.

21. A method of inducing or enhancing an immune response, comprising administering a therapeutically effective amount of a MNK-specific inhibitor and an effective amount of an inhibitor of an immunosuppression component to a subject in need thereof, thereby inducing or enhancing an immune response, wherein the MNK-specific inhibitor is a compound:

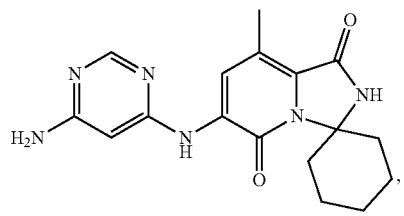 [SMILES: Cc1cc(Nc2cc(N)ncn2)c(=O)n2c1C(=O)NC21CCCCC1]

or a stereoisomer, tautomer or pharmaceutically acceptable salt thereof, and wherein the inhibitor of an immunosuppression component is an antibody specific for PD-1, PD-L1, CLA4, or any combination thereof, wherein
a) the antibody specific for PD-1 is pidilizumab, nivolumab, pembrolizumab, MK-3475, or any combination thereof,
b) the antibody specific for PD-L1 is MDX-1105, BMS-936559, durvalumab (MEDI4736), atezolizumab (MPDL3280A), MSB0010718C, or any combination thereof; and
c) the antibody specific for CTLA4 is tremelimumab, ipilimumab, or both.

22. The method of claim 21, wherein the antibody specific for PD-1 is nivolumab or pembrolizumab.

23. The method of claim 21, wherein the antibody specific for PD-L1 is durvalumab or atezolizumab.

* * * * *